us007448594B2

(12) United States Patent
Voege et al.

(10) Patent No.: US 7,448,594 B2
(45) Date of Patent: Nov. 11, 2008

(54) FLUID REGULATOR

(75) Inventors: James A. Voege, Carmel, IN (US); David A. Ferrer, Westfield, IN (US)

(73) Assignee: Ameriflo, Inc., Carmel, IN (US)

( * ) Notice: Subject to any disclaimer, the term of this patent is extended or adjusted under 35 U.S.C. 154(b) by 264 days.

(21) Appl. No.: 11/255,550

(22) Filed: Oct. 21, 2005

(65) Prior Publication Data

US 2007/0083176 A1    Apr. 12, 2007

Related U.S. Application Data

(60) Provisional application No. 60/620,890, filed on Oct. 21, 2004.

(51) Int. Cl.
*F16K 5/02* (2006.01)
(52) U.S. Cl. ........................ 251/207; 251/118; 137/507; 137/557
(58) Field of Classification Search ................ 251/118, 251/205, 206, 207; 137/505.25, 507, 557
See application file for complete search history.

(56) References Cited

U.S. PATENT DOCUMENTS

| | | |
|---|---|---|
| 2,912,979 A | 11/1959 | Lieber |
| 3,400,712 A | 9/1968 | Finan |
| 3,400,713 A | 9/1968 | Finan |
| 3,434,471 A | 3/1969 | Liston |
| 3,556,095 A | 1/1971 | Ismach |
| 3,567,175 A | 3/1971 | Sciuto |
| 3,604,415 A | 9/1971 | Hoenig |
| 3,643,660 A | 2/1972 | Hudson et al. |
| 3,741,208 A | 6/1973 | Jonsson et al. |
| 3,783,891 A | 1/1974 | Christianson |
| 3,802,417 A | 4/1974 | Lang |
| 3,805,780 A | 4/1974 | Cramer et al. |
| 3,807,687 A | 4/1974 | Thompson |
| 3,830,257 A | 8/1974 | Metivier |
| 3,834,382 A | 9/1974 | Lederman et al. |
| 3,905,362 A | 9/1975 | Eyrick et al. |
| 3,910,270 A | 10/1975 | Stewart |
| 3,911,899 A | 10/1975 | Hattes |
| 3,911,948 A | 10/1975 | Collins et al. |
| 3,949,749 A | 4/1976 | Stewart |

(Continued)

FOREIGN PATENT DOCUMENTS

DE    27 11 664    10/1977

(Continued)

OTHER PUBLICATIONS

Esco$_2$rt Pulse—Conserving Regulator literature, The Respiratory Group, 2002, 2 pgs.

(Continued)

*Primary Examiner*—John K Fristoe, Jr.
(74) *Attorney, Agent, or Firm*—Baker & Daniels LLP

(57) ABSTRACT

Fluid regulators are disclosed. An exemplary fluid regulator having a cylindrical body and a reduced diameter portion adjacent an open end of the fluid regulator along with a flow selector positioned adjacent the open end of the fluid regulator and having a diameter larger than the reduced diameter of the cylindrical body is disclosed. Another exemplary fluid regulator having a pressure reduction section positioned within a housing is disclosed.

28 Claims, 46 Drawing Sheets

U.S. PATENT DOCUMENTS

| | | |
|---|---|---|
| 3,964,476 A | 6/1976 | Palleni |
| 4,003,377 A | 1/1977 | Dahl |
| 4,008,716 A | 2/1977 | Amlong |
| 4,033,343 A | 7/1977 | Jones |
| 4,054,133 A | 10/1977 | Myers |
| 4,057,059 A | 11/1977 | Reid, Jr. et al. |
| 4,062,356 A | 12/1977 | Merrifield |
| 4,064,890 A | 12/1977 | Collins et al. |
| 4,082,093 A | 4/1978 | Fry et al. |
| 4,096,875 A | 6/1978 | Jones et al. |
| 4,098,272 A | 7/1978 | Stewart |
| 4,106,503 A | 8/1978 | Rosenthal et al. |
| 4,120,300 A | 10/1978 | Tiep |
| 4,155,356 A | 5/1979 | Venegas |
| 4,172,468 A | 10/1979 | Ruus |
| 4,206,754 A | 6/1980 | Cox et al. |
| 4,211,221 A | 7/1980 | Schwanbom et al. |
| 4,227,523 A | 10/1980 | Warnow et al. |
| 4,232,668 A | 11/1980 | Strupat |
| 4,241,732 A | 12/1980 | Berndtsson |
| 4,241,896 A | 12/1980 | Voege |
| 4,256,138 A | 3/1981 | Chapman |
| 4,278,110 A | 7/1981 | Price et al. |
| 4,323,064 A | 4/1982 | Hoenig et al. |
| 4,333,451 A | 6/1982 | Paluch |
| 4,336,590 A | 6/1982 | Jacq et al. |
| 4,363,424 A | 12/1982 | Holben et al. |
| 4,366,947 A | 1/1983 | Voege |
| 4,381,002 A | 4/1983 | Mon |
| 4,409,977 A | 10/1983 | Bisera et al. |
| 4,436,090 A | 3/1984 | Darling |
| 4,436,434 A | 3/1984 | Stoll et al. |
| 4,450,838 A | 5/1984 | Miodownik |
| 4,457,303 A | 7/1984 | Durkan |
| 4,459,982 A | 7/1984 | Fry |
| 4,461,293 A | 7/1984 | Chen |
| 4,471,773 A | 9/1984 | Bunnell et al. |
| 4,481,944 A | 11/1984 | Bunnell |
| 4,532,923 A | 8/1985 | Flynn |
| 4,538,604 A | 9/1985 | Usry et al. |
| 4,572,175 A | 2/1986 | Flynn |
| 4,575,042 A | 3/1986 | Grimland et al. |
| 4,581,942 A | 4/1986 | Ogura et al. |
| 4,584,996 A | 4/1986 | Blum |
| 4,586,136 A | 4/1986 | Lewis |
| 4,592,349 A | 6/1986 | Bird |
| 4,596,247 A | 6/1986 | Whitwam et al. |
| 4,612,928 A | 9/1986 | Tiep et al. |
| 4,617,924 A | 10/1986 | Heim et al. |
| 4,644,947 A | 2/1987 | Whitwam et al. |
| 4,644,958 A | 2/1987 | Brisson et al. |
| 4,648,395 A | 3/1987 | Sato et al. |
| 4,655,246 A * | 4/1987 | Phlipot et al. .......... 137/505.11 |
| 4,665,911 A | 5/1987 | Williams et al. |
| 4,699,173 A | 10/1987 | Rohling |
| 4,706,664 A | 11/1987 | Snook et al. |
| 4,712,557 A | 12/1987 | Harris |
| 4,719,910 A | 1/1988 | Jensen |
| 4,744,356 A | 5/1988 | Greenwood |
| 4,747,402 A | 5/1988 | Reese et al. |
| 4,747,403 A | 5/1988 | Gluck et al. |
| 4,784,130 A | 11/1988 | Kenyon et al. |
| 4,805,612 A | 2/1989 | Jensen |
| 4,821,709 A | 4/1989 | Jensen |
| 4,823,788 A | 4/1989 | Smith et al. |
| 4,827,922 A | 5/1989 | Champain et al. |
| 4,829,998 A | 5/1989 | Jackson |
| 4,832,014 A | 5/1989 | Perkins |
| 4,838,257 A | 6/1989 | Hatch |
| 4,909,476 A * | 3/1990 | Messick .................. 251/206 |
| 4,932,402 A | 6/1990 | Snook et al. |
| 4,938,212 A | 7/1990 | Snook et al. |
| 4,971,049 A | 11/1990 | Rotariu et al. |
| 4,986,268 A | 1/1991 | Tehrani |
| 5,005,570 A | 4/1991 | Perkins |
| 5,007,420 A | 4/1991 | Bird |
| 5,016,673 A | 5/1991 | Carter et al. |
| 5,048,515 A | 9/1991 | Sanso |
| 5,052,400 A | 10/1991 | Dietz |
| 5,074,299 A | 12/1991 | Dietz |
| 5,092,326 A | 3/1992 | Winn et al. |
| 5,099,837 A | 3/1992 | Russel, Sr. et al. |
| 5,116,088 A | 5/1992 | Bird |
| 5,165,397 A | 11/1992 | Arp |
| 5,183,037 A | 2/1993 | Dearman |
| 5,199,424 A | 4/1993 | Sullivan et al. |
| 5,211,171 A | 5/1993 | Choromokos |
| 5,241,955 A | 9/1993 | Dearman et al. |
| 5,245,995 A | 9/1993 | Sullivan et al. |
| 5,259,373 A | 11/1993 | Gruenke et al. |
| 5,315,988 A | 5/1994 | Clarke et al. |
| 5,331,995 A | 7/1994 | Westfall et al. |
| 5,360,000 A | 11/1994 | Carter |
| 5,368,022 A | 11/1994 | Wagner |
| 5,370,112 A | 12/1994 | Perkins |
| 5,386,824 A | 2/1995 | Nelepka |
| 5,398,676 A | 3/1995 | Press et al. |
| 5,411,059 A | 5/1995 | Sever et al. |
| 5,413,096 A | 5/1995 | Hart |
| 5,415,161 A | 5/1995 | Ryder |
| 5,438,980 A | 8/1995 | Phillips |
| 5,443,062 A | 8/1995 | Hayes |
| 5,478,046 A | 12/1995 | Szabo |
| 5,485,983 A | 1/1996 | Voege et al. |
| 5,495,848 A | 3/1996 | Aylsworth et al. |
| 5,503,146 A | 4/1996 | Froehlich et al. |
| 5,522,382 A | 6/1996 | Sullivan et al. |
| 5,531,679 A | 7/1996 | Schulman et al. |
| 5,544,858 A | 8/1996 | Rogers et al. |
| 5,546,985 A | 8/1996 | Bartholomew |
| 5,549,106 A | 8/1996 | Gruenke et al. |
| 5,551,419 A | 9/1996 | Froehlich et al. |
| 5,558,086 A | 9/1996 | Smith et al. |
| 5,570,682 A | 11/1996 | Johnson |
| 5,596,984 A | 1/1997 | O'Mahony et al. |
| 5,603,315 A | 2/1997 | Sasso, Jr. |
| 5,651,361 A | 7/1997 | Dearman et al. |
| 5,666,945 A | 9/1997 | Davenport |
| 5,685,297 A | 11/1997 | Schuler |
| 5,701,889 A | 12/1997 | Danon |
| 5,752,544 A | 5/1998 | Yves |
| 5,755,224 A | 5/1998 | Good et al. |
| 5,785,050 A | 7/1998 | Davidson et al. |
| 5,881,725 A | 3/1999 | Hoffman et al. |
| 5,899,223 A | 5/1999 | Shuman, Jr. |
| 5,928,189 A | 7/1999 | Phillips et al. |
| 6,009,900 A | 1/2000 | Elgert et al. |
| 6,053,056 A | 4/2000 | Zaiser et al. |
| 6,082,359 A | 7/2000 | Preston |
| 6,082,396 A | 7/2000 | Davidson |
| 6,089,259 A | 7/2000 | Shuman, Jr. |
| 6,116,242 A | 9/2000 | Frye et al. |
| 6,137,417 A | 10/2000 | McDermott |
| 6,155,258 A | 12/2000 | Voege |
| 6,158,457 A | 12/2000 | Byrd et al. |
| 6,189,531 B1 | 2/2001 | Tatarek |
| 6,240,943 B1 | 6/2001 | Smith |
| 6,273,130 B1 | 8/2001 | Cossins |
| 6,286,543 B1 | 9/2001 | Davidson |
| 6,321,779 B1 | 11/2001 | Miller et al. |
| 6,325,097 B1 | 12/2001 | Gallant et al. |
| 6,354,564 B1 | 3/2002 | Van Scyoc et al. |
| 6,364,161 B1 | 4/2002 | Pryor |
| 6,382,589 B1 | 5/2002 | Edstrom, Sr. et al. |

| | | | |
|---|---|---|---|
| 6,386,235 B1 | 5/2002 | McCulloh et al. | |
| 6,401,714 B1 | 6/2002 | Giorgini | |
| 6,401,740 B2 | 6/2002 | Zaiser | |
| 6,467,325 B1 | 10/2002 | Zaiser | |
| 6,484,720 B1 | 11/2002 | Marquard, II et al. | |
| 6,484,721 B1 | 11/2002 | Bliss | |
| 6,510,747 B1 | 1/2003 | Zaiser | |
| 6,532,958 B1 | 3/2003 | Buan et al. | |
| 6,568,391 B1 | 5/2003 | Tatarek et al. | |
| 6,575,430 B1 | 6/2003 | Smith, III | |
| 6,581,592 B1 | 6/2003 | Bathe et al. | |
| 6,612,307 B2 | 9/2003 | Byrd | |
| 6,647,982 B1 | 11/2003 | Zaiser et al. | |
| 6,752,152 B2 | 6/2004 | Gale et al. | |
| 6,772,762 B2 | 8/2004 | Piesinger | |
| 2002/0073998 A1 | 6/2002 | Byrd | |
| 2003/0075179 A1 | 4/2003 | Gale et al. | |
| 2003/0150455 A1 | 8/2003 | Bliss et al. | |
| 2005/0192538 A1 | 9/2005 | Voege et al. | |

FOREIGN PATENT DOCUMENTS

| | | |
|---|---|---|
| DE | 3329954 | 3/1985 |
| DE | 43 12 510 | 10/1993 |
| EP | 0 217 573 | 4/1992 |
| EP | 0 283 141 | 9/1995 |
| EP | 1 028 770 | 8/2000 |
| GB | 497113 | 12/1938 |
| GB | 2 170 409 A | 8/1986 |
| JP | 3-90164 | 4/1991 |
| JP | 5-92038 | 4/1993 |
| JP | 6-197967 | 7/1994 |
| JP | 6-205833 | 7/1994 |
| JP | 6-315533 | 11/1994 |
| JP | 8-19615 | 1/1996 |
| JP | 8-173539 | 7/1996 |
| WO | WO 87/02590 | 5/1987 |
| WO | WO 87/06142 | 10/1987 |
| WO | WO 95/23624 | 9/1995 |
| WO | WO 96/40336 | 12/1996 |
| WO | WO 97/06844 | 2/1997 |
| WO | WO 99/22795 | 5/1999 |

OTHER PUBLICATIONS

Precision Medical—Easy Pulse Oxygen Conserving Regulator, © 2002 Precision Medical, Inc., 1 pg.
Precision Medical—Easy Pulse Oxygen Conserver Specifications, © 2002 Precision Medical, Inc., 1 pg.
Precision Medical—Dial Flowmeters, © 2002 Precision Medical, Inc., 1 pg.
Precision Medical—Chrome Body Series Flowmeters, © 2002 Precision Medical, Inc., 1 pg.
Precision Medical—Pediatric Flowmeters, © 2002 Precision Medical, Inc., 1 pg.
Precision Medical—Select Flowmeters, © 2002 Precision Medical, Inc., 1 pg.
Precision Medical—Easy Regulators, © 2002 Precision Medical, Inc., 1 pg.
Precision Medical—Easy Dial Regulators, © 2002 Precision Medical, Inc., 1 pg.
Precision Medical—Easy Guage Regulators, © 2002 Precision Medical, Inc., 1 pg.
Precision Medical—Easy Meter Regulators, © 2002 Precision Medical, Inc., 1 pg.
Inovo Oxygen Regulators, retrieved from www.life-assist.com/inovo.html, Apr. 20, 2004, 4 pgs.
Vernay® Umbrella Check Valves brochure, Vernay Laboratories, Inc., May 9, 2003, 4 pgs.
Vernay Laboratories—Umbrella Check Valves, retrieved from www.vernay.com/products/umbrella.htm, Dec. 23, 2003, 5 pgs.
Vernay Laboratories, Inc.—A custom molded rubber products manufacturer with worldwide locations, www.vernay.com/products/diaphram.htm, Dec. 23, 2003, 3 pgs.
U.S. Statutory Invention Registration No. H1282, published Feb. 1, 1994, to Joyce et al.
Auerbach, et al., "A New Oxygen Cannula System Using Intermittent-Demand Nasal Flow," Chest, 74:1, pp. 39-44, Jul. 1978.
Sabre Medical Elite description, http://www.gceuk.com/saber/domicillary_products/elite.html, Oct. 24, 2005, 1 pg.
Sabre Medical Elite Datasheet, Nov. 30, 2004, 1 pg.
Sabre Medical Elite QF Datasheet, Nov. 30, 2004, 1 pg.
Sabre Medical Integra Datasheet, Nov. 30, 2004, 1 pg.
Sabre Medical Portaflow description, http://www.gceuk.com/saber/domicillary_products/portaflow.html, Oct. 24, 2005, 1 pg.
Sabre Medical, Medical Gas Regulators, Nov. 30, 2004, 2 pages.
Photographs—Device A available from Ameriflo prior to Feb. 25, 2004, 1 pg.
Photographs—Device B available from Ameriflo prior to Oct. 20, 2004, 1 pg.
Torregroza, M., Oxygen application with the pulse air oxygen delivery system compact station, European Respiratory Journal Supplement 9 (23), 1996, p. 443S, Stockholm, Sweden, (bibliographic information).
Momoeda, K., Oropharyngeal oxygen concentration using twin nasal oxygen cannulae with compression—a comparison with conventional devices, Anesthesiology (Hagerstown)85 (3A), p. A447, 1996, (bibliographic information).
Tiep, B., Portable oxygen therapy with oxygen conserving devices and methodologies, IRCCS and Istituto di Clinica Tisiologica e Malattie Apparato Respiratorio, Univer, Jan. 1995, 50, p. 51-7, Italy, (abstract only).
Lin Cai Yuan, Clinical evaluation of pulse-dose and continuous-flow oxygen delivery, Respiratory Care, 1995, 40/8 p. 811-814, U.S., (abstract only).
Krause-Michel, B., Improvement of compliance in long-term oxygen therapy by eyeglasses with integrated single nasal cannula for oxygen supply, Atemwegs-und Lungenkrankheiten 21 (10), p. 516-517, 1995, Germany, (abstract only).
Tehrani, F. T., A feedback controller for supplemental oxygen treatment of newborn infants: a simulation study, Medical Engineering & Physics, Jul. 1994, 16(4), p. 329-33, England, (abstract only).
Yaeger, E. S., Oxygen therapy using pulse and continuous flow with a transtracheal catheter and a nasal cannula, Chest, Sep. 1994, 106(3), p. 854-60, U.S., (abstract only).
Hoffman, L. A., Novel strategies for delivering oxygen: reservoir cannula, demand flow, and transtracheal oxygen administration, Respiratory Care, Apr. 1994, 39 (4), p. 363-77, discussion 386-9, U.S., (abstract only).
Fitzgerald, D. J., Variance of oxygen with nasal cannula and transtracheal delivery systems, American Review Of Respiratory Disease, V147, N4, Apr. 1993, p. A976, (bibliographic information).
Tiep, B., Oxygen conserving devices in obstructive and restrictive disease, Atemwegs-und Lungenkrankheiten 18/Suppl. 2, p. S142-S149, 1992, Germany, (bibliographic information).
Vilsvik, J.,. Oxygen-conserving nasal cannula: Oxymizer pendant, Tidsskrift for den Norske Laegeforening 112(29), p. 3659-3662, 1992, Norway, (abstract only).
Ishihara, T., Oxygen-conserving delivery system, Nihon Kyobu Shikkan Gakkai zasshi, 30 Suppl., Dec. 1992, p. 156-63, Japan, (abstract only).
Hoffman, L. A., Nasal cannula and transtracheal oxygen delivery. A comparison of patient response after 6 months of each technique, American Review of Respiratory Disease 145 (4 Pt 1), Apr. 1992, p. 827-31, U.S., (abstract only).
Monasterio, C., The evaluation of the oxygen-conserving valve during exertion, Medicina Clinica 98 (4), p. 128-30, Feb. 1, 1992, Spain, (abstract only).
Haber, H., Comparison of an oxygen-conserving module 'Oxytron' and the reservoir cannula 'Oxymizer Pendant' with continuous oxygen administration via nasal prong in hypoxemic patients, Wiener Klinische Wochenschrift 102 (11), May 25, 1990, p. 325-9, ISSN 0043-5325, Journal Code: 21620870R, Austria, (abstract only).
Kerby, G. R., Clinical efficacy and cost benefit of pulse flow oxygen in hospitalized patients, Chest 97 (2), Feb. 1990, p. 369-72, U.S., (abstract only).

Moore-Gillon, J., Oxygen-conserving delivery devices, Respiratory Medicine 83 (4), Jul. 1989, p. 263-4, England, (bibliographic information).

Rousseau, M., Oxygen delivery via nasal cannula how much oxygen are we actually delivering, Anesthesiology (Hagerstown) 71 (3A), 1989, p. A354, (bibliographic information).

Senn, S., Efficacy of a pulsed oxygen delivery device during exercise in patients with chronic respiratory disease, Chest 96(3), Sep. 1989, p. 467-72, ISSN 0012-3692, U.S., (abstract only).

Taube, J.C., Criteria for an adaptive fractional inspired oxygen controller, Computer-Based Medical Systems (Cat. No. 88CH2606-2), IEEE Comput. Soc. Press, Washington, DC, 1988, p. 129-32, (abstract only).

Leger, P., Oxygen-conserving devices for delivery of long-term oxygen therapy, Agressologie-Revue Intenationale De Physio-Biologie Et De Pharmacologie Appliquees Aux Effets De L'agression 29 (8), Sep. 1988, p. 603-6, France, (bibliographic information).

Romberger, D. J., Comparison of continuous and pulse flow oxygen in hospital patients, American Review of Respiratory Disease 137 (4 Part 2), p. 158, 1988, U.S., (bibliographic information).

Brown, C. C., Reservoir nasal cannula prevents oxygen desaturation in copd patients during eating, American Review of Respiratory Disease 137 (4 Part 2), p. 157, 1988, U.S., (bibliographic information).

Strezelecki, L. R., Comparison of demand oxygen controlled and continuous flow oxygen in an intubated model, Chest 94 (1 Suppl), p. 91S, 1988, U.S., (bibliographic information).

Hayhurst. M. D., A new long-flow oxygen-conserving cannula, South African Medical Journal 71 (4), Feb. 21, 1987, p. 251-2, South Africa, (abstract only).

Evans, T.W., An oxygen conservation device in patients with corpulmonale—an unsustained effect, Thorax, V42, N3, p. 216, 1987, England, (bibliographic information).

Claiborne, R. A., Evaluation of the use of an oxygen conservation device in long-term oxygen therapy, American Review of Respiratory Disease 136 (5), p. 1095-8, U.S., (abstract only).

Tiep, B., Oxygen conservation and oxygen-conserving devices in chronic lung disease. A review, Chest 92 (2), Aug. 1987, p. 263-72, U.S., (abstract only).

Tremper, J. C., Reliability of the oxymatic electronic oxygen conserver, American Review of Respiratory Disease 135 (4 Part 2), 1987, p. A194, U.S., (bibliographic information).

Gould, G. A., Comparison of two oxygen conserving nasal prong systems and the effects of nose and mouth breathing, Thorax 41 (10), Oct. 1986, p. 808-9, England, (bibliographic information).

Pesce, L., Usefulness of new oxygen conserving delivery device in 10 patients affected by respiratory failure, Giornale Italiano delle Malattie del Torace 40 (6), 1986, p. 427-429, Italy, (abstract only).

Carter, R., Evaluation of the pendant oxygen-conserving nasal cannula during exercise, Chest 89 (6), Jun. 1986, p. 806-10, U.S., (abstract only).

Leger, P., Simultaneous use of a pulsed dose demand valve with a transtracheal catheter an optimal oxygen saving for long-term oxygen therapy, American Review of Respiratory Disease 133 (4 Suppl), 1986, p. A350, U.S., (bibliographic information).

Moore-Gillon, J.C., An oxygen conserving nasal cannula, Thorax 40 (11), Nov. 1985, p. 817-9, England, (abstract only).

Soffer, M., Conservation of oxygen supply using a reservoir nasal cannula in hypoxemic patients at rest and during exercise, Chest 88 (5), Nov. 1985, p. 663-8, U.S., (abstract only).

Tiep, B.L., A new pendant storage oxygen-conserving nasal cannula, Chest 87 (3), Mar. 1985, p. 381-3, U.S., (abstract only).

Shigeoka, J.W., The current status of oxygen-conserving devices, Respiratory Care 30/10, 1985, 833-836, U.S., (bibliographic information).

Gould, G.A., Clinical assessment of oxygen conserving devices in chronic bronchitis and emphysema, Thorax 40 (11), Nov. 1985, p. 820-4, England, (abstract only).

Zwischenberger, J. B., Total respiratory support with single cannula venovenous ECMO: double lumen continuous flow vs. single lumen tidal flow, Transactions—American Society for Artificial Internal Organs 31, 1985, p. 610-5, U.S., (bibliographic information).

Tiep, B.L., Evaluation of a low-flow oxygen-conserving nasal cannula, American Review of Respiratory Disease 130 (3), Sep. 1984, p. 500-2, U.S., (abstract only).

Tiep, B.L., A new oxygen saving nasal cannula, American Review of Respiratory Disease 127 (4 Part 2), 1983, p. 86, U.S., (bibliographic information).

* cited by examiner

FLUID REGULATOR

RELATED APPLICATIONS

This application claims the benefit of U.S. Provisional Patent Application Ser. No. 60/620,890, titled FLUID REGULATOR, filed Oct. 21, 2004, the disclosure of which is expressly incorporated by reference herein.

BACKGROUND AND SUMMARY OF THE INVENTION

The present invention relates to fluid regulators and in particular to fluid regulators for use in the delivery of medical fluids.

Fluid regulators are known in the medical area for the delivery of a medical gas, such as oxygen, to a patient. Exemplary fluid regulators are capable of providing multiple calibrated flow rates from a source of pressurized fluid to a cannula or other device for output to a patient.

In an exemplary embodiment, a fluid regulator is provided. The fluid regulator comprising a cylindrical body including a first portion configured to be coupled to a source of high pressure fluid and a second portion configured to be coupled to a cannula. The first portion including a fluid inlet and the second portion including a fluid outlet in fluid communication with the fluid inlet. The cylindrical body having an open end and a reduced diameter portion adjacent the open end. The fluid regulator further comprising a flow restrictor having at least a first fluid passage configured to provide a first restricted flow rate of fluid and a second fluid passage configured to provide a second restricted flow rate of fluid. The flow restrictor being received in the open end of the cylindrical body portion and moveable relative to the body portion so that one of the first fluid passage and the second fluid passage is selectively interposed between the fluid inlet of the body and the fluid outlet of the body to restrict the flow rate of fluid from the fluid inlet of the body to the fluid outlet of the body. The fluid regulator further comprising a flow selector coupled to the flow restrictor and positioned adjacent the open end of the cylindrical body portion. The flow selector including a first portion having a diameter larger than a diameter of the reduced diameter portion of the cylindrical body. In one example, a longitudinal extent of the reduced diameter portion of the cylindrical body is about 7 percent of an overall length of the cylindrical body. In another example, a longitudinal extent of the reduced diameter portion of the cylindrical body is about 0.25 inches. In a further example, the reduced diameter portion of the cylindrical body includes a window positioned so that a portion of a second portion of the flow selector is visible therethrough, the second portion of the flow selector being positioned within the open end of the cylindrical body, the visible portion of the second portion of the flow selector including an indicia indicating a flow rate of the one of the first fluid passage and the second fluid passage is selectively interposed between the fluid inlet of the body and the fluid outlet of the body. In still a further example, the cylindrical body includes a first diameter larger than the reduced diameter portion and the diameter of the first portion of the flow selector is substantially equal to the first diameter of the cylindrical body. In yet a further example, the fluid regulator further comprises a pressure reduction section being received in the open end of the body and positioned between the fluid inlet of the body and the flow restrictor, the pressure reduction section being configured to receive fluid at a first pressure from the fluid inlet and to provide fluid at a lower pressure to the flow restrictor; and a housing positioned within the open end of the body, the housing including a recess into which the flow selector and the pressure reduction section are positioned and a fluid conduit which is aligned with the fluid outlet of the body and selectively aligned with a respective fluid passage of the flow restrictor. In a variation, the housing is coupled to the body with a coupler which extends into the housing from an exterior of the body.

In another exemplary embodiment, a fluid regulator is provided. The fluid regulator comprising a body having an interior cavity accessible through an open end, a fluid inlet which is configured to receive a high pressure fluid from a source of pressurized fluid, and a fluid outlet. The fluid regulator further comprising a housing positioned in the interior cavity of the body. The housing including an interior cavity accessible from an open end of the housing, a fluid inlet accessible through the open end of the housing which is in fluid communication with the fluid inlet of the body and a fluid outlet in fluid communication with the fluid inlet of the housing and the fluid outlet of the body. The fluid regulator further comprising a pressure reduction section positioned within the interior cavity of the housing through the open end of the housing, the pressure reduction section being configured to receive the high pressure fluid from the fluid inlet of the body and to provide a lower pressure fluid to the fluid inlet of the housing. The pressure reduction section including: a base member including a base portion and a guide portion extending from the base portion, the base member having a central passageway extending there through, the central passageway being positioned such that it is in fluid communication with the fluid inlet of the body; a piston including a piston base portion and a stem portion, the stem portion being configured to be received by the central passageway in the guide portion of the base member, the piston having a fluid passageway there through with a fluid inlet in the stem portion and a fluid outlet in the piston base portion, the fluid outlet being in fluid communication with the fluid inlet of the housing; and a biasing member sized to receive the guide portion of the base member, a first end of the biasing member being positioned adjacent the base portion of the base member and a second end of the biasing member being positioned adjacent a seat surface of the piston base portion, the seat surface being located in a recess formed in the piston base portion, the recess being sized to receive a first end of the guide portion of the base member. The fluid regulator further comprising a rotatable flow restrictor including a flow control portion disposed within the interior cavity of the housing and a stem portion coupled to the disk portion and extending through an aperture connecting the cavity of the housing and a second end of the housing, the flow control portion including a plurality of fluid conduits each selectively being brought into fluid communication with the fluid conduit of the housing through the rotation of the flow restrictor relative to the housing. In an example, the flow control portion of the flow restrictor includes a first axial surface containing the respective fluid outlets for each of the plurality of fluid conduits of the flow restrictor, a second axial surface including the respective fluid inlets for each of the plurality of fluid conduits of the flow restrictor, and a radial surface disposed between the first axial surface and the second axial surface, the radial surface including openings sized to receive respective occluders which are advanced into the respective fluid conduit to reduce a cross-sectional area of the respective fluid conduit of the flow restrictor. In another example, the flow control portion of the flow restrictor includes a first axial surface including the respective fluid outlets for each of the plurality of fluid conduits of the flow restrictor, a second axial surface including the respective fluid inlets for each of the plurality of fluid conduits of the flow restrictor, and a radial surface disposed between the first axial surface and the second axial surface, the radial surface including openings sized to receive respective occluders which are advanced into the respective fluid conduit to reduce a cross-sectional area of the respective fluid conduit of the flow restrictor. In a further example, the flow control portion of the flow restrictor includes a first axial surface including the respective fluid inlets for each of the plurality of fluid conduits of the flow restrictor, a second axial surface including openings sized to receive respective occluders which are advanced into the respective fluid conduit to reduce a cross-sectional area of the respective fluid conduit of the flow restrictor, and a radial surface disposed between the first axial surface and the second axial surface including the respective fluid outlets for each of the plurality of fluid conduits of the flow restrictor. In still a further example, the body is generally cylindrical having a first diameter and a reduced diameter portion, the reduced diameter portion being adjacent the open end. In a variation, the fluid regulator further comprises a flow selector coupled to the flow restrictor, the flow restrictor being positioned adjacent the open end of the cylindrical body such that a first portion of the flow selector is received in the open end of the cylindrical body and a second portion of the flow selector extends beyond the open end of the cylindrical body, the second portion of the flow selector having a diameter larger than the diameter of the reduced diameter portion. In yet a further example, the fluid regulator further comprises a hose barb which is coupled to the fluid outlet of the body and extends into the housing. In a variation the hose barb restrain the rotational movement of the housing relative to the body. In yet still a further example, the longitudinal movement of the housing within the open end of the body is limited by a coupler which is received within a recess of the interior cavity of the body, the coupler contacting a top portion of the housing. In yet still another example, the housing is coupled to the body with a coupler which extends into the housing from an exterior of the body.

In a further exemplary embodiment, a method of reducing the pressure of a fluid introduced through a fluid inlet of a body of a fluid regulator, the fluid inlet being located in an interior cavity of the body accessible through an open end of the body of the fluid regulator is provided. The method comprising the steps of: positioning a housing having an interior cavity accessible through an open end and a fluid conduit, the interior cavity having a stop surface, the fluid conduit having a fluid inlet in an axial surface of the interior cavity and a fluid outlet in an external radial surface of the housing; coupling a flow restrictor having a plurality of fluid conduits each having a respective flow rate, the flow restrictor being rotatable relative to the housing to permit each fluid conduit to be selectively brought into fluid communication with the fluid conduit of the housing through the rotation of the flow restrictor relative to the housing; positioning a pressure reduction section between the fluid inlet and the flow restrictor, the pressure reduction section including a base member, a piston, and a biasing member. The base member includes a base portion and a guide portion extending from the base portion, the base member having a central passageway extending there through, the central passageway being positioned such that it is in fluid communication with the fluid inlet of the body. The piston includes a piston base portion and a stem portion, the stem portion being configured to be received by the central passageway in the guide portion of the base member, the piston having a fluid passageway there through with a fluid inlet in the stem portion and a fluid outlet in the piston base portion, the fluid outlet being in fluid communication with the flow restrictor. The biasing member sized to receive the guide portion of the base member, a first end of the biasing member being positioned adjacent the base portion of the base member and a second end of the biasing member being positioned adjacent a seat surface of the piston base portion. The seat surface being located in a recess of the piston base portion. The recess being sized to receive a first end of the guide portion of the base member. The method further comprising the steps of positioning the pressure reduction section in the interior cavity of the housing, a rear side of the piston of the pressure reduction section being positioned adjacent the stop surface of the interior cavity of the housing; positioning the housing in the interior cavity of the body; coupling the housing to the body; passing fluid from the fluid inlet of the body through the central passageway of the guide portion of the base member into a fluid conduit of the piston which includes a transverse conduit in the stem portion of the piston in fluid communication with the central passageway of the base member and a longitudinal conduit in the stem portion of the piston in fluid communication with the transverse conduit of the stem portion and a rear side of the piston resulting in an increase in the fluid pressure adjacent the rear side of the piston in a space between the piston and the flow restrictor; permitting the movement of the piston in a direction away from the flow restrictor as the pressure in the space increases, the stem portion of the piston being further advanced into the guide portion of the base member; and receiving the guide portion of the base member in the recess of the piston as the piston moves in the direction away from the flow restrictor. In an example, the flow restrictor is rotated to a position wherein fluid is prevented from entering the fluid inlet of the housing resulting in the pressure of fluid in the space between the piston and the flow restrictor increasing and the piston moving further in the direction away from the flow restrictor until a seal coupled to an end of the stem portion contacts the fluid inlet of the body. In another example, the step of coupling the housing to the body includes the steps of: coupling a hose barb to the fluid outlet of the body; and extending a portion of hose barb into the fluid outlet of the housing. In a variation the step of coupling the housing to the body further includes the step of locating a retainer in a recess of the interior cavity of the body, the retainer contacting a top portion of the housing.

DETAILED DESCRIPTION OF THE DRAWINGS

Figure 1B:
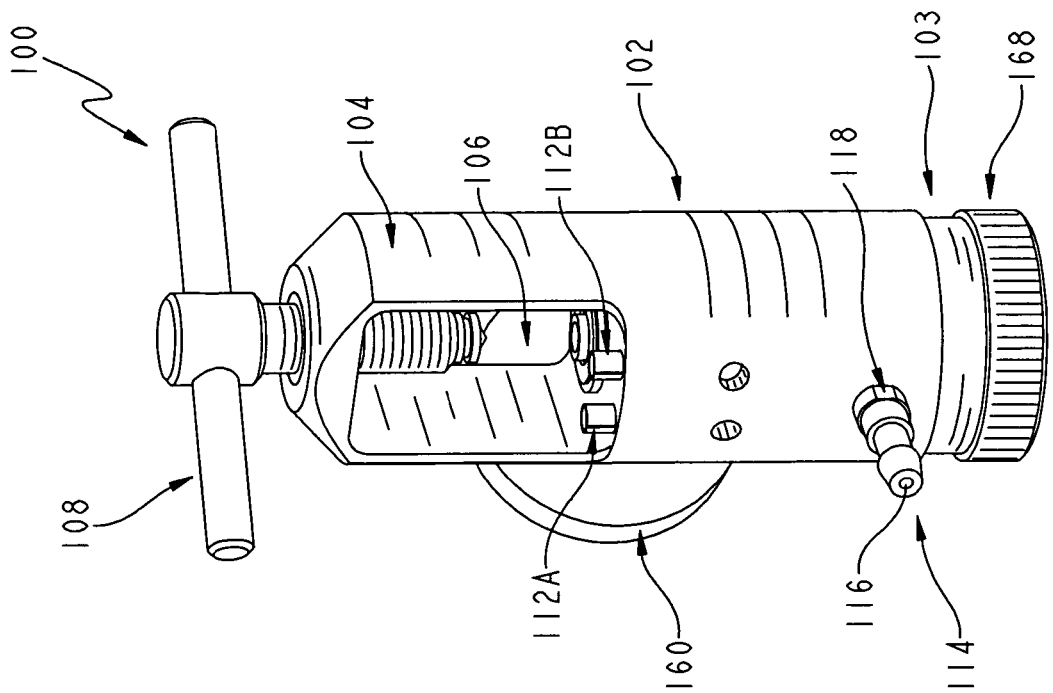
FIG. 1B is a back perspective view of the fluid regulator of FIG. 1A.
Figure 1A:
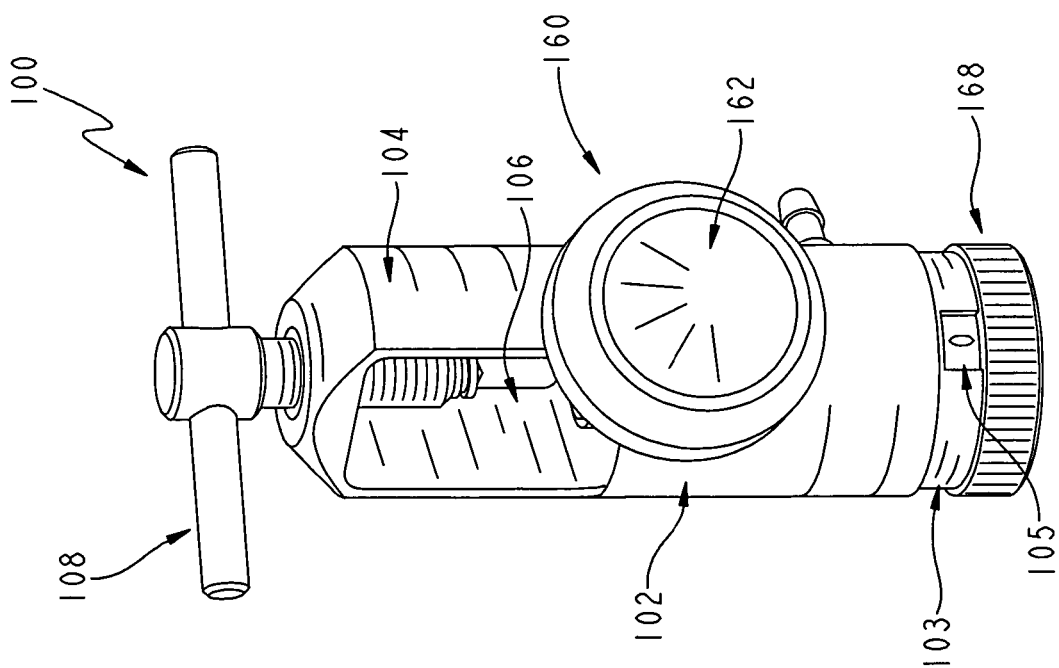
FIG. 1A is a front perspective view of a fluid regulator.

Referring to FIGS. 1A and 1B an exemplary fluid regulator 100 is shown. Fluid regulator 100 includes a body portion 102 having a yoke portion 104 which couples to a post valve (not shown) of a source of pressurized fluid, such as oxygen. The post valve of the source of pressurized fluid is received in opening 106 and urged by retainer 108 such that a fluid inlet 110 of flow regulator 100 is brought into fluid communication with a fluid outlet of the source of pressurized fluid. Retainer 108 is shown as a T-handle which is threadably received by yoke portion 104 of fluid regulator 100. In alternative embodiment, retainer 108 is a set screw or other device which cannot be easily manipulated to permit the uncoupling of fluid regulator 100 from the source of pressurized fluid. In other alternative embodiments, yoke 104 and retainer 108 is replaced with a nut & nupple connection to the source of pressurized fluid.

Also shown are two alignment members 112A and 112B which are received by mating alignment features on the post valve of the source of pressurized fluid and thus assist in aligning fluid regulator 100 relative to the post valve of the source of pressurized fluid. In one example, alignment members 112a and 112b are made of stainless steel and protrude into opening 106.

Fluid from the source of pressurized fluid is typically at a pressure of between about 500 psi (pounds per square inch) and about 3000 psi. As explained in more detail below fluid regulator 100 receives this high pressure fluid from the source of pressurized fluid and presents a selectable lower pressure fluid to an output device through a fluid outlet 114 to an application device. Fluid outlet 114 is shown as a fluid conduit 116 (see FIG. 1B) in a hose barb 118. Exemplary application devices include a cannula, other fluid conduits, or fluid conserving devices.

Figure 2:
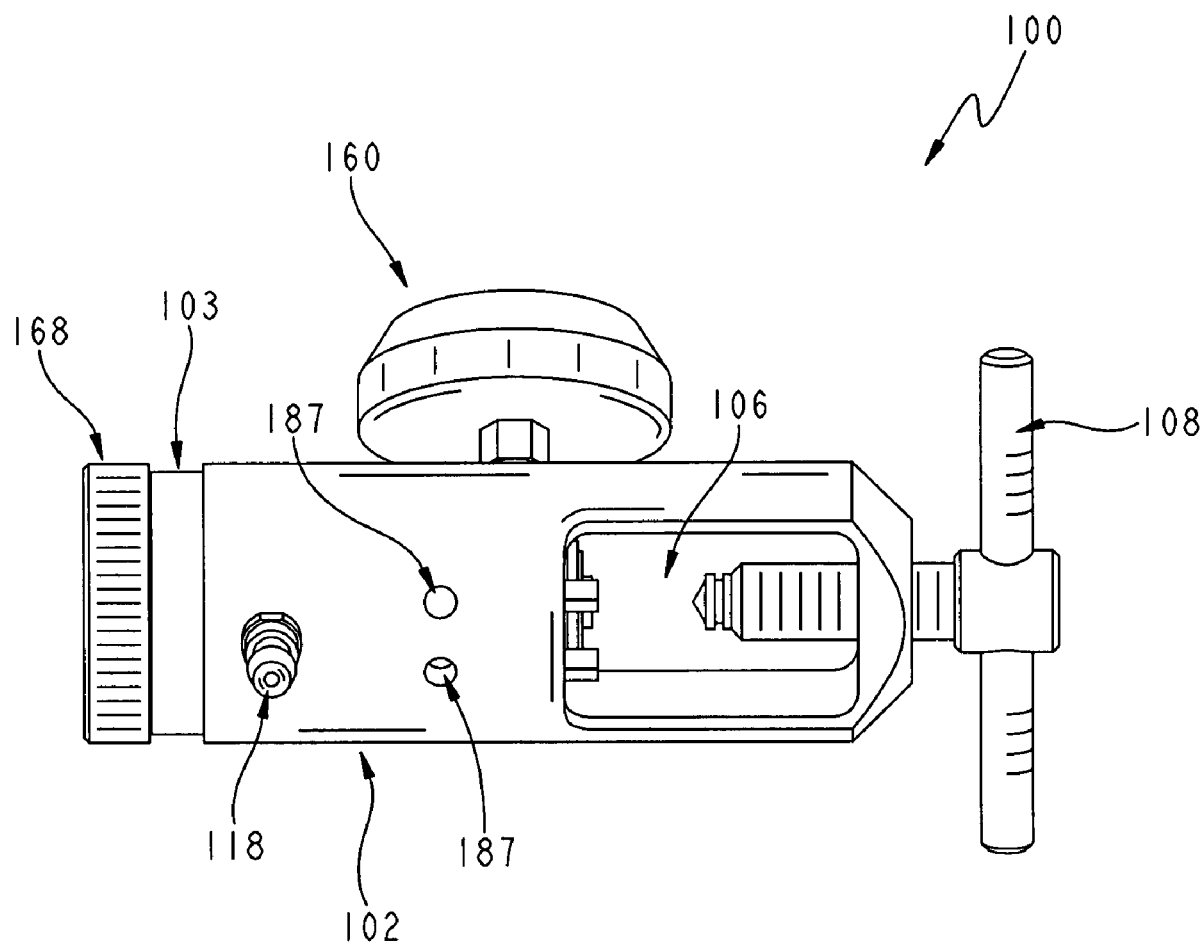
FIG. 2 is a perspective view of the fluid regulator of FIG. 1A.
Figure 3:
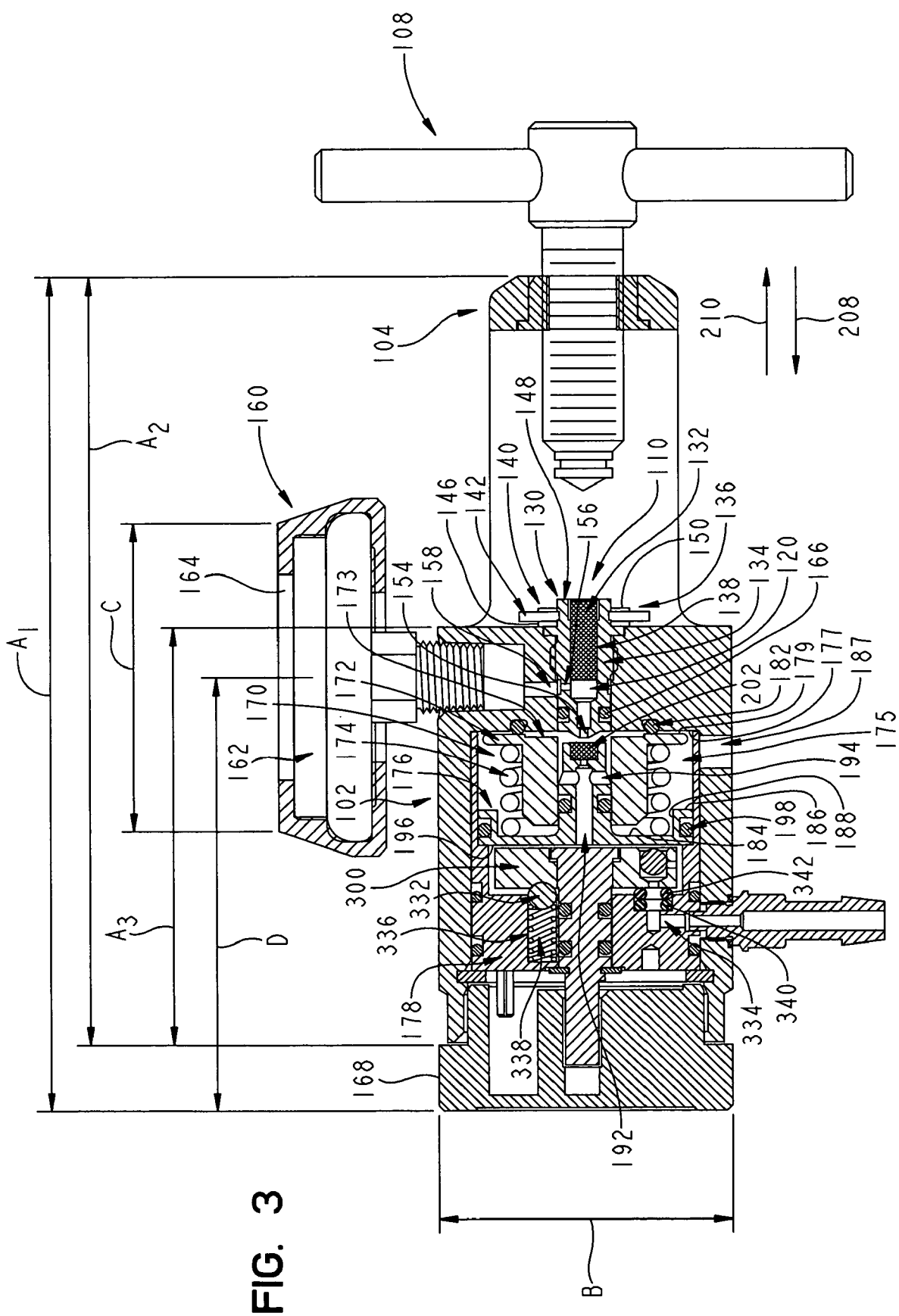
FIG. 3 is a schematic view of the fluid regulator of FIG. 2.

Referring to all the figures of the application, and in particular FIGS. 1A, 1B, and 2, flow regulator 100 is generally more compact than existing flow regulators. Referring to FIG. 3, in one preferred embodiment, an overall length $A_1$ of flow regulator 100 is up to about 3 times a diameter B of body portion 102 of flow regulator 100. In one example, overall length $A_1$ is about 3.96 inches and diameter B of body portion 102 of flow regulator 100 is about 1.365 inches which corresponds to a ratio of 2.9. In another preferred embodiment, a length $A_2$ of body portion 102 is up to about 2.7 times diameter B of flow regulator 100, and/or a length $A_2$ of body portion 102 is up to about 0.9 times the overall length $A_1$ of flow regulator 100. In one example, overall length $A_1$ is about 3.96 inches, length $A_2$ is about 3.638 inches, and diameter B of body portion 102 of flow regulator 100 is about 1.365 inches. As such, the ratio of $A_2$ to $A_1$ is about 0.92 and the ratio of $A_2$ to B is about 2.66. In a further preferred embodiment, a length $A_3$ of body portion 102 from yoke portion 104 to an end of body portion 102 is up to about 1.4 times diameter B and/or a length $A_3$ of body portion 102 is up to about 0.5 times the overall length $A_1$ of flow regulator 100. In one example, overall length $A_1$ is about 3.96 inches, length $A_2$ is about 3.638 inches, length $A_3$ is about 1.973 inches, and diameter B of body portion 102 of flow regulator 100 is about 1.365 inches. As such, the ratio of $A_3$ to $A_1$ is about 0.498, the ratio of $A_3$ to $A_2$ is about 0.542, and the ratio of $A_2$ to B is about 1.45.

Further, in one embodiment, a diameter C (front face) of gauge 160 is at least about 0.37 times the length $A_1$ of flow regulator 100 and/or gauge 160 is centered up to about 0.48 percent of length $A_2$ from the end of body 102 which receives flow selector 168. In one example, C is about 1.45 inches and $A_1$ is about 3.96 inches resulting in a ratio of about 0.366 and gauge 160 is centered a distance of 1.736 from the end of body 102, the body having a length $A_2$ of 3.638 inches, resulting in about 0.477 percent.

Figure 19:
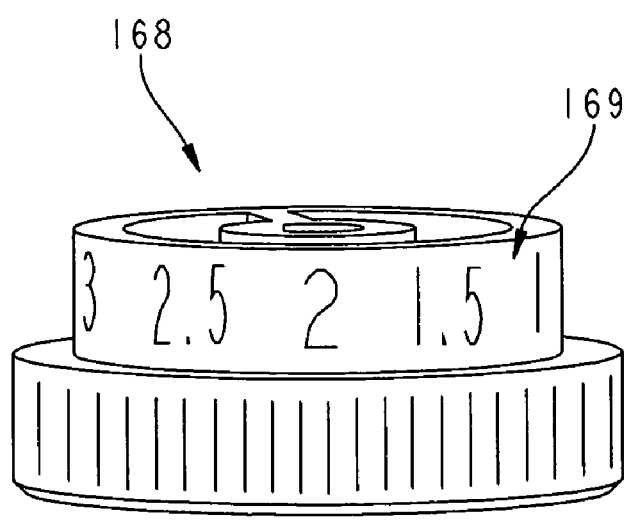
FIG. 19 is a side view of the flow selector of FIG. 18.
Figure 20:
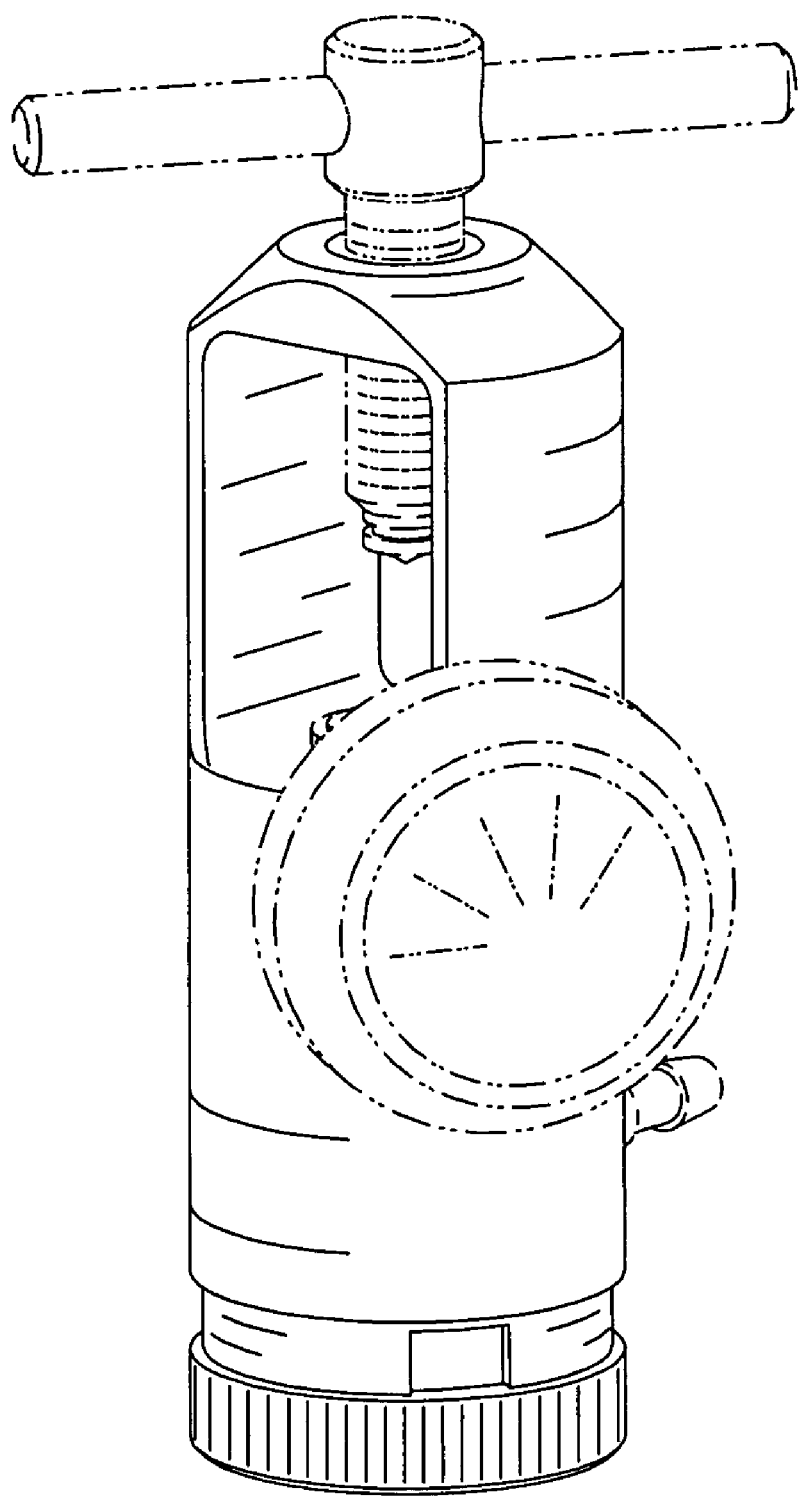
FIG. 20 is a first perspective view of the flow regulator of FIG. 1 shown at a scale of 1.25.
Figure 21:
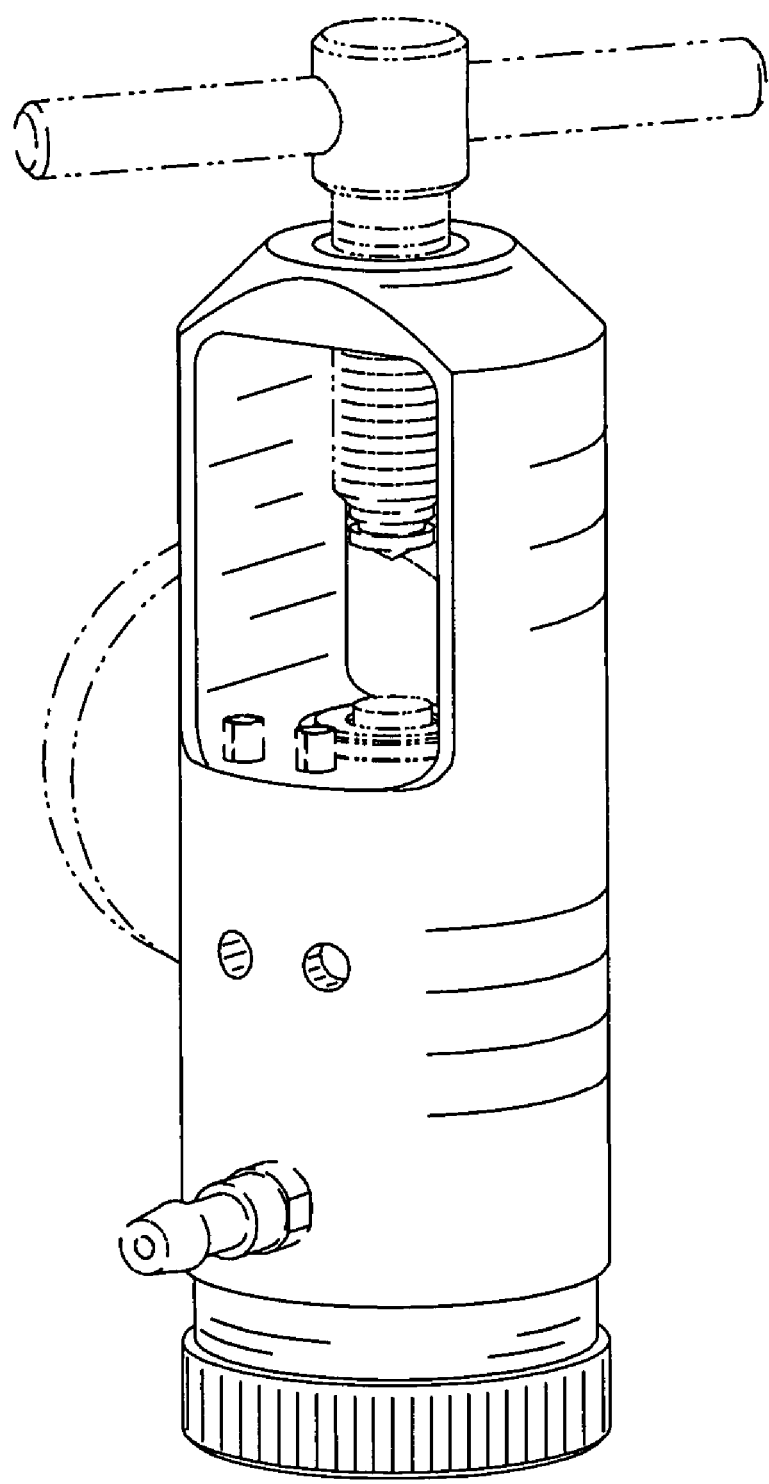
FIG. 21 is a second perspective view of the flow regulator of FIG. 20.
Figure 22:
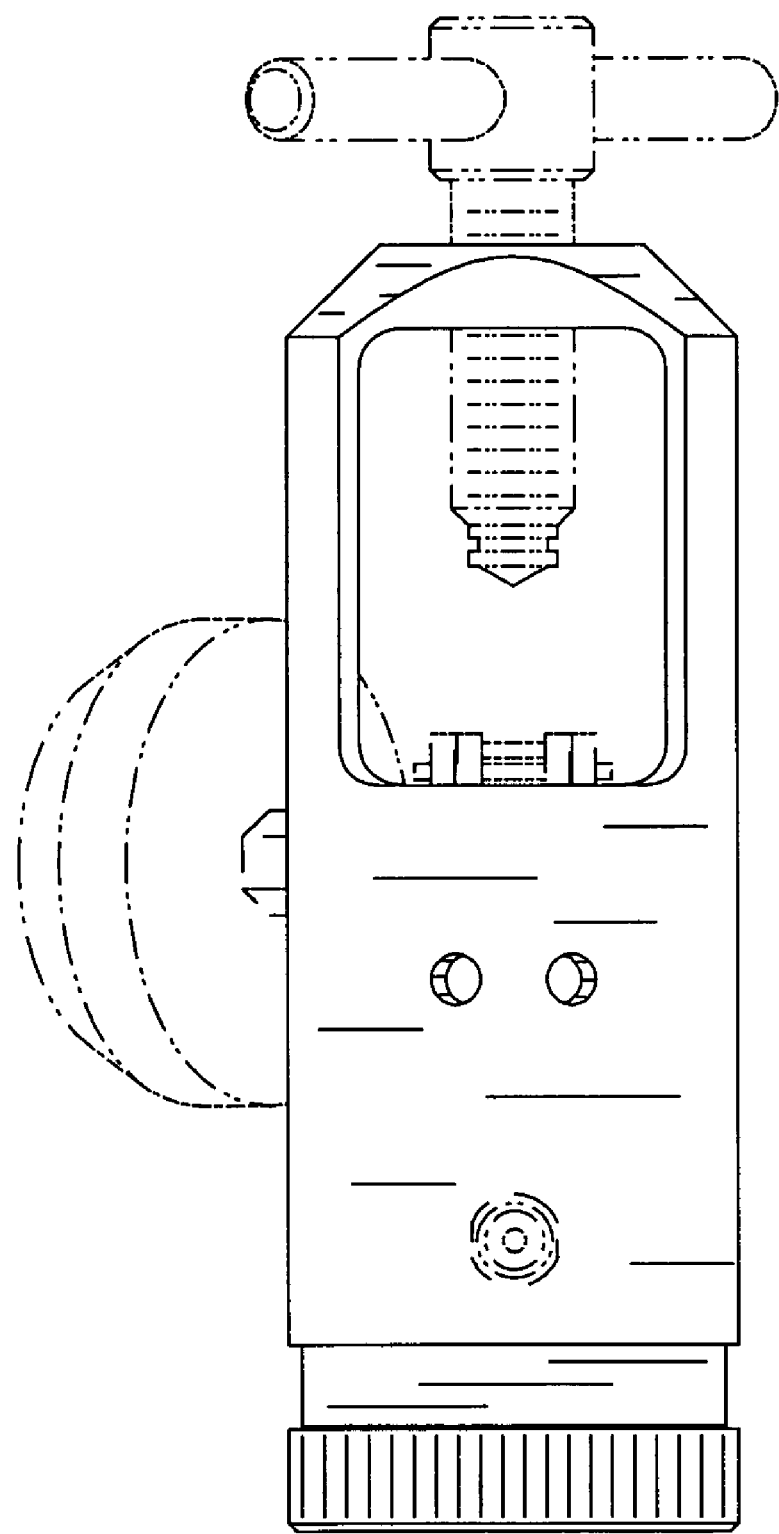
FIG. 22 is back view of the flow regulator of FIG. 20.
Figure 23:
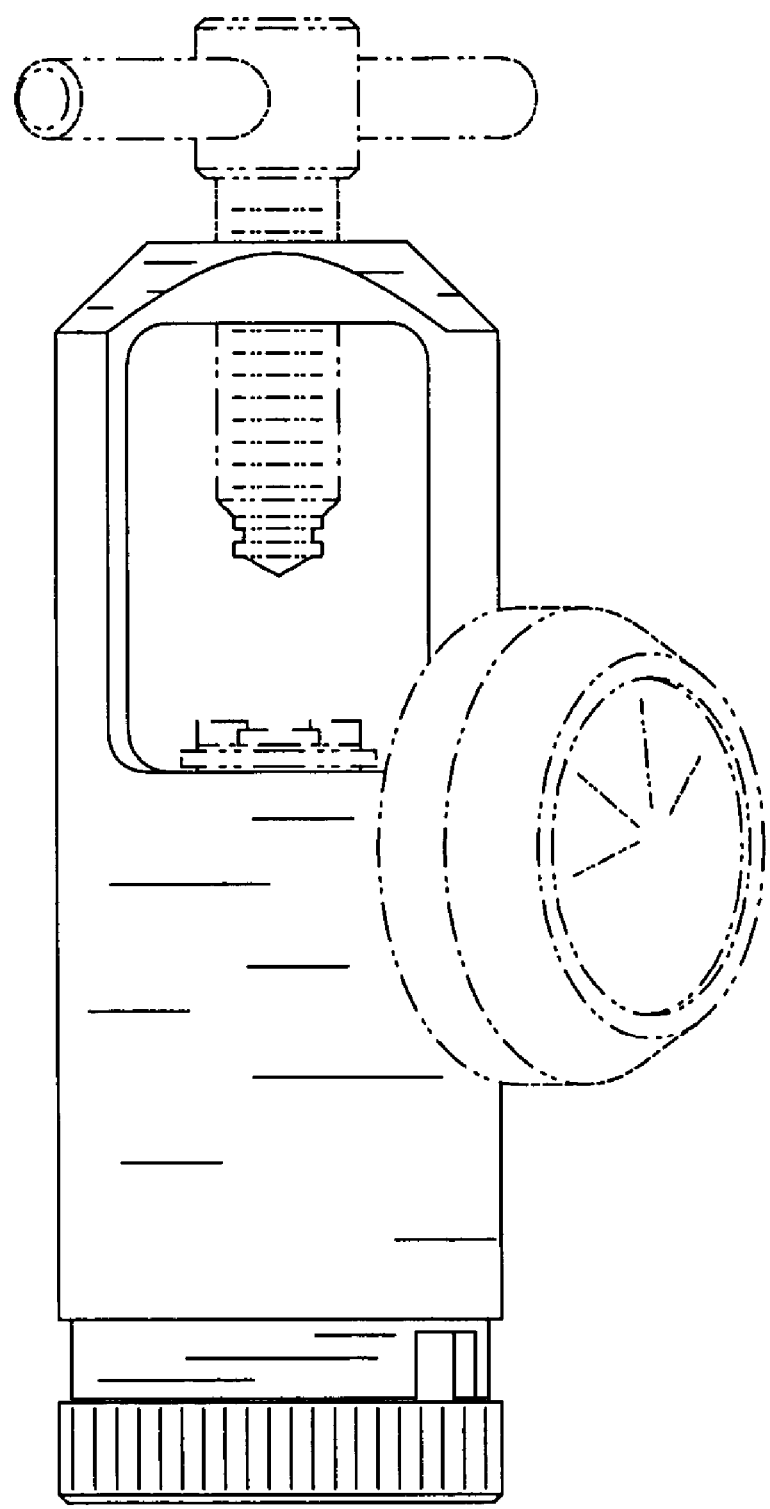
FIG. 23 is a front view of the flow regulator of FIG. 20.
Figure 24:
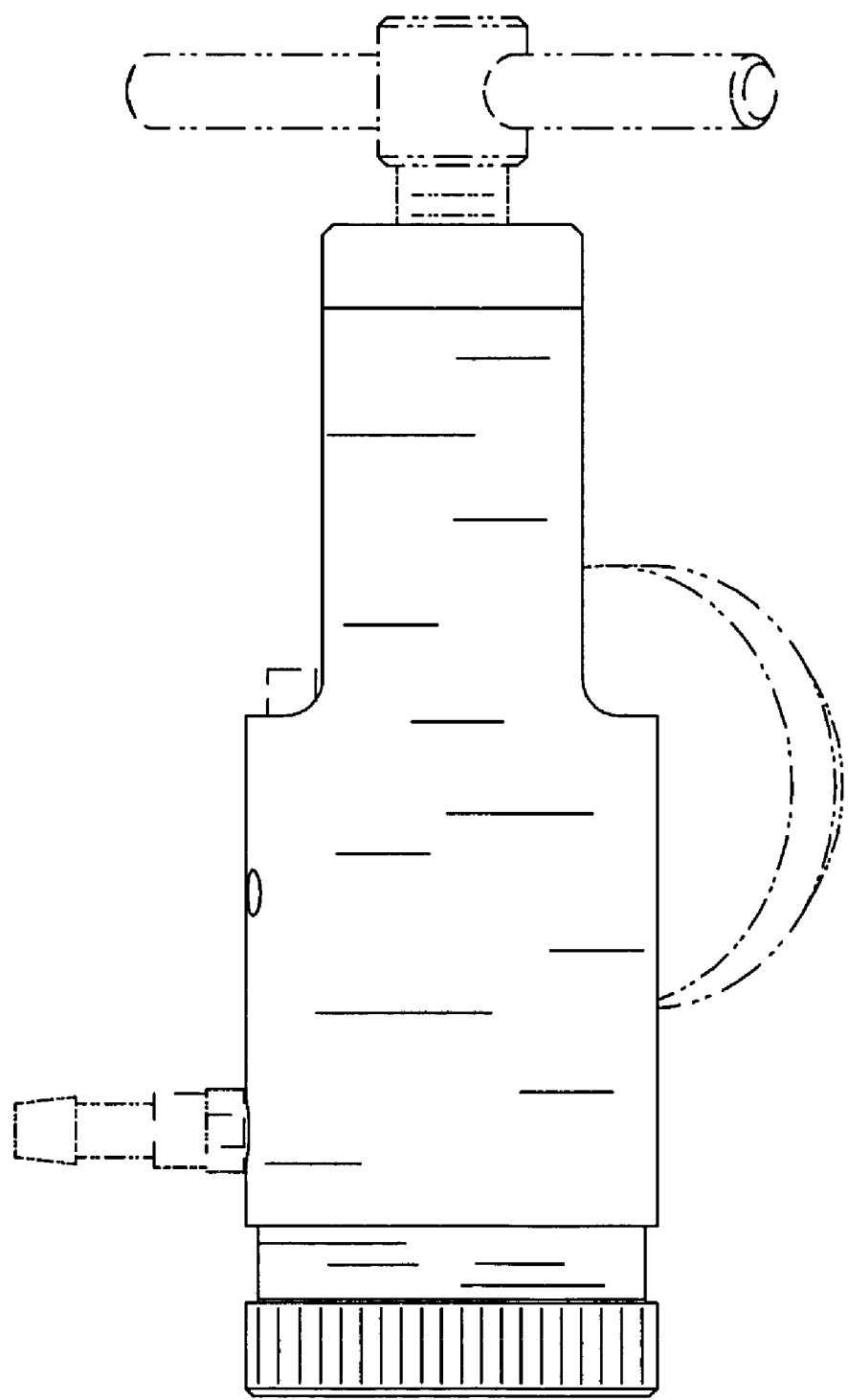
FIG. 24 is a first side view of the flow regulator of FIG. 20.
Figure 25:
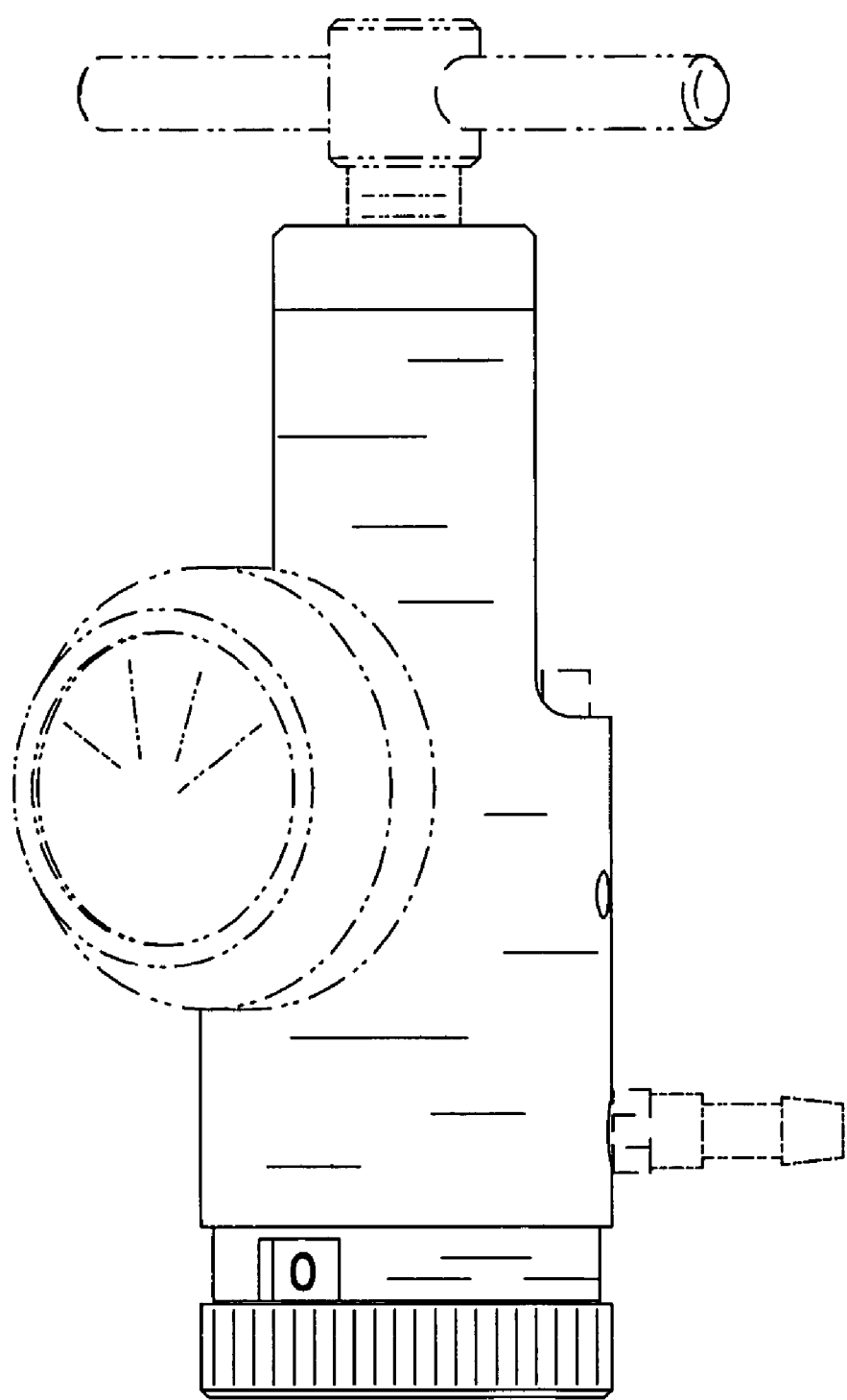
FIG. 25 is a second side view of the flow regulator of FIG. 20.
Figure 26:
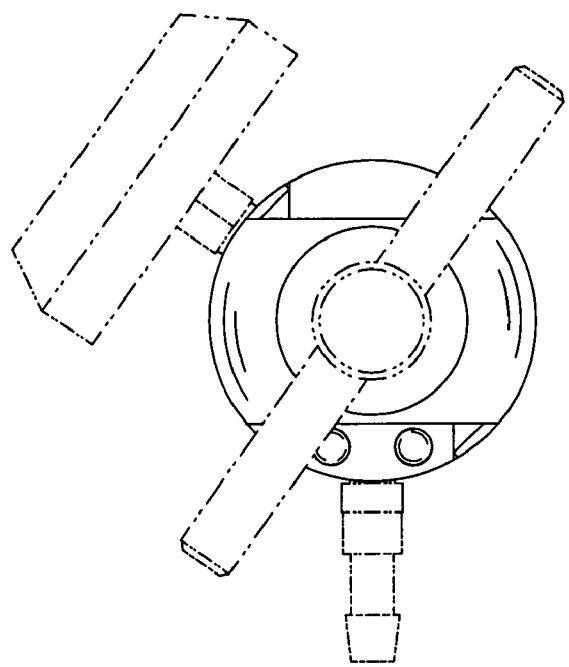
FIG. 26 is a top view of the flow regulator of FIG. 20.
Figure 27:
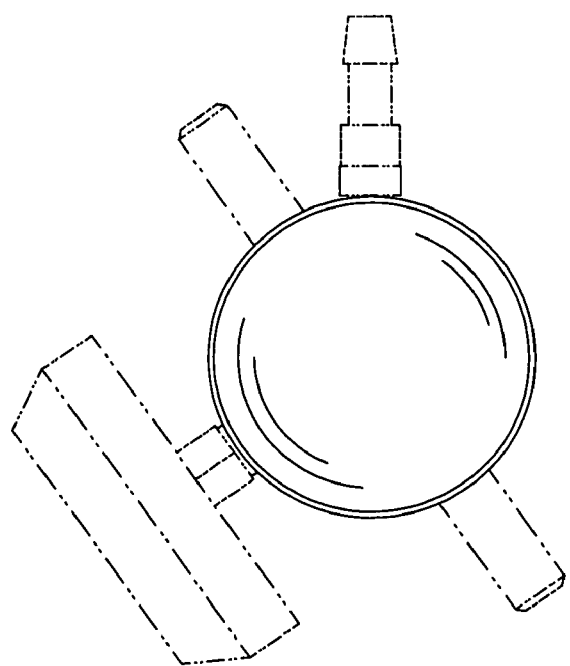
FIG. 27 is a bottom view of the flow regulator of FIG. 20.
Figure 28:
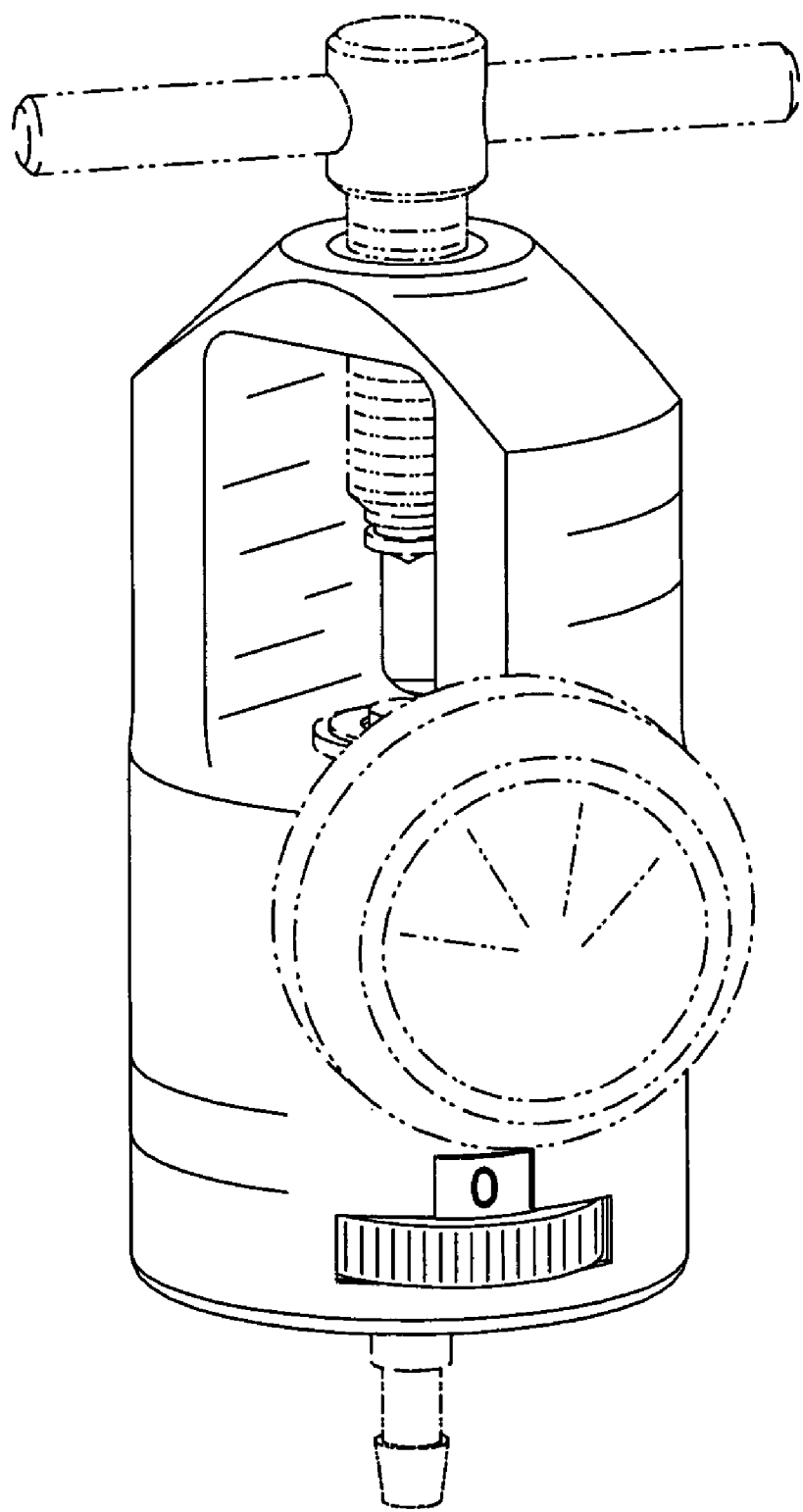
FIG. 28 is a first perspective view of a flow regulator shown at a scale of 1.25 having a housing, a flow selector partially contained within the housing and actuatable from the side of the housing, and a fluid outlet extending from the bottom of the flow regulator.
Figure 29:
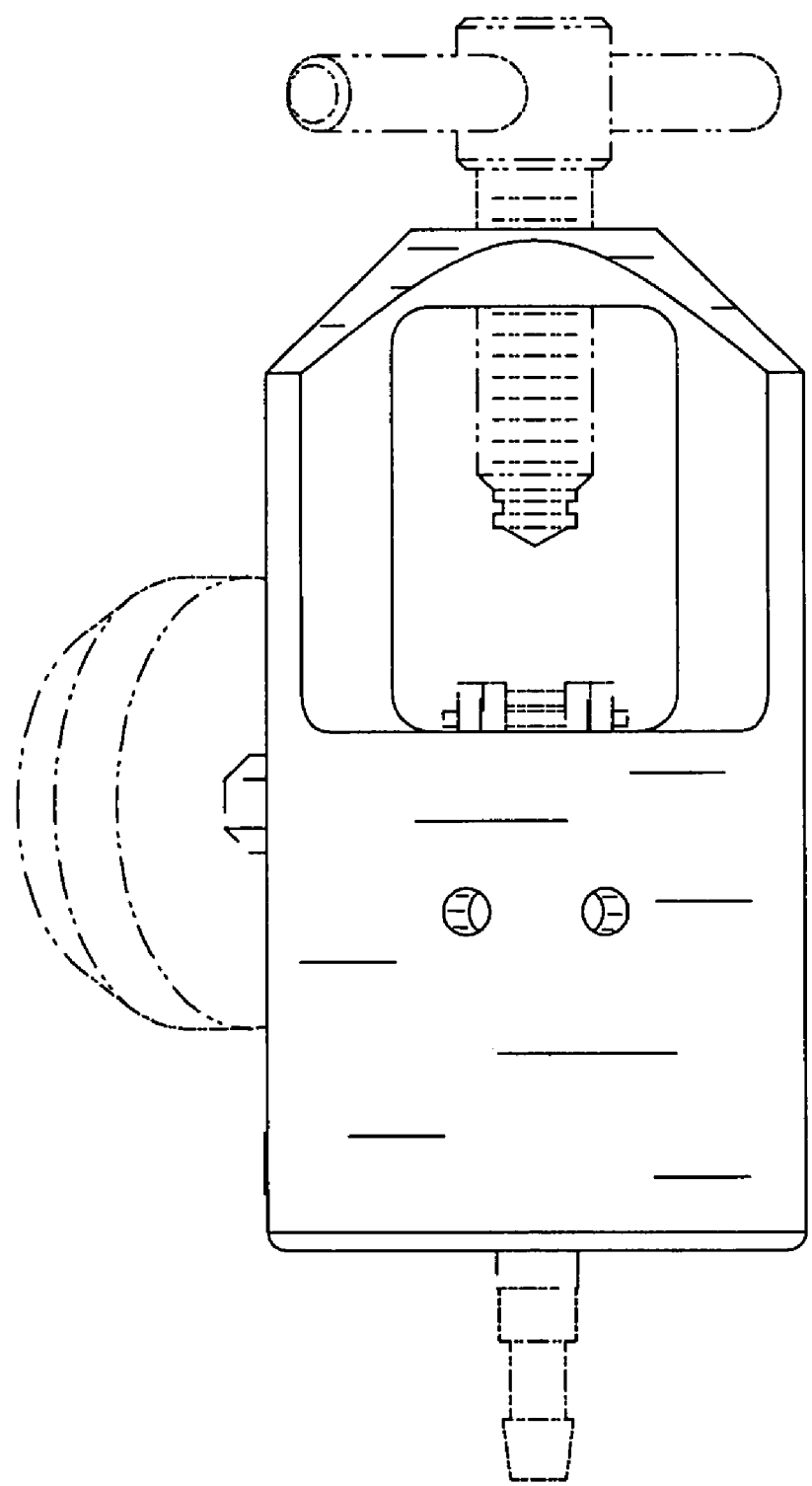
FIG. 29 is back view of the flow regulator of FIG. 28.
Figure 30:
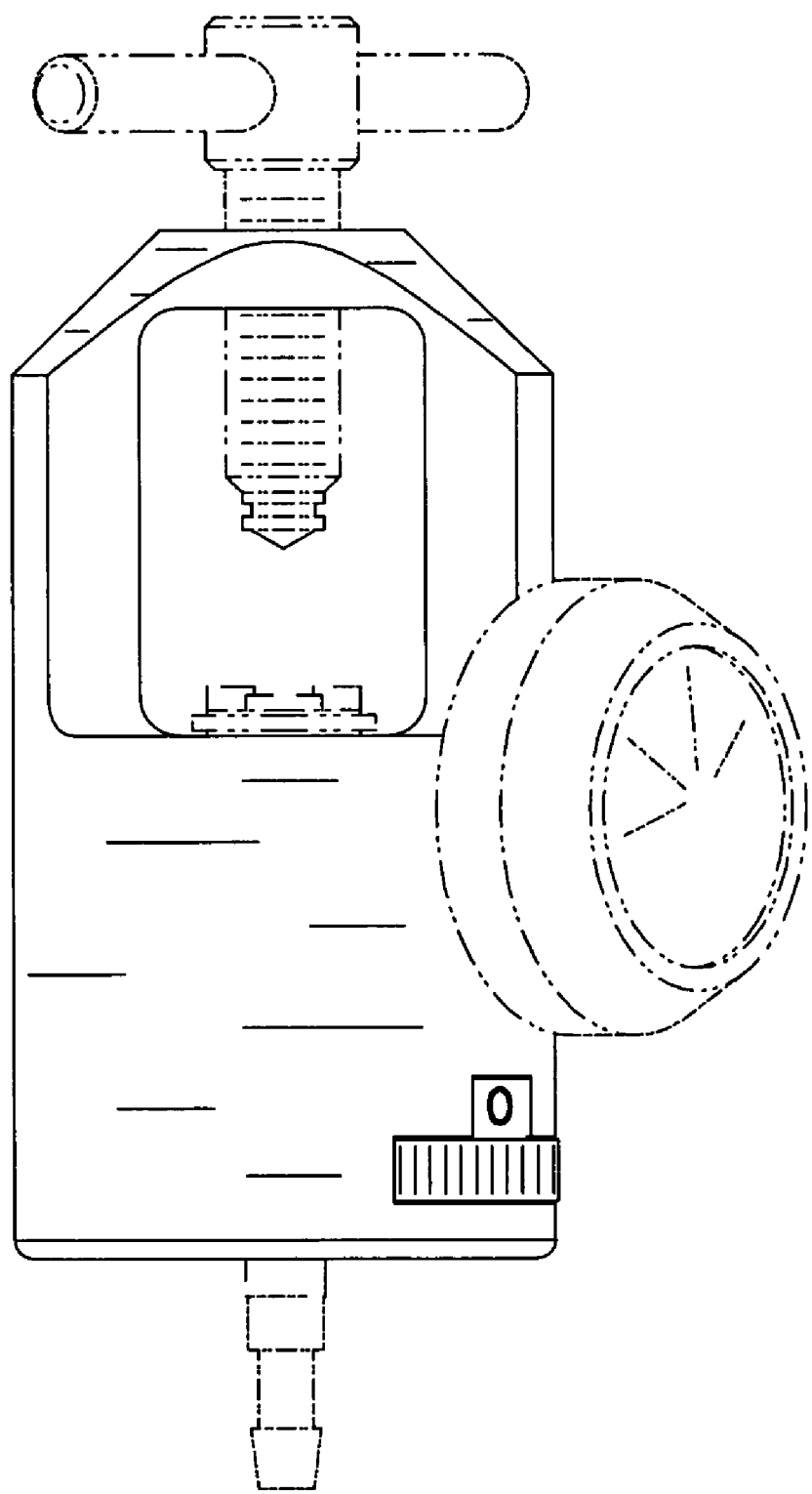
FIG. 30 is a front view of the flow regulator of FIG. 28.
Figure 31:
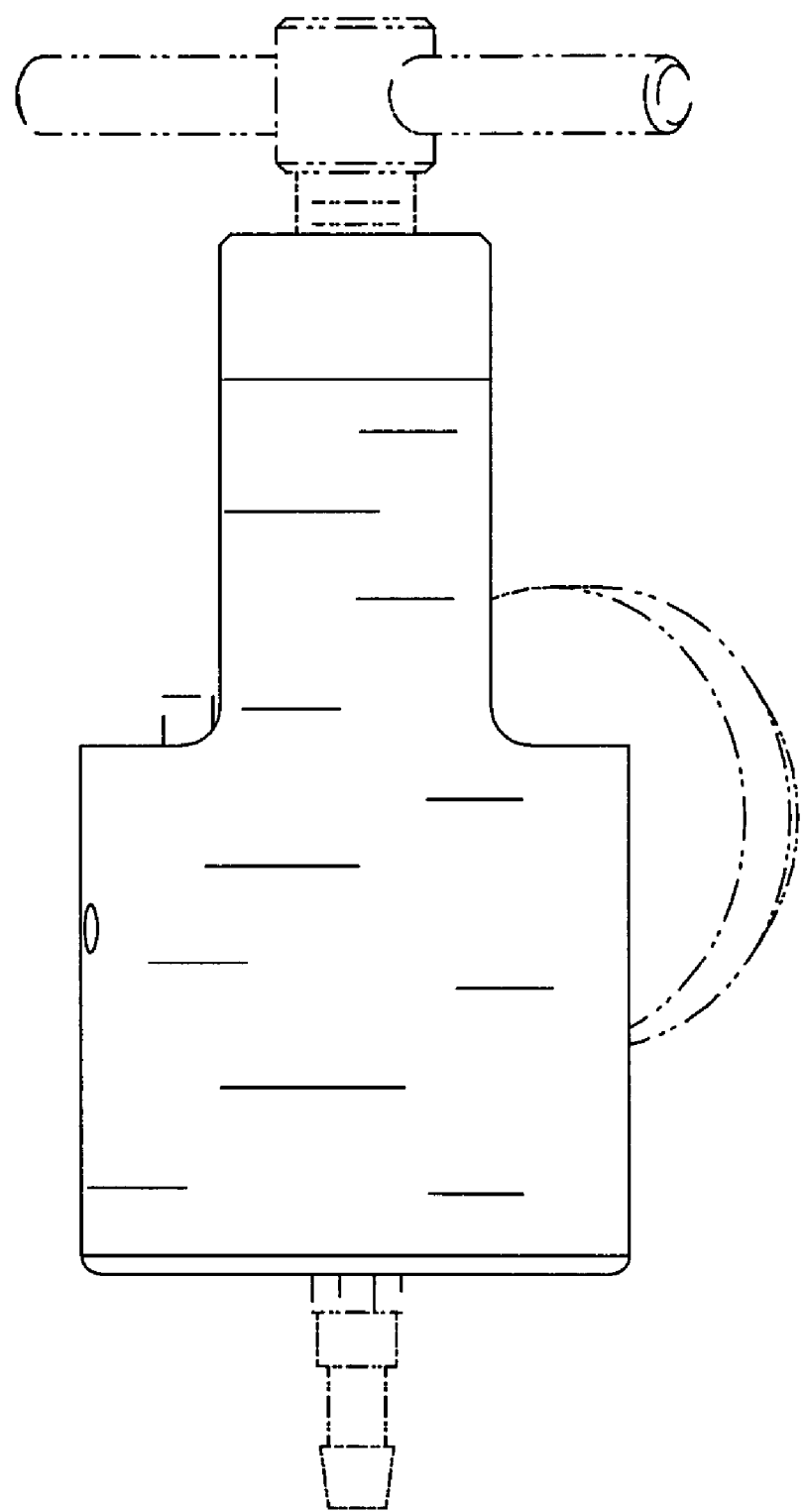
FIG. 31 is a first side view of the flow regulator of FIG. 28.
Figure 32:
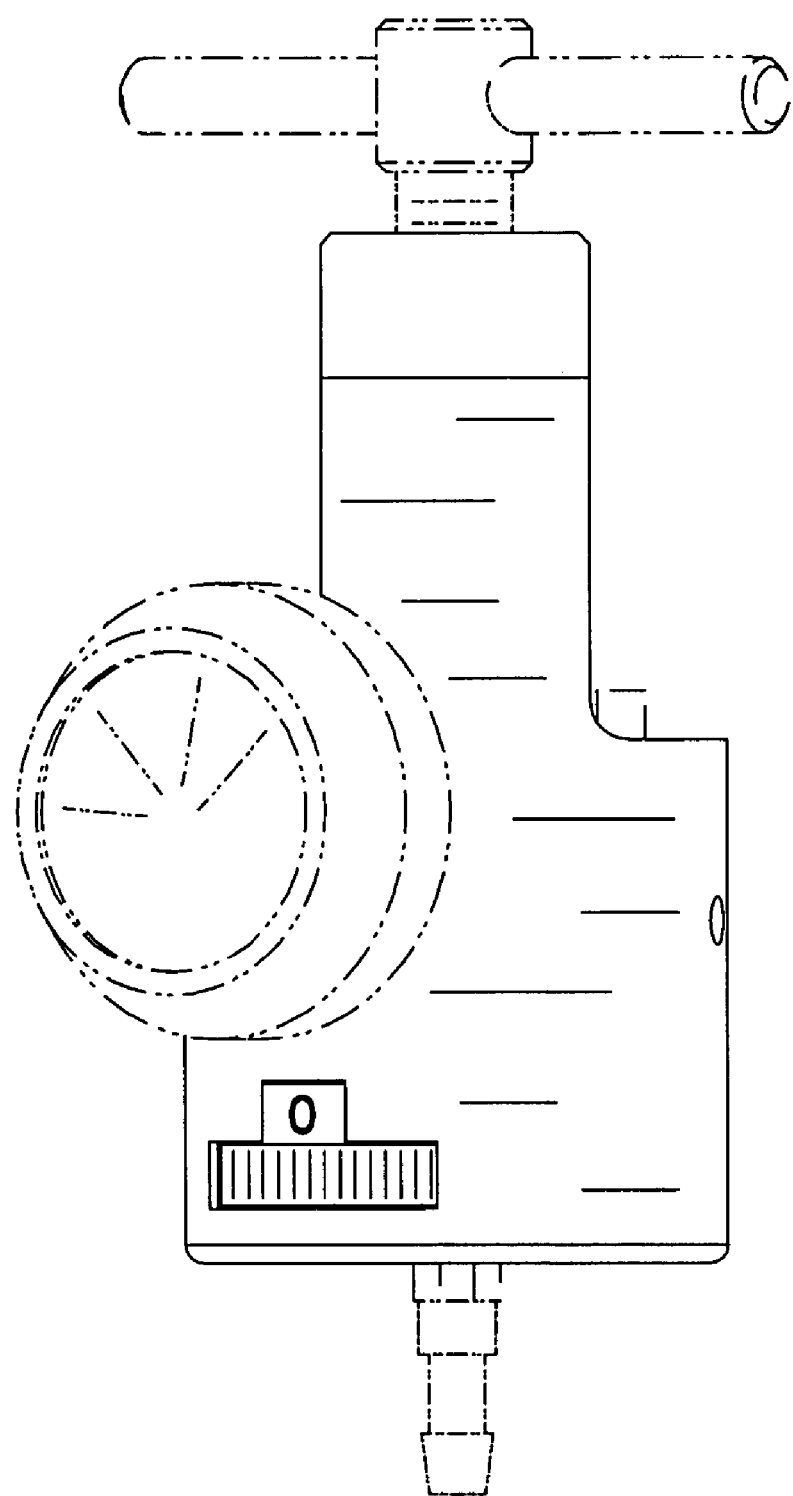
FIG. 32 is a second side view of the flow regulator of FIG. 28.
Figure 33:
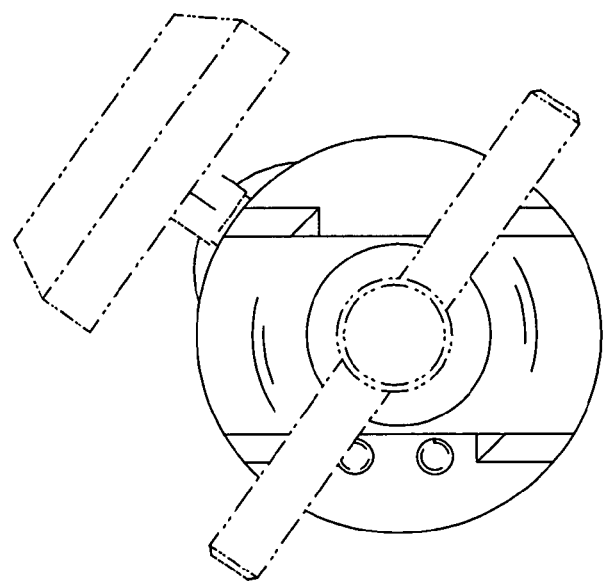
FIG. 33 is a top view of the flow regulator of FIG. 28.
Figure 34:
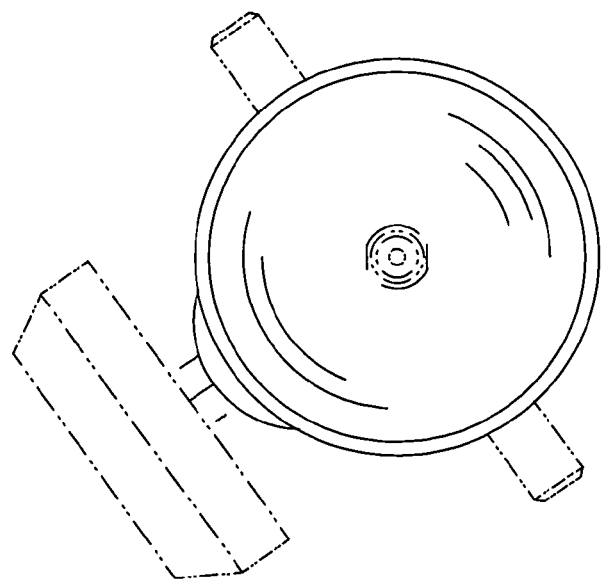
FIG. 34 is a bottom view of the flow regulator of FIG. 28.
Figure 35:
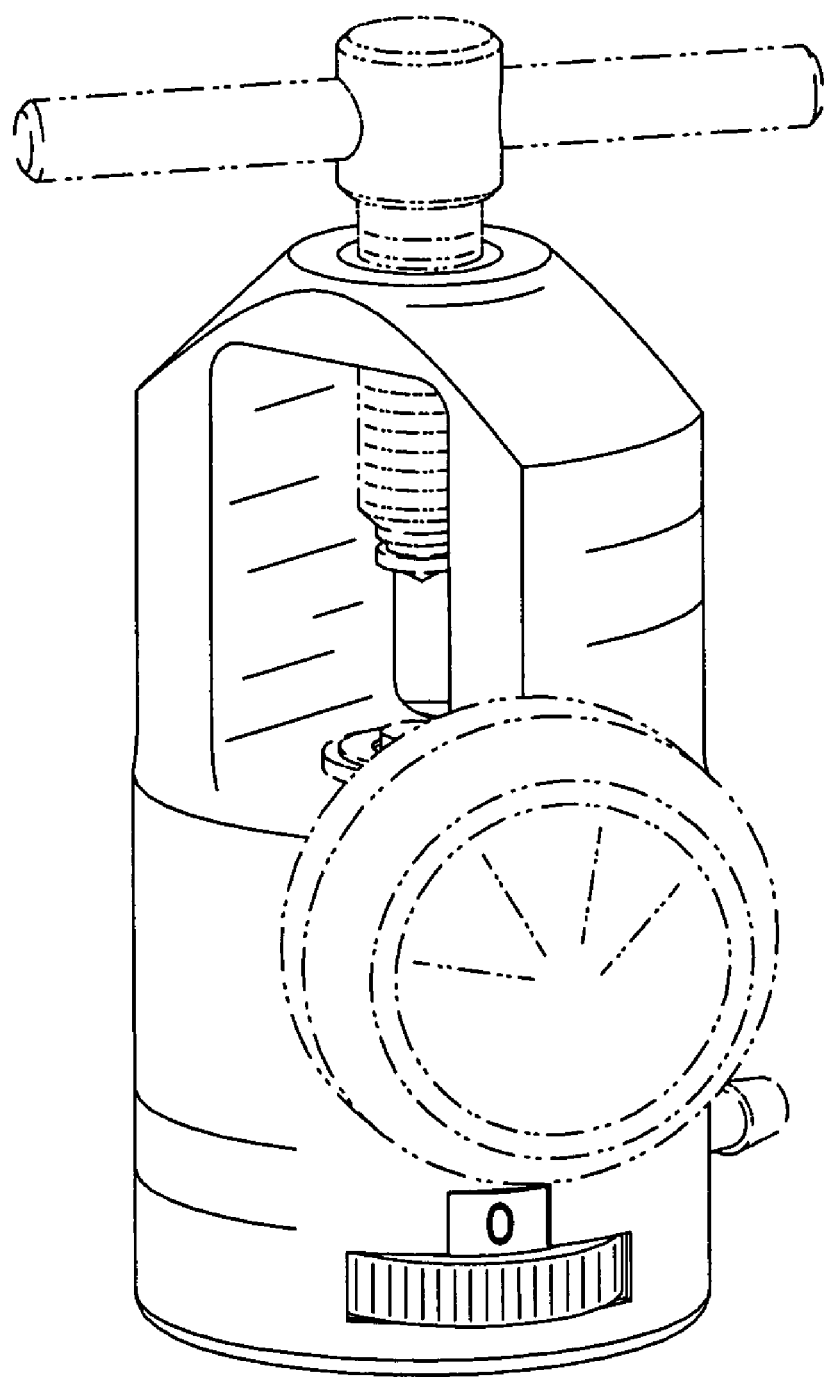
FIG. 35 is a first perspective view of a flow regulator shown at a scale of 1.25 having a housing, a flow selector partially contained within the housing and actuatable from the side of the housing, and a fluid outlet extending from a radial surface of the flow regulator.
Figure 36:
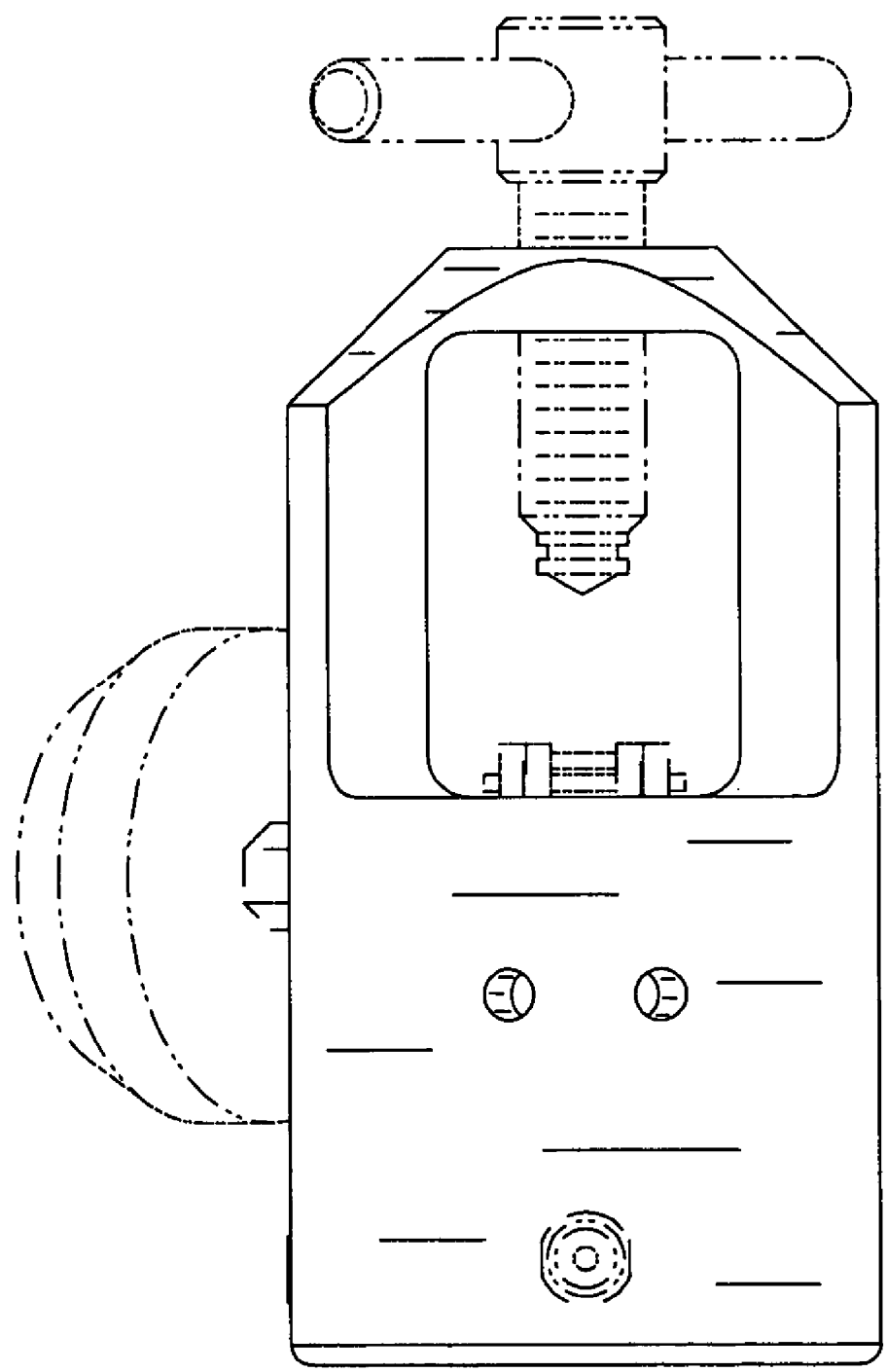
FIG. 36 is back view of the flow regulator of FIG. 35.
Figure 37:
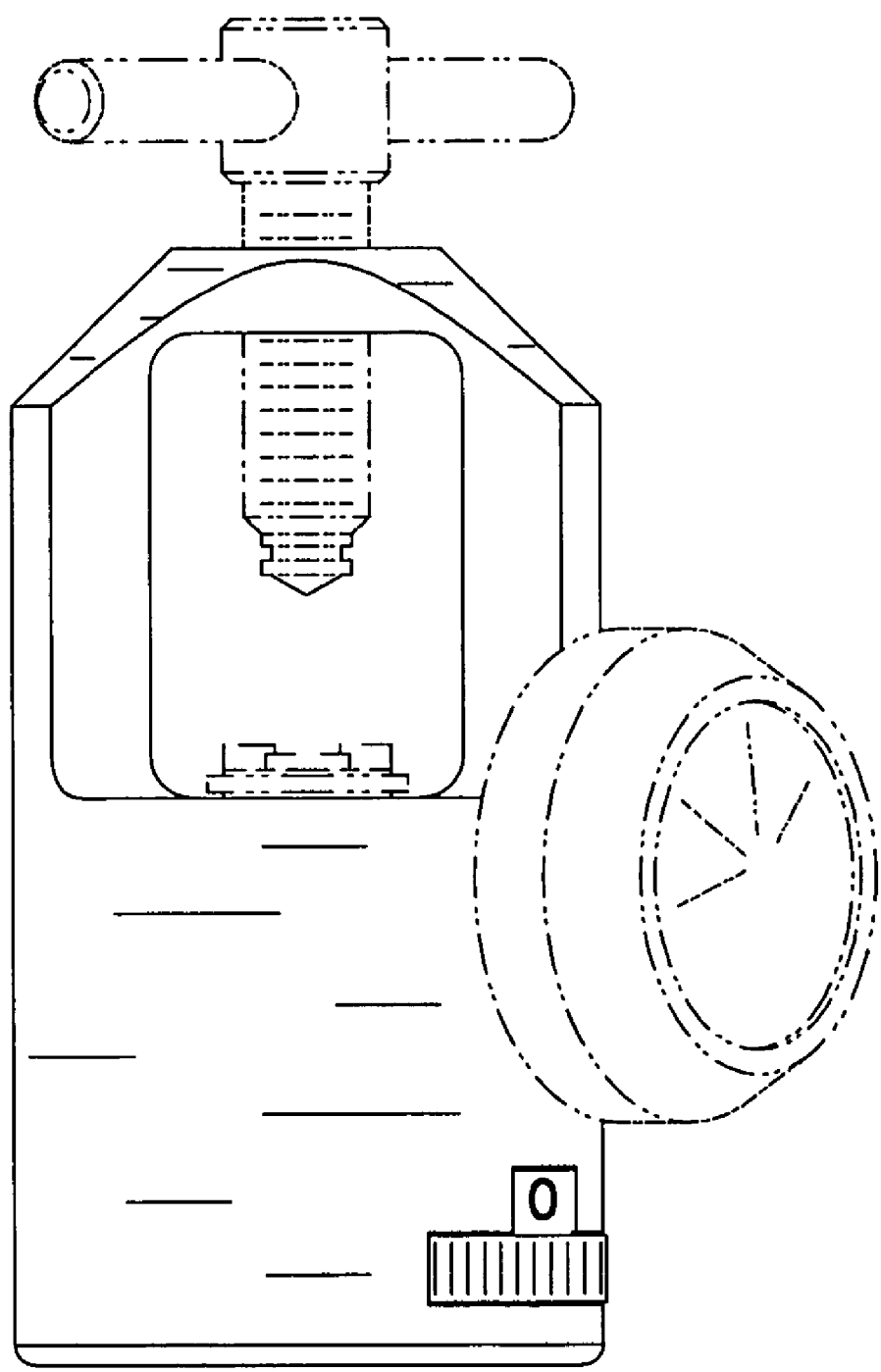
FIG. 37 is a front view of the flow regulator of FIG. 35.
Figure 38:
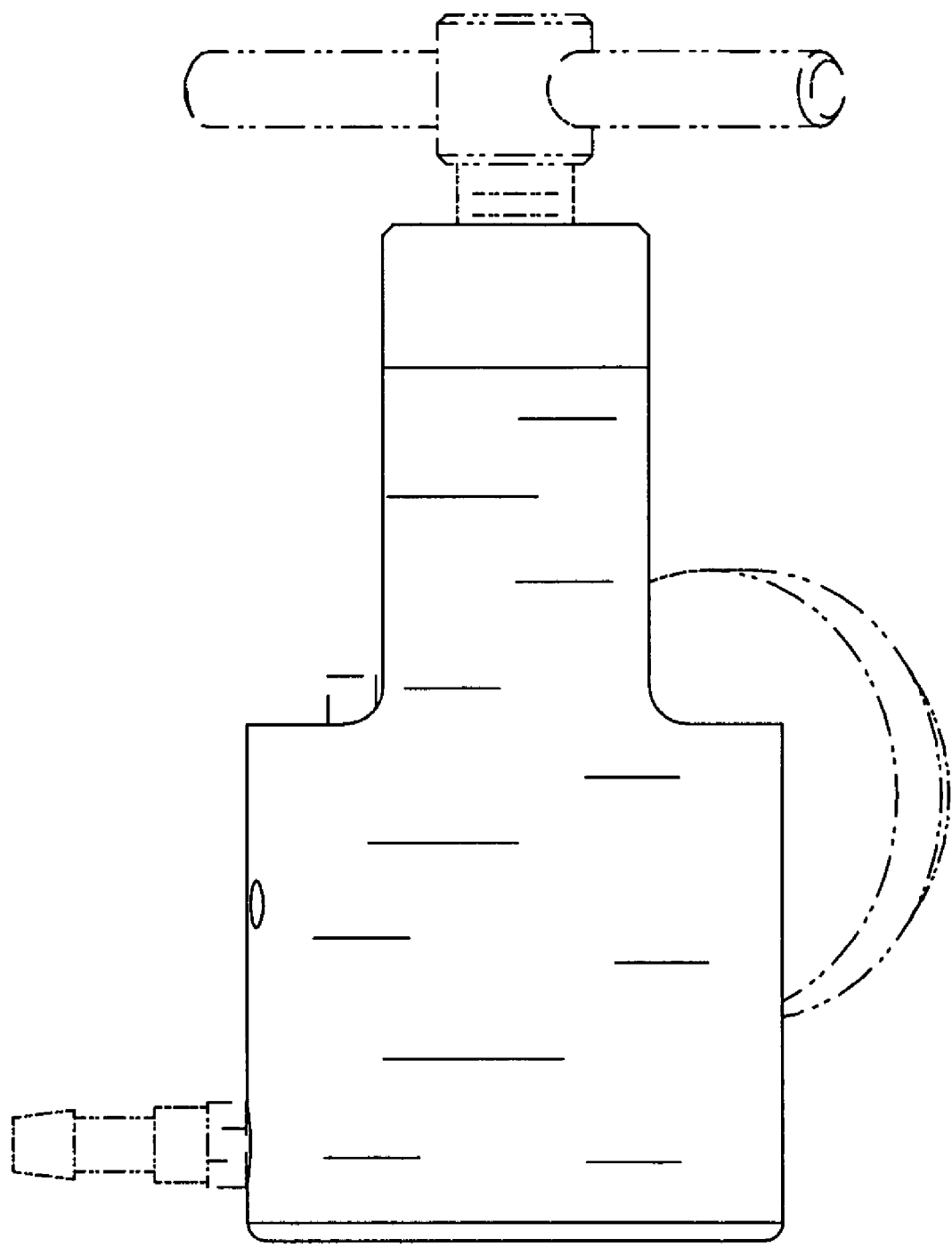
FIG. 38 is a first side view of the flow regulator of FIG. 35.
Figure 39:
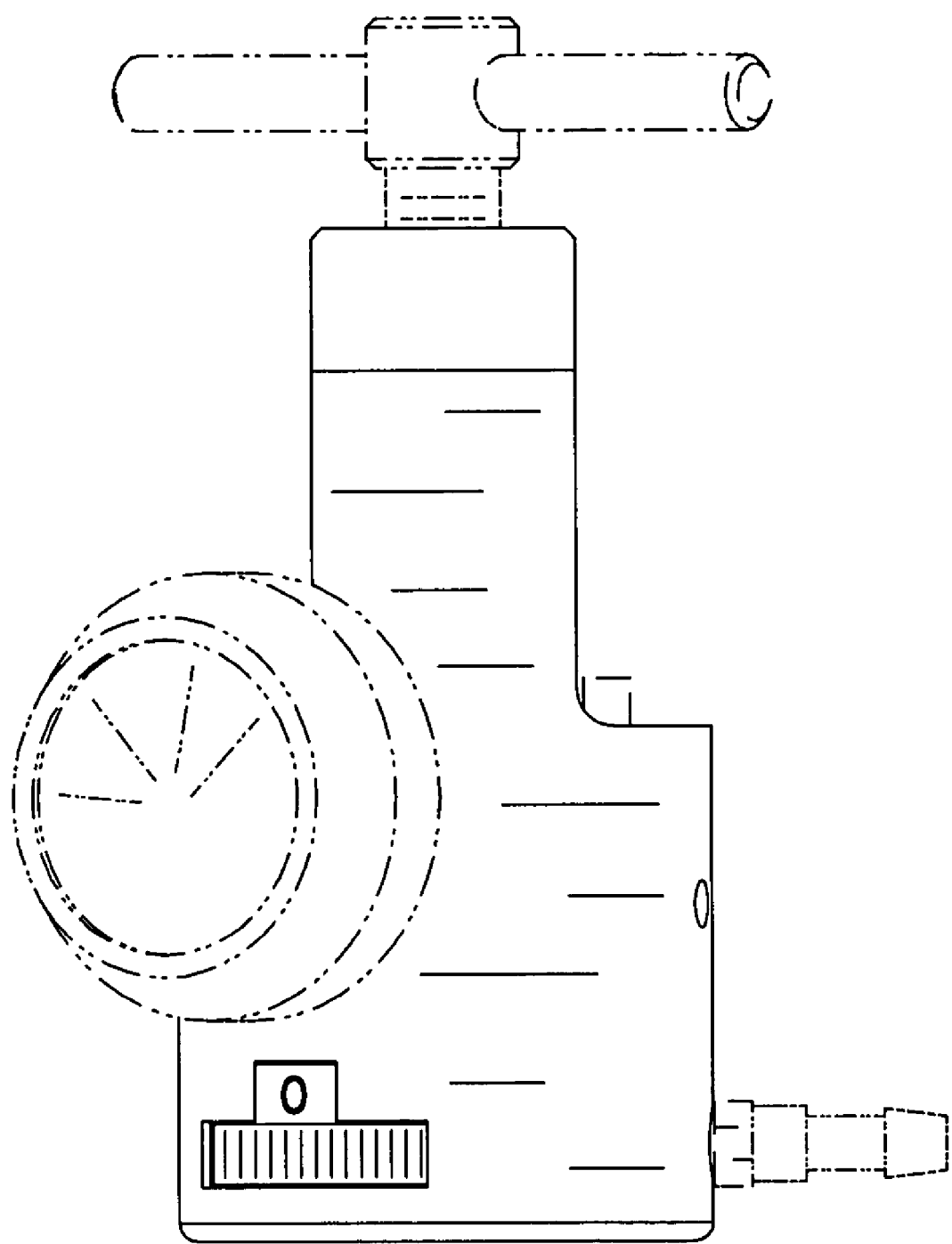
FIG. 39 is a second side view of the flow regulator of FIG. 35.
Figure 40:
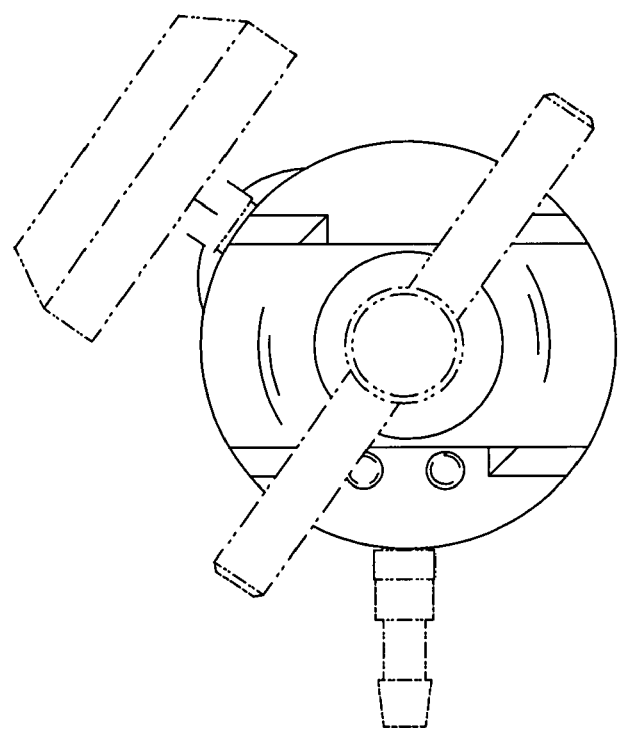
FIG. 40 is a top view of the flow regulator of FIG. 35.
Figure 41:
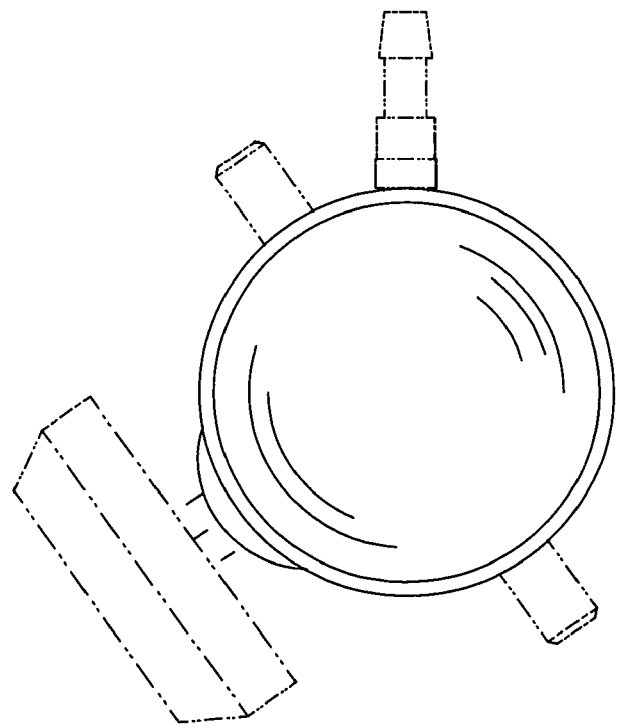
FIG. 41 is a bottom view of the flow regulator of FIG. 35.
Figure 42:
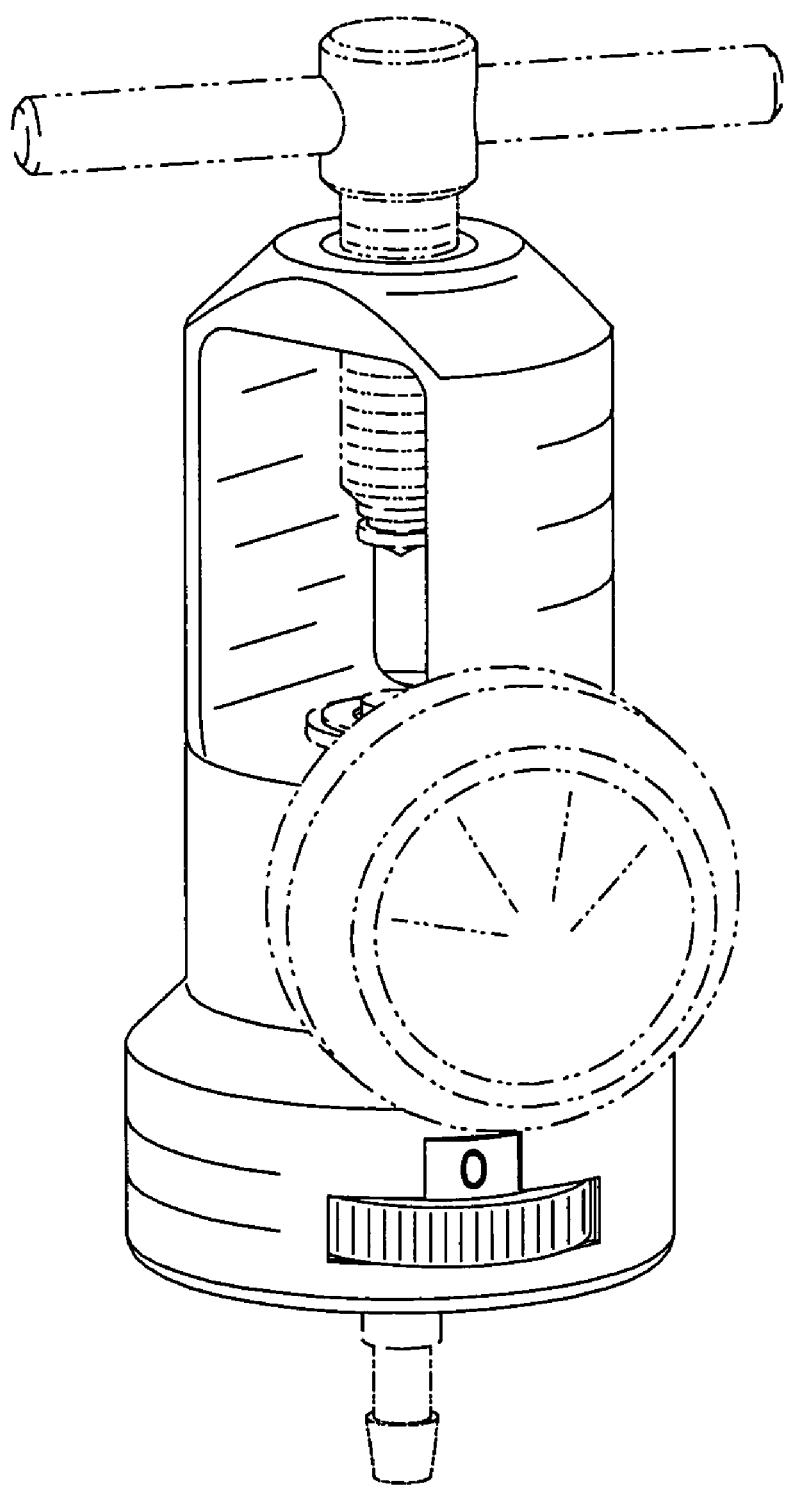
FIG. 42 is a perspective view of a flow regulator shown at a scale of 1.25 having a housing, a flow selector partially contained within the housing and actuatable from the side of the housing, and a fluid outlet extending from the bottom of the flow regulator, the housing being a first diameter proximate to a yoke of the housing and a second diameter proximate to the flow selector.
Figure 43:
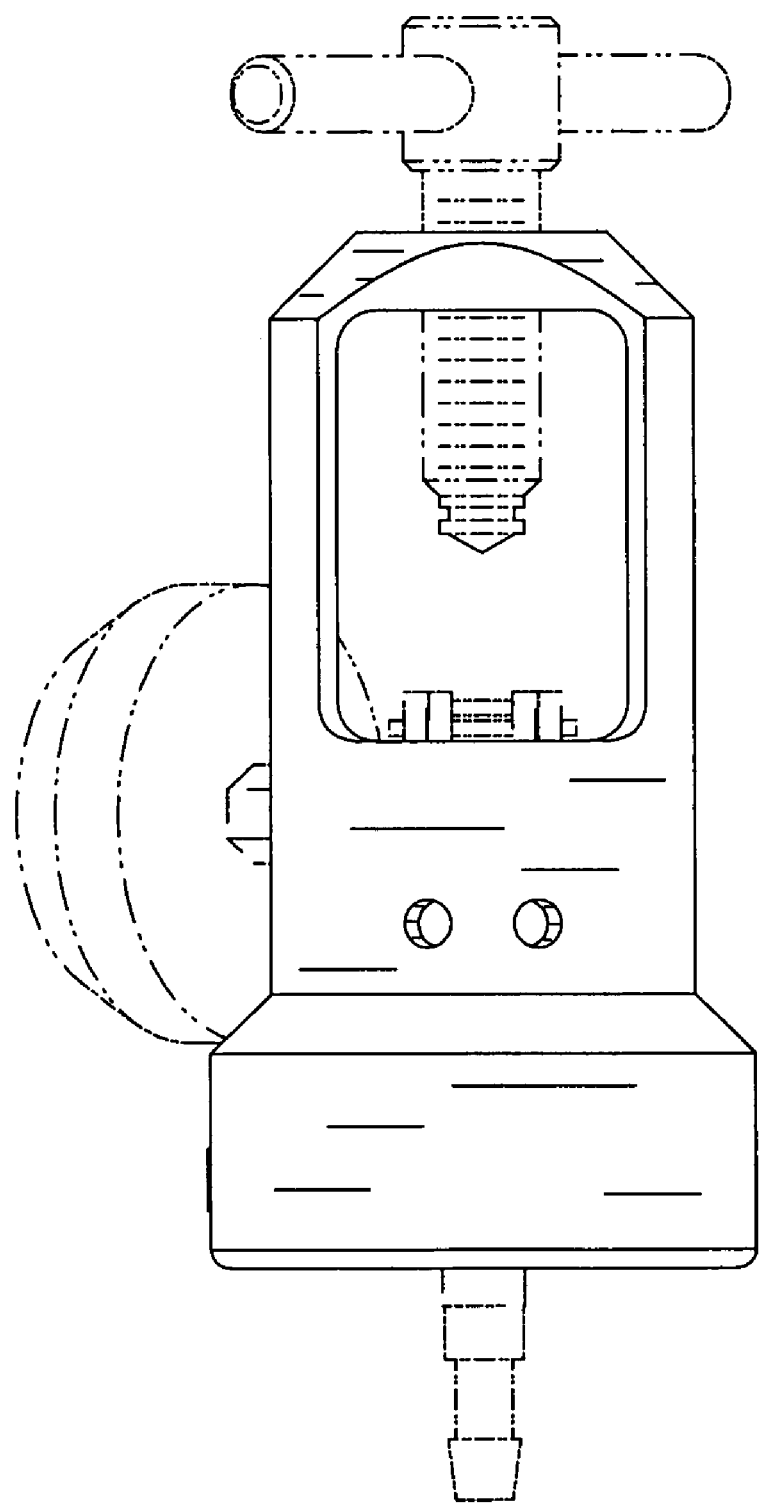
FIG. 43 is back view of the flow regulator of FIG. 42.
Figure 44:
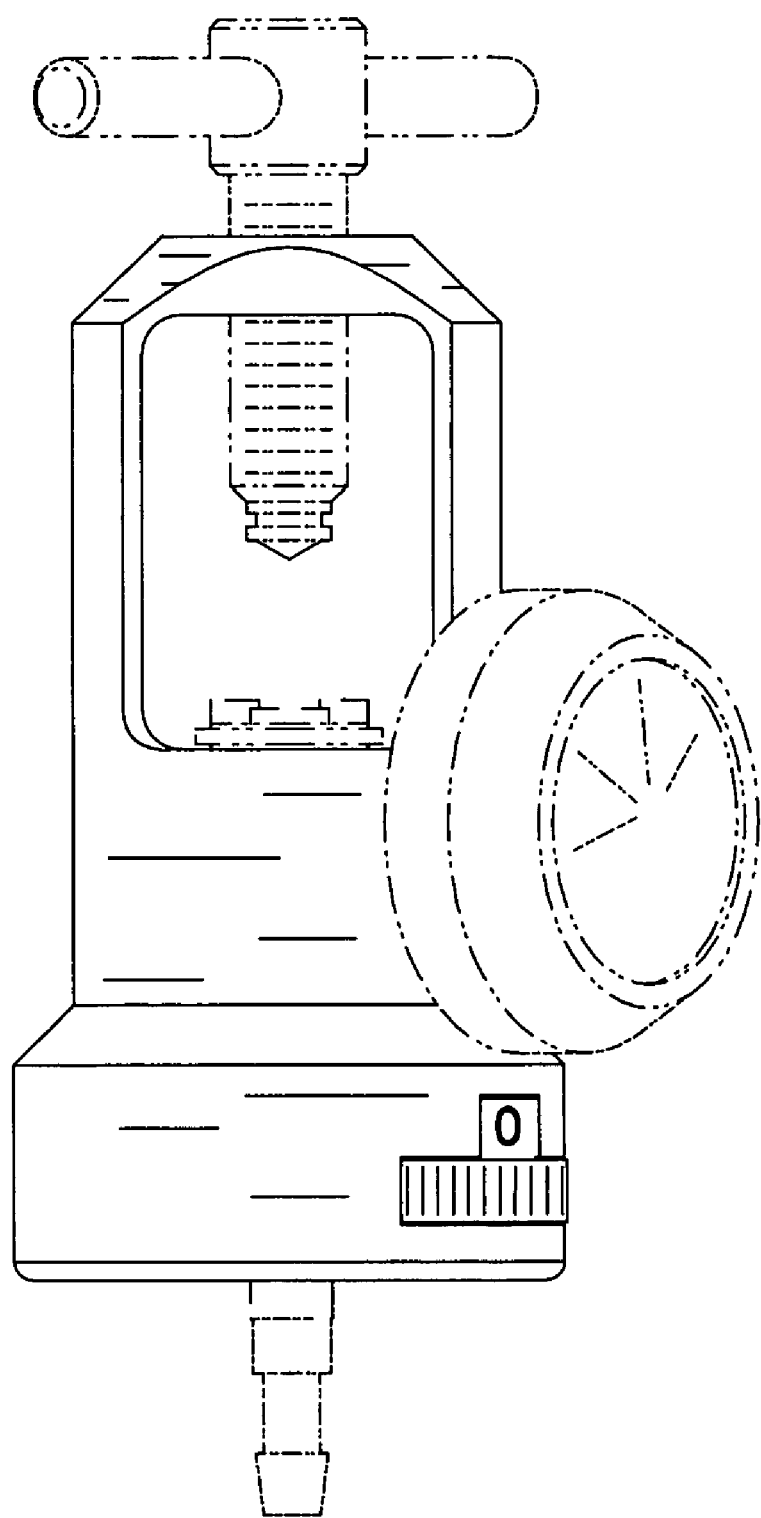
FIG. 44 is a front view of the flow regulator of FIG. 42.
Figure 45:
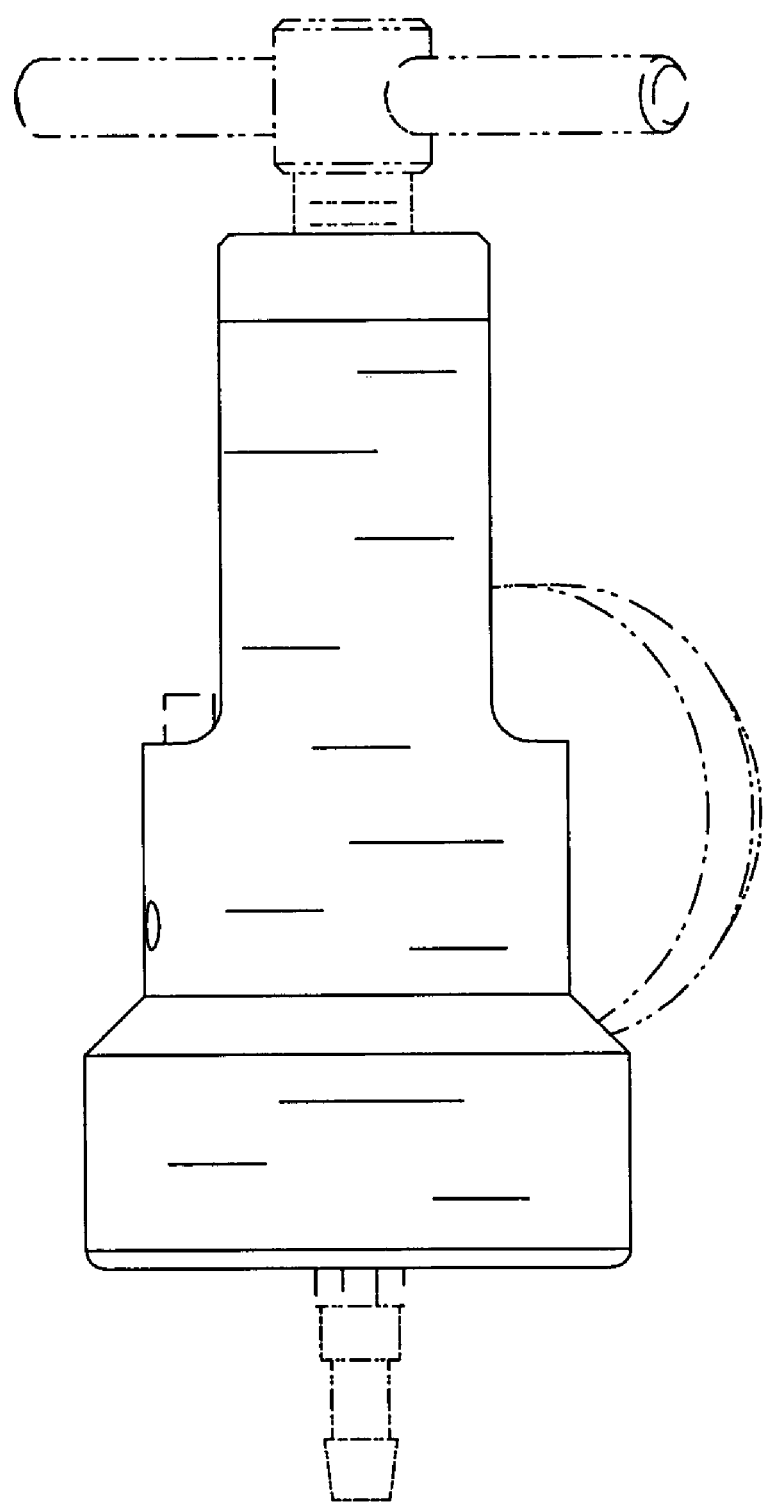
FIG. 45 is a first side view of the flow regulator of FIG. 42.
Figure 46:
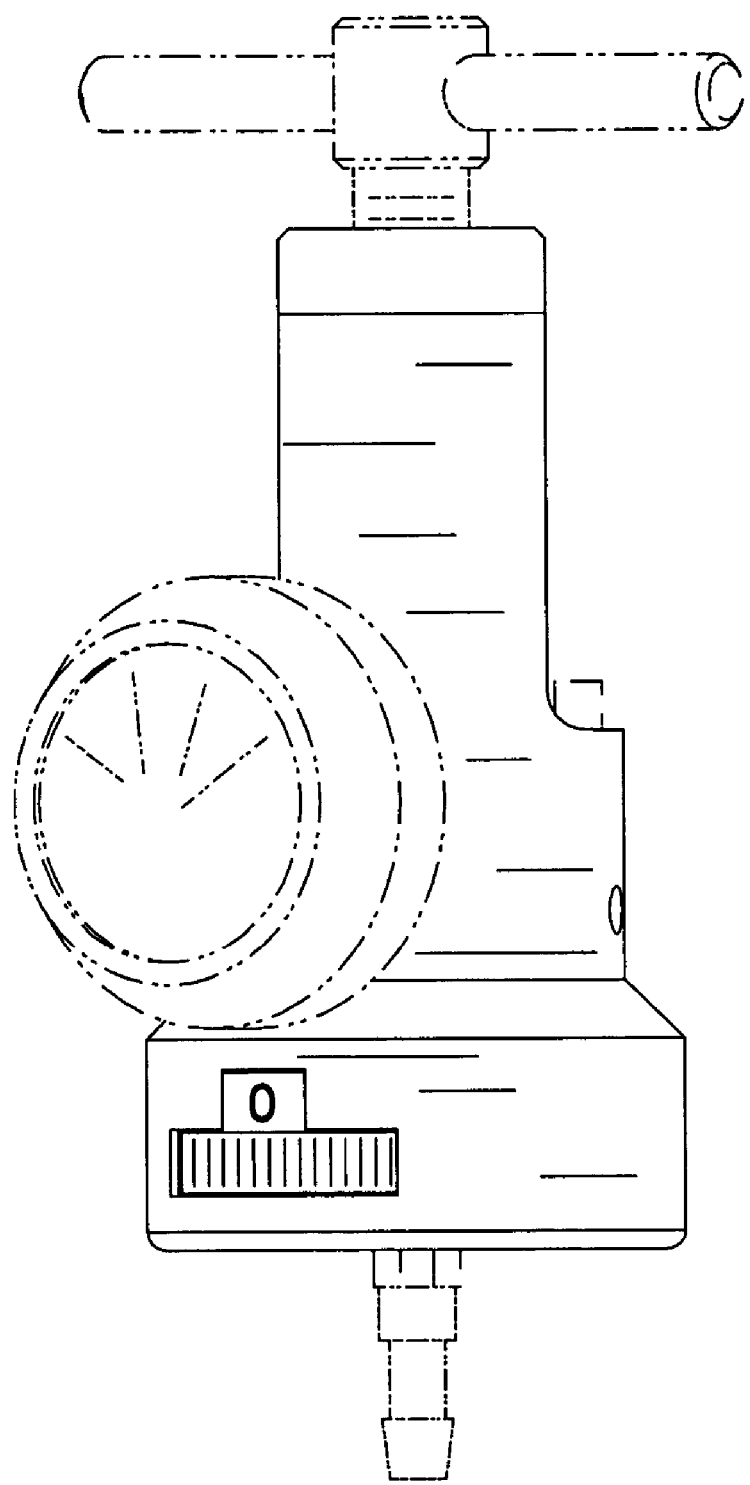
FIG. 46 is a second side view of the flow regulator of FIG. 42.
Figure 47:
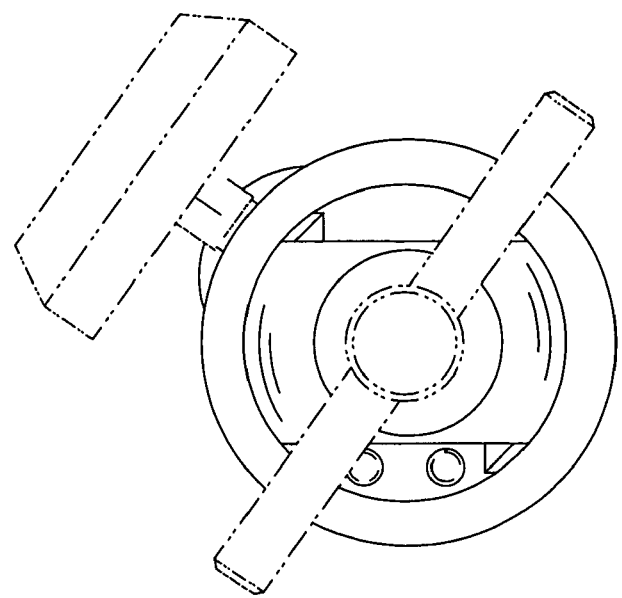
FIG. 47 is a top view of the flow regulator of FIG. 42.
Figure 48:
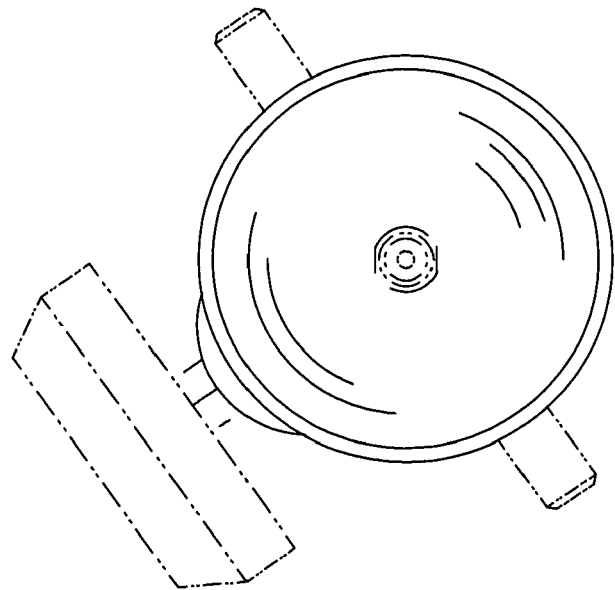
FIG. 48 is a bottom view of the flow regulator of FIG. 42.
Figure 49:
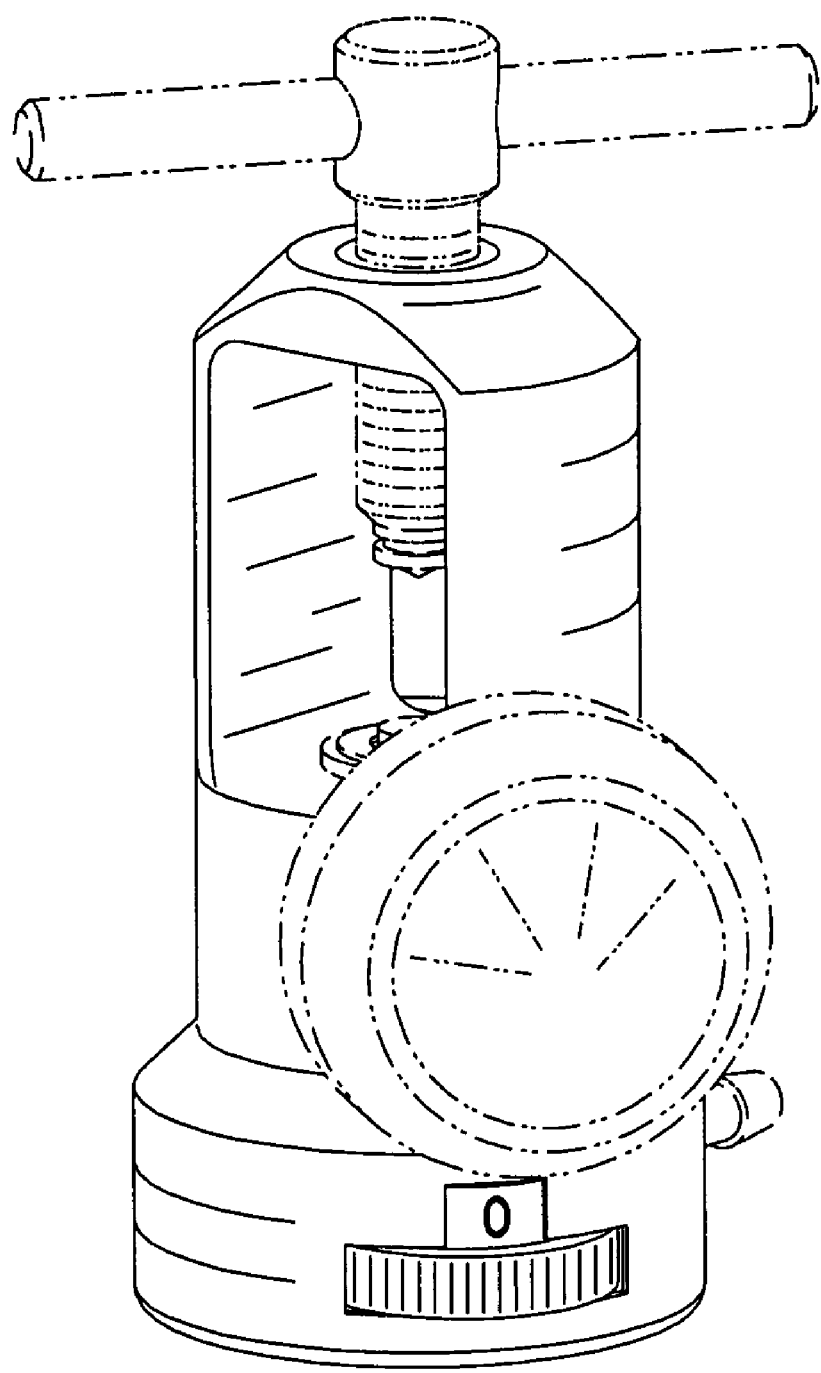
FIG. 49 is a first perspective view of a flow regulator shown at a scale of 1.25 having a housing, a flow selector partially contained within the housing and actuatable from the side of the housing, and a fluid outlet extending from a radial surface of the flow regulator, the housing being a first diameter proximate to a yoke of the housing and a second diameter proximate to the flow selector.
Figure 50:
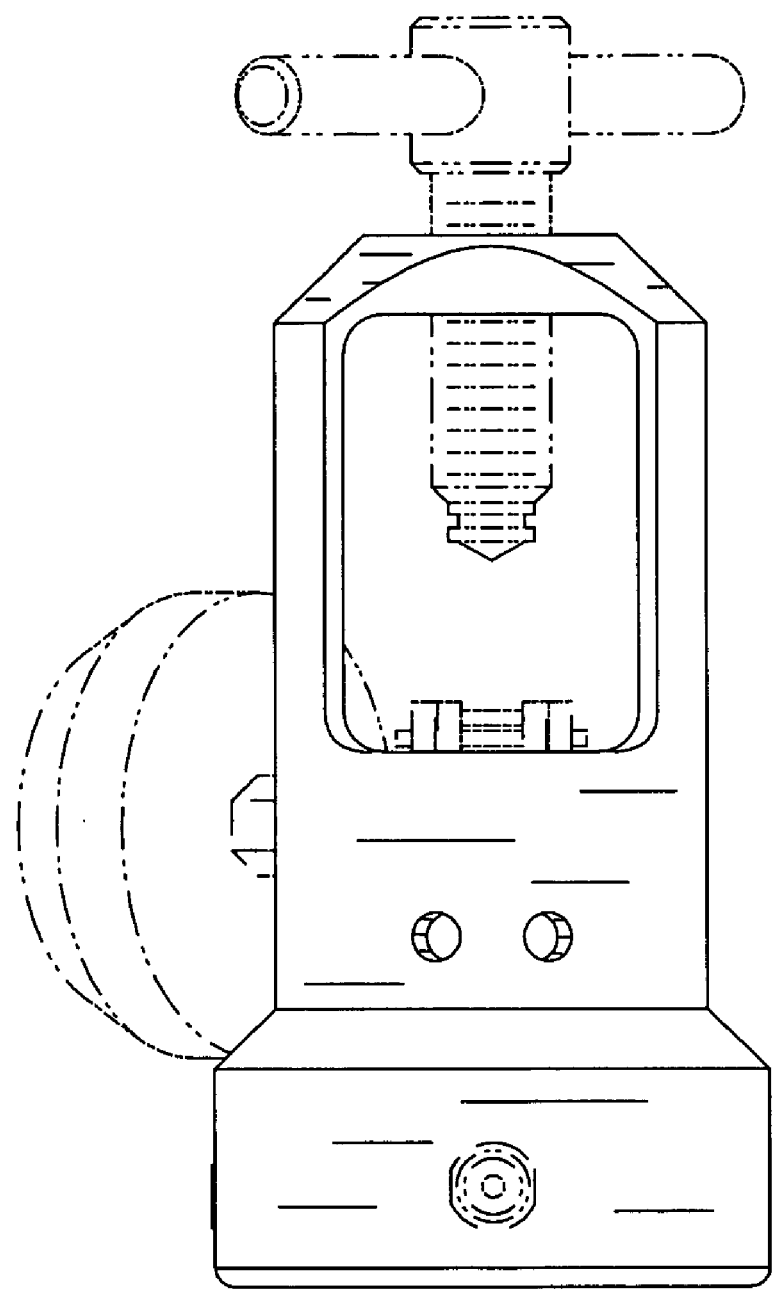
FIG. 50 is back view of the flow regulator of FIG. 49.
Figure 51:
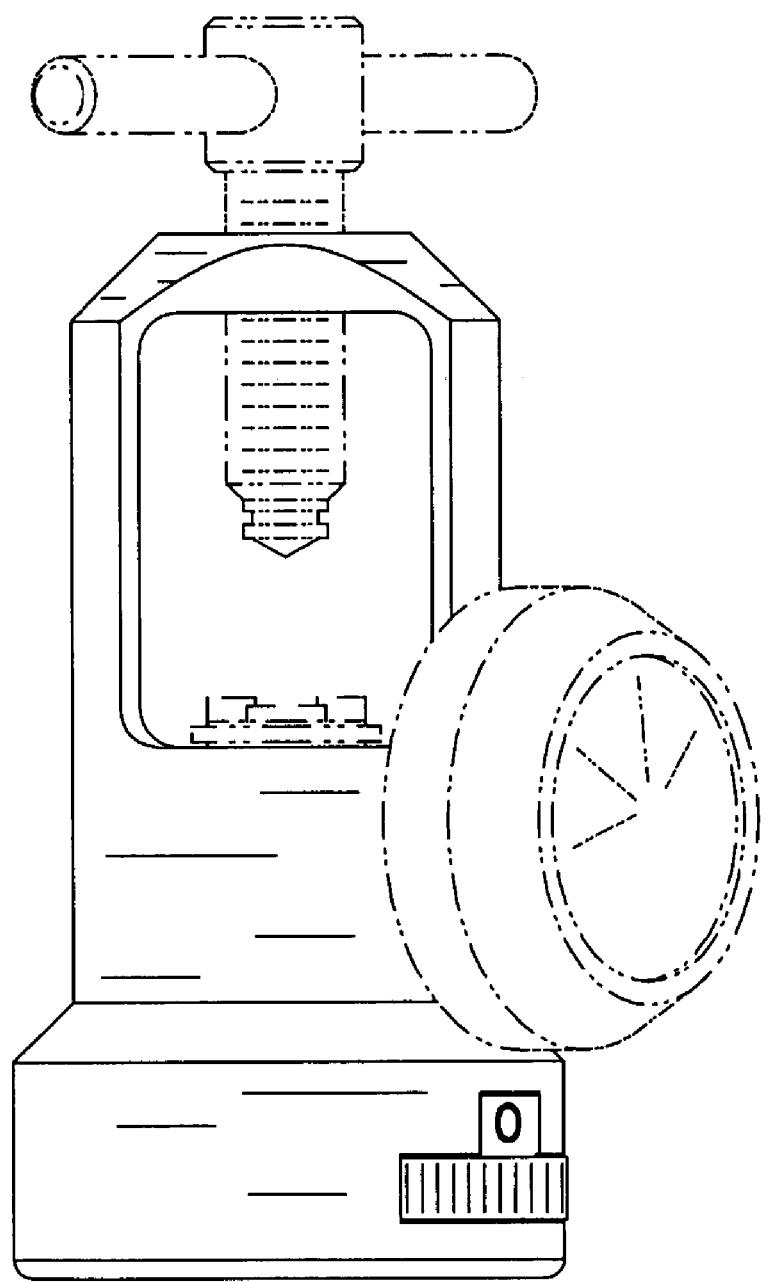
FIG. 51 is a front view of the flow regulator of FIG. 49.
Figure 52:
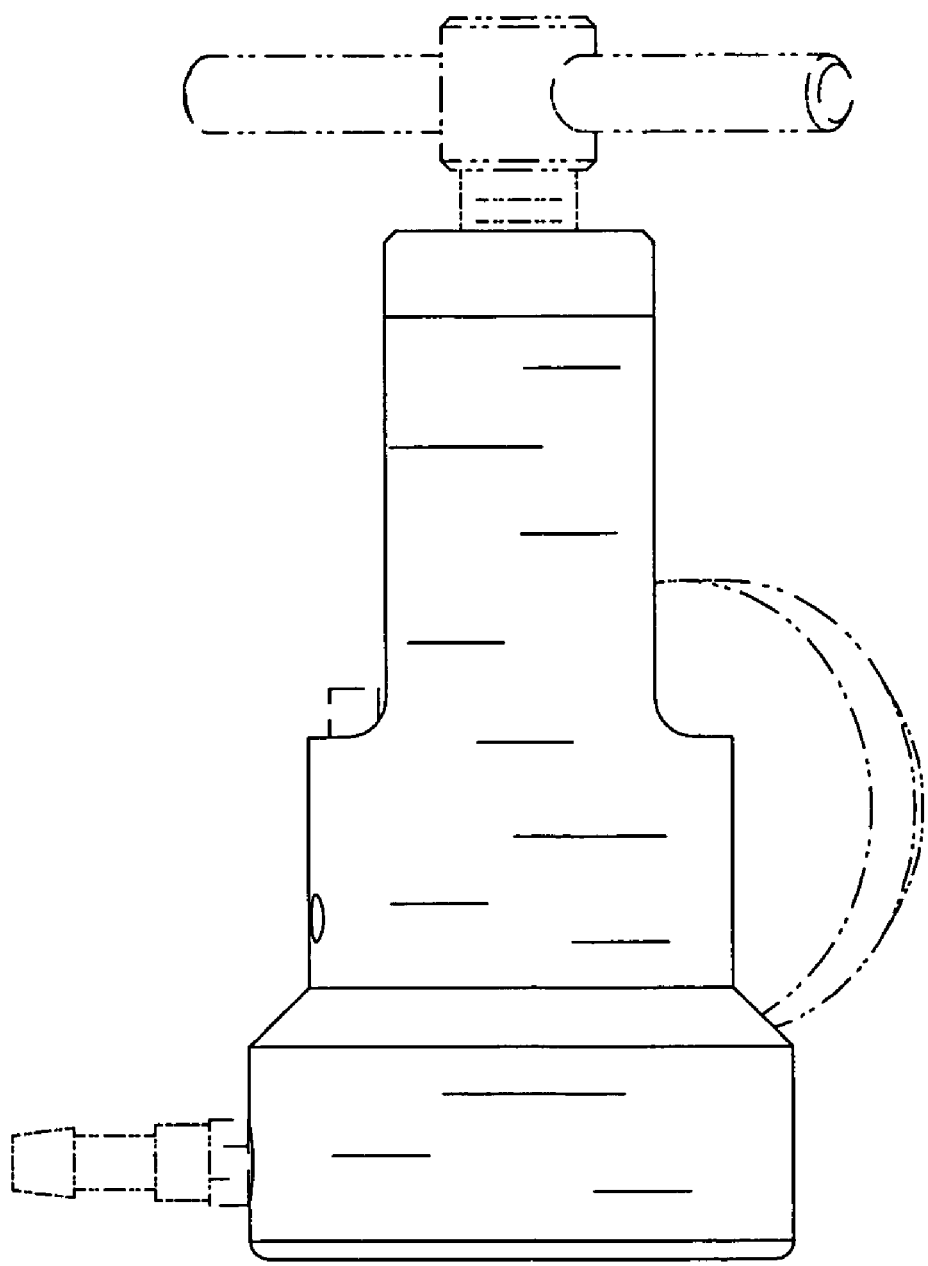
FIG. 52 is a first side view of the flow regulator of FIG. 49.
Figure 53:
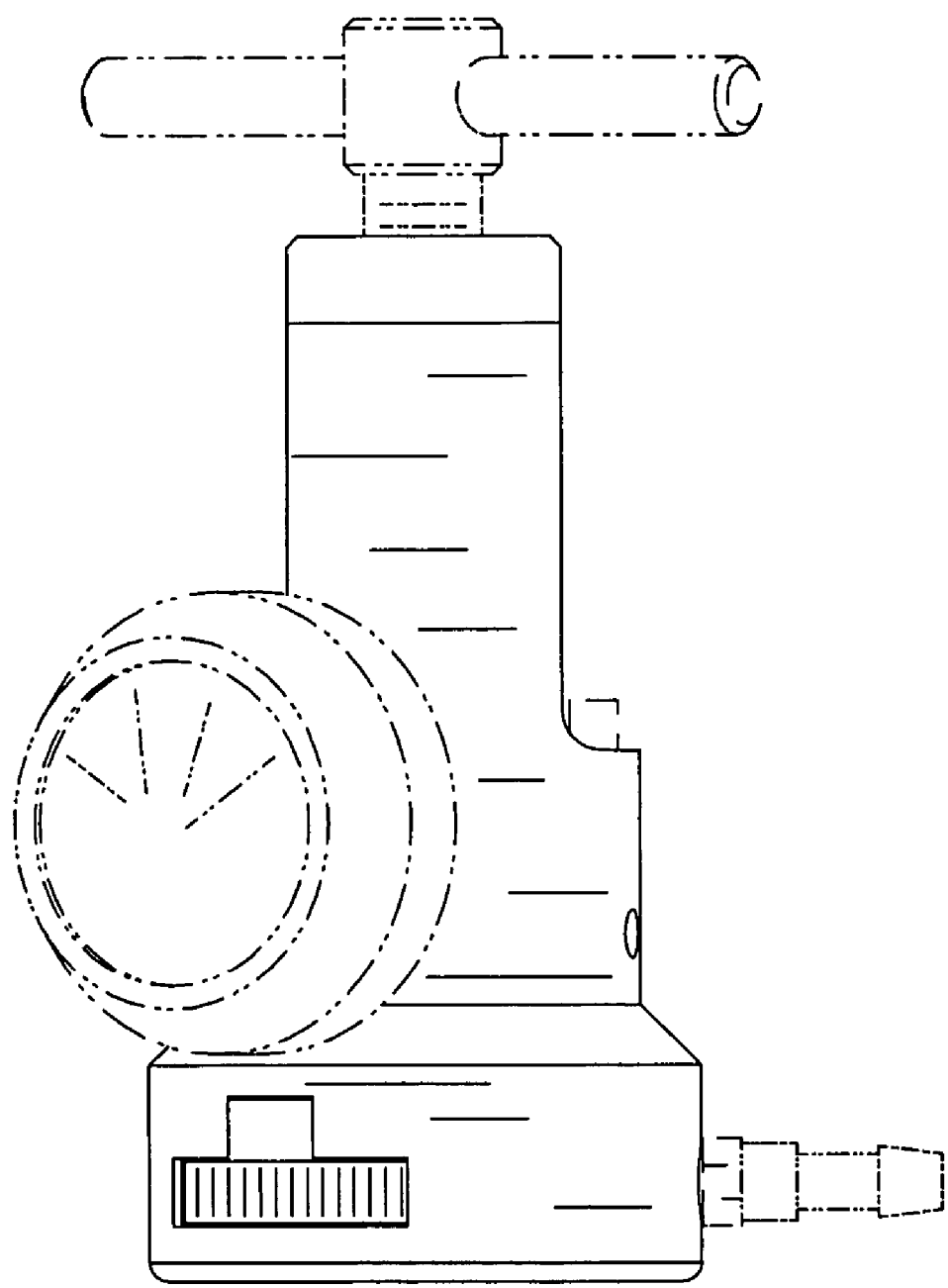
FIG. 53 is a second side view of the flow regulator of FIG. 49.
Figure 54:
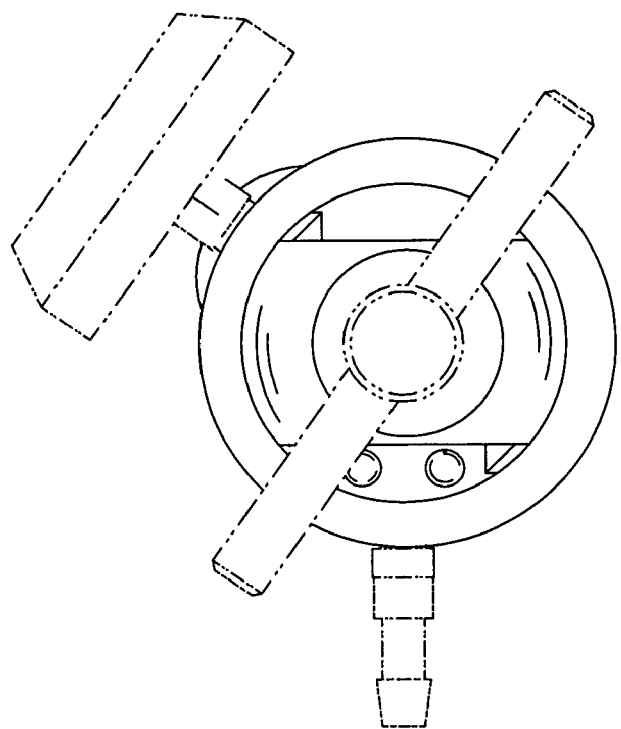
FIG. 54 is a top view of the flow regulator of FIG. 49.
Figure 55:
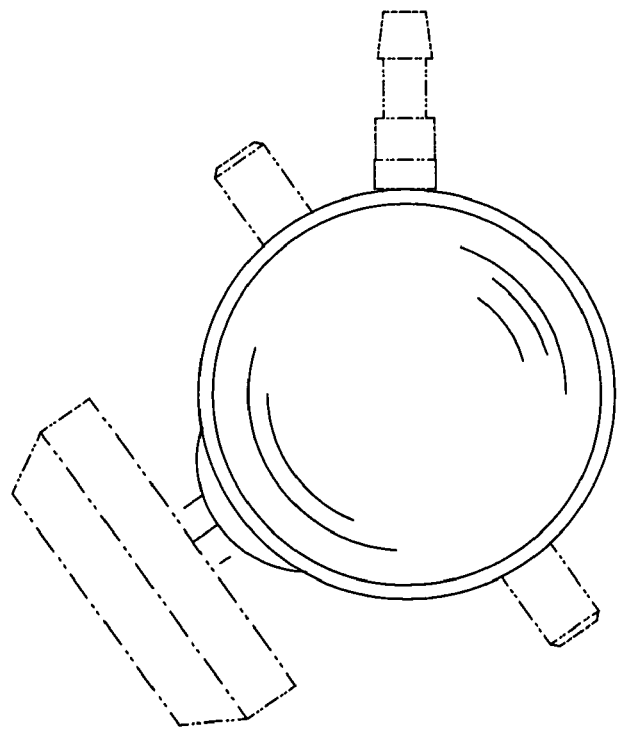
FIG. 55 is a bottom view of the flow regulator of FIG. 49.

As shown for example in FIG. 1A, body portion 102 includes a reduced diameter portion 103 proximate to flow selector 168. Further, reduced diameter portion 103 includes a window 105. As explained below window 105 permits an operator to see at least one indicia 169 (see FIG. 19) on flow selector 168. In one embodiment, reduced diameter portion 103 extends about 7 percent of the length $A_2$ of body portion 102 and has a diameter which is about 94 percent of the diameter B of body portion 102. In one example, a longitudinal length of reduced diameter portion and body portion 102 are about 0.25 inches and about 3.638 inches, respectively (about 6.87 percent of length $A_2$), and a diameter of reduced diameter portion 103 and diameter of body portion 102 are about 1.285 inches and about 1.365 inches, respectively (about 94.1 percent of diameter B).

Figure 4:
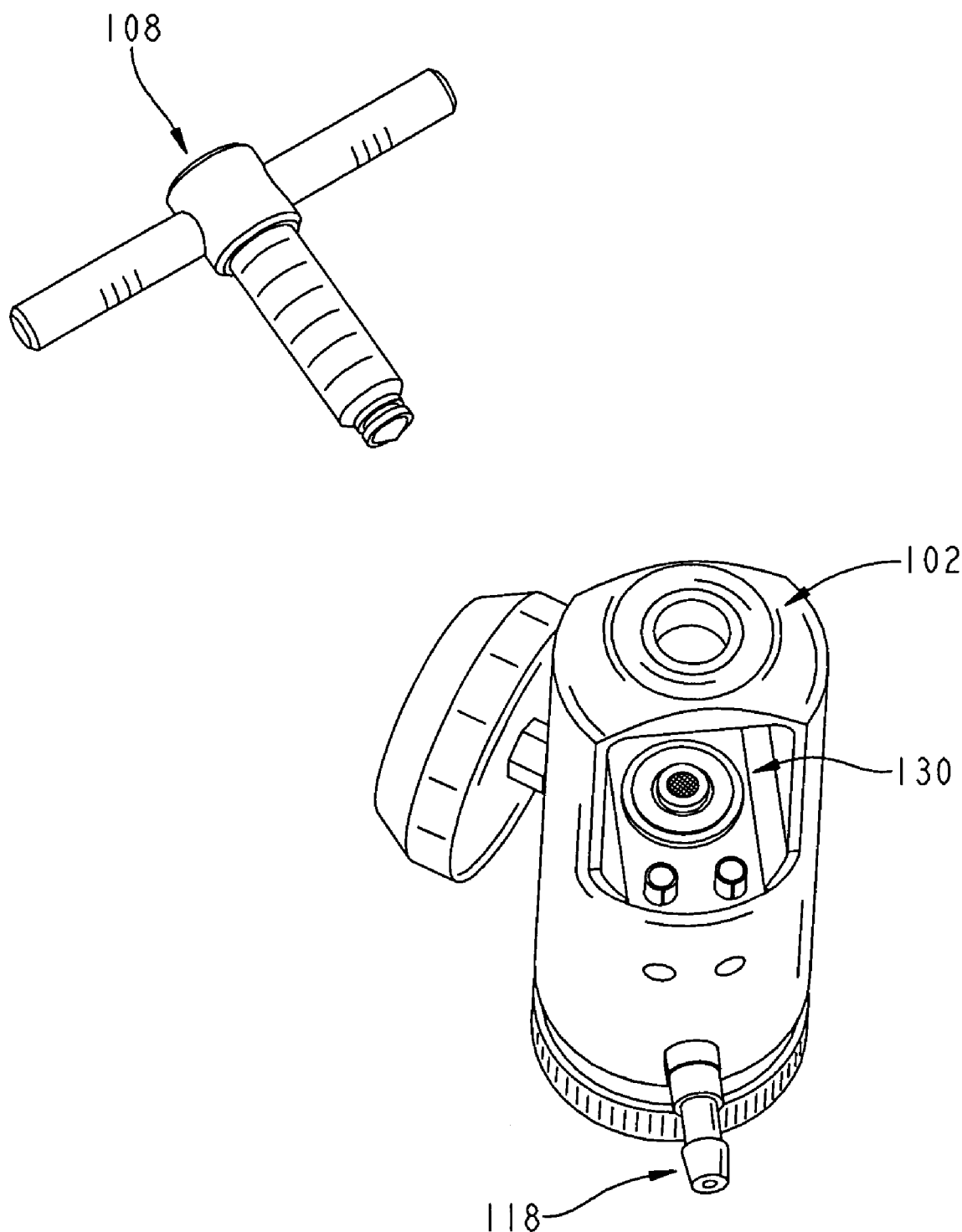
FIG. 4 is a perspective view of the flow regulator of FIG. 1A with a retainer unassembled.
Figure 5:
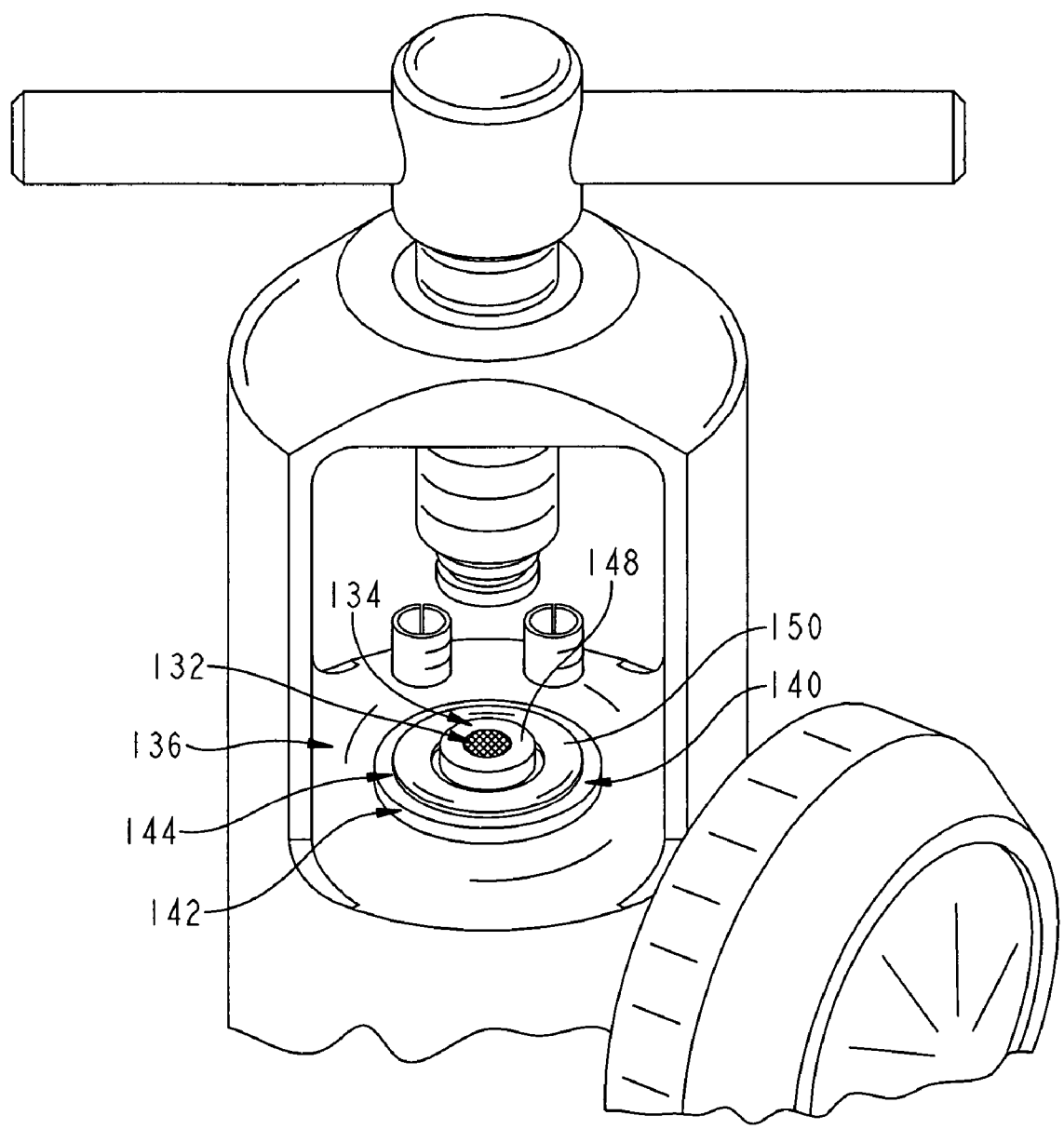
FIG. 5 is a perspective view of the fluid regulator of FIG. 1A showing a fluid inlet retainer assembled thereto, the fluid inlet retainer having a fluid inlet and at least one filter positioned in the fluid inlet.

Referring to FIGS. 3-5, fluid inlet 110 includes a fluid conduit 120 through a fluid inlet retainer 130. Fluid inlet retainer 130 includes at least one filter 132, a filter retainer 134, and a seal ring 136. Filter retainer 134 is threadably received within a central opening in body portion 102. Filter retainer 134 includes fluid conduit 120 which has an enlarged portion 138 for receiving one or more filters 132. Filters 132 remove impurities from the medical fluid. In one example, filter 132 is designed to filter particles which are about 0.66 microns or larger. Fluid inlet retainer 130 is shown in U.S. Provisional Application Ser. No. 60/606,288, filed on Sep. 1, 2004, titled METHOD AND APPARATUS FOR REGULATING FLUID FLOW OR CONSERVING FLUID FLOW, the disclosure of which is expressly incorporated by reference herein.

In one embodiment, two filters are positioned within enlarged portion 138. In another embodiment, three filters are positioned within enlarged portion 138. Exemplary filters include sintered bronze filters having a length of about 0.188 inches and a diameter of about 0.130 inches or filters made from other materials which will not ignite in the presence of oxygen flowing there through at relatively high pressures, such as about 500 to about 3000 psi. In one example filter retainer 134 is made from brass. In alternative embodiment, filter retainer 134 is made from other materials which will not ignite in the presence of oxygen flowing there through at relatively high pressures.

Seal ring 136 includes a seal 140 and a support 142. In one example, seal 140 is made of a flouroelastomer, Viton®, having a durometer of about 75 and support 142 is made of brass. Referring to FIG. 5, seal 140 is received within a central opening 144 in support 142 and axially extends outward beyond the axial surfaces of support 142. Seal ring 136 is positioned over filter retainer 134 such that a first portion 146 of seal 140 contacts one of body 102 or filter inlet retainer 134 and such that a top portion 148 of filter inlet retainer 134 extends axially beyond a second portion 150 of seal 140.

First portion 146 of seal 140 provides a seal between one of body 102 and filter retainer 134 and support 142 when the source of pressurized fluid is coupled to flow regulator 100. Second portion 150 of seal 140 provides a seal between support 142 and the source of pressurized fluid when the source of pressurized fluid is coupled to flow regulator 100. As such, when the source of pressurized fluid is coupled to flow regulator 100, seal ring 136 prevents or at least minimizes the passage of fluid from the source of pressurized fluid to anywhere (such as atmosphere) other than fluid conduit 120 of fluid inlet retainer 130.

Figure 6:
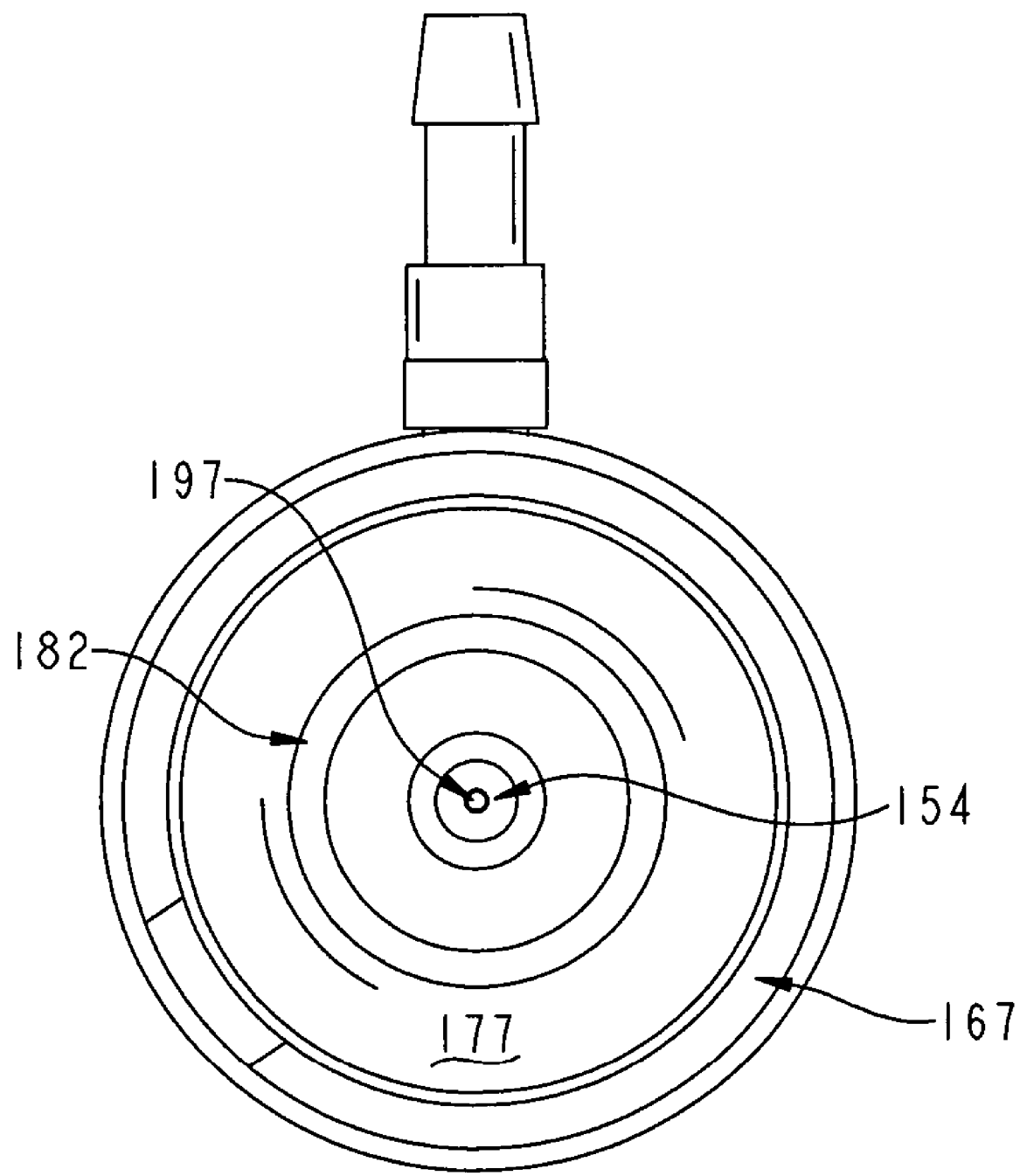
FIG. 6 is a perspective view of the interior of a housing of the fluid regulator of FIG. 1A showing the fluid inlet retainer assembled thereto, fluid inlet retainer having a fluid outlet.
Figure 7:
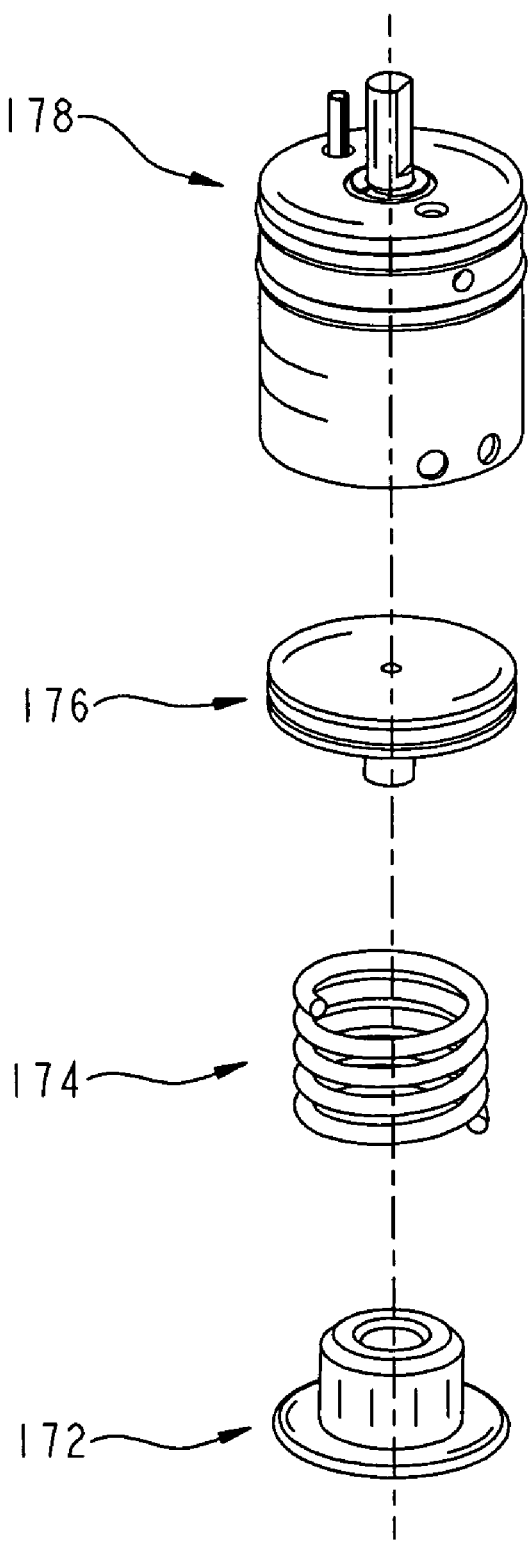
FIG. 7 is a perspective view of an unassembled pressure reduction section of the fluid regulator of FIG. 1A, the pressure reduction section including a housing, a vent mechanism, a biasing member, and a piston.

Fluid conduit 120 is generally shown as a central longitudinal conduit and includes a fluid outlet 154 (see FIG. 6). The diameter of fluid outlet 154 is generally reduced relative to the diameter of enlarged portion 138 which receives filter 132. In one example, a diameter of fluid outlet 154 is about 0.029 inches. Fluid which passes through filters 132 passes through fluid outlet 154 and is presented to a pressure reduction section 170.

Referring to FIG. 3, fluid inlet retainer 130 further includes at least one radial fluid conduit 156 which is in fluid communication with fluid conduit 120. When fluid inlet retainer 130 is coupled to body portion 102 radial fluid conduit 156 is in fluid communication with a radial passageway 158 in body portion 102. Passageway 158 is in fluid communication with a recess in body portion 102 which is designed to threadably receive a pressure gauge 160. Referring to FIG. 1, pressure gauge 160 includes a face 162 visible through a window 164 (FIG. 3) which includes indicia to provide an operator with an indication of the pressure of the fluid in the source of pressurized fluid. In one example, the window is made of Lexan. Gauge 160 includes a protective outer member. In one example, the protective outer member is made of rubber.

Fluid from radial fluid conduit 154 is prevented from passing to atmosphere adjacent fluid inlet 110 due to seal 140 of seal ring 136 and is prevented from entering cavity 167 (see FIG. 6) in body portion 102 due to seal 166 received by a groove on filter retainer 134 and positioned between filter retainer 134 and the channel in body portion 102 which receives filter retainer 134.

Referring to FIGS. 3 and 7-9, pressure reduction section 170 is shown. Pressure reduction section 170 includes a vent mechanism 172, a biasing member 174, a piston 176, and a housing 178. Pressure reduction section 170 is configured to receive a high pressure of fluid, such as greater than 500 psi, and to provide a lower pressure, such as about 5 psi, about 15 psi, about 20 psi, about 22 psi, about 27 psi, about 50 psi, about 60 psi, and the range of about 5 psi to about 60 psi, to one or more fluid inlet passages. Pressure reduction section 170 including vent mechanism 172, biasing member 174, and piston 176 is generally shown with a modified version of housing 178 in U.S. Provisional Application Ser. No. 60/606, 288, filed on Sep. 1, 2004, titled METHOD AND APPARATUS FOR REGULATING FLUID FLOW OR CONSERVING FLUID FLOW, and U.S. Provisional Application Ser. No. 60/548,058, filed on Feb. 26, 2004, titled FLOW REGULATOR, the disclosures of which are expressly incorporated by reference herein. As explained in the above referenced applications, the modified housing includes an axle to support a flow selector/flow restrictor, the axle either being solid or containing a fluid conduit which is in fluid communication with the interior of the housing.

Figure 8:
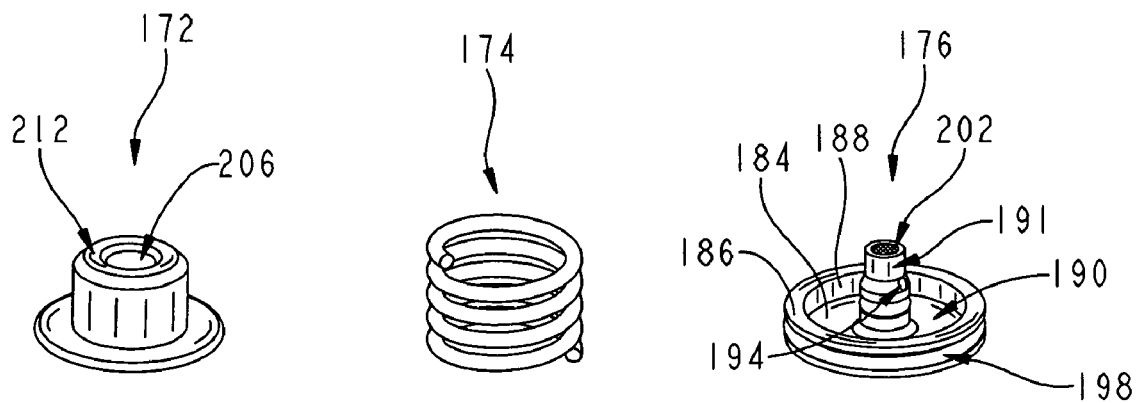
FIG. 8 is a perspective view of the vent mechanism, biasing member, and piston of FIG. 7.
Figure 9:
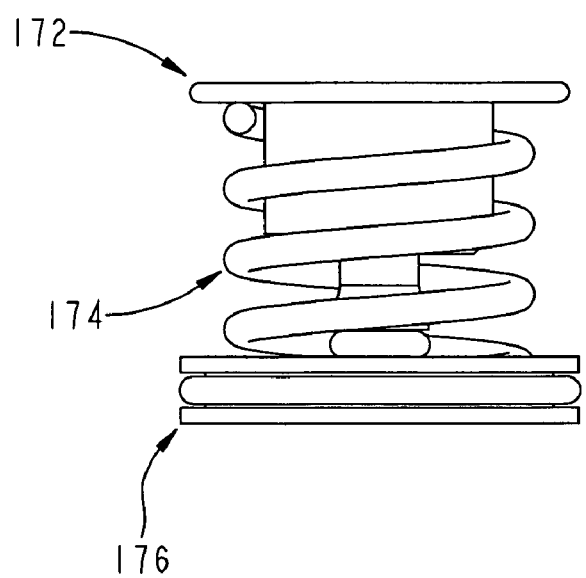
FIG. 9 is a perspective view of an assembly of the vent mechanism, biasing member, and piston of FIG. 7.
Figure 10:
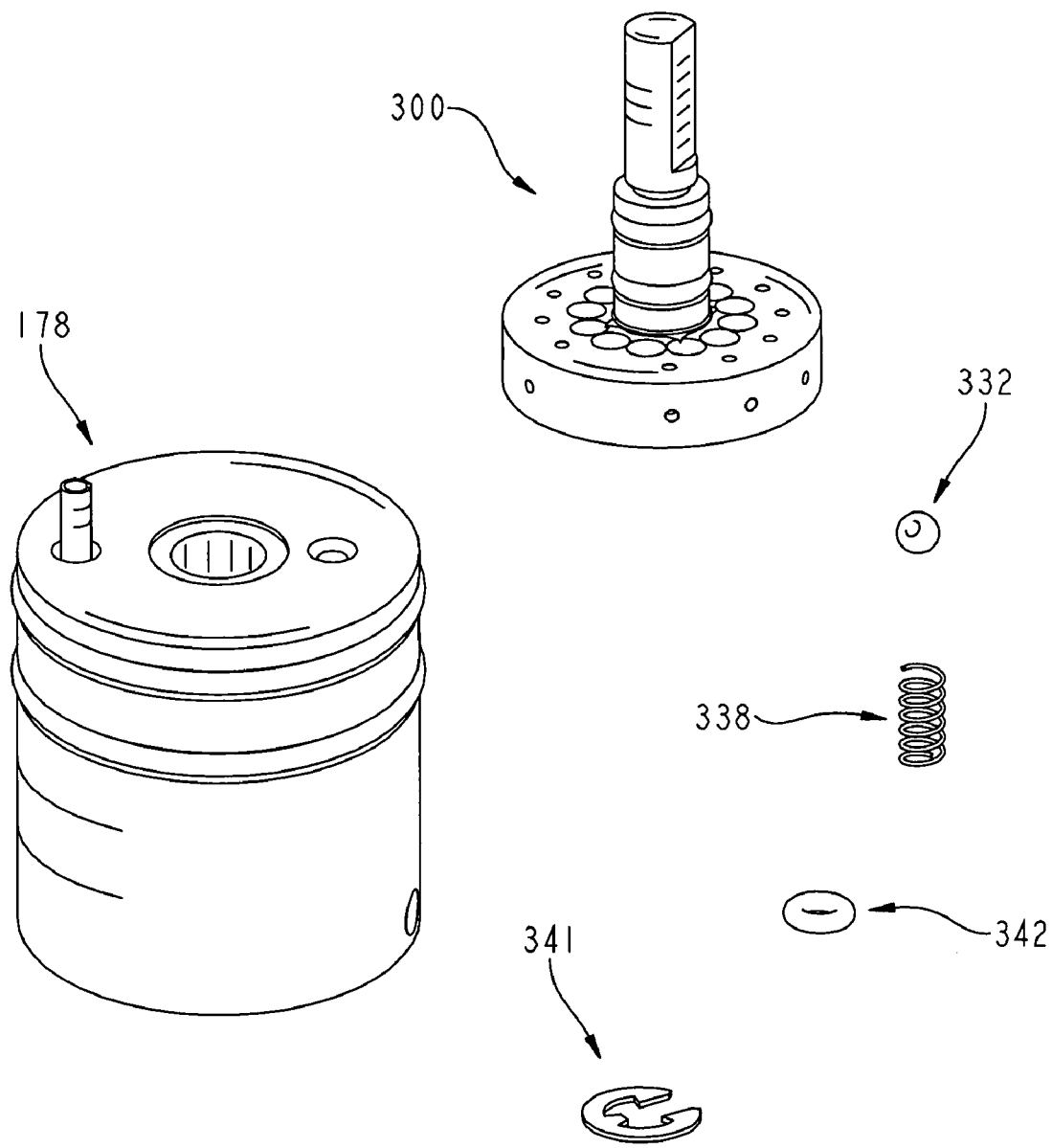
FIG. 10 is a perspective view of the housing of the pressure reduction section of FIG. 7 along with among other items a flow restrictor and an alignment member.
Figure 11:
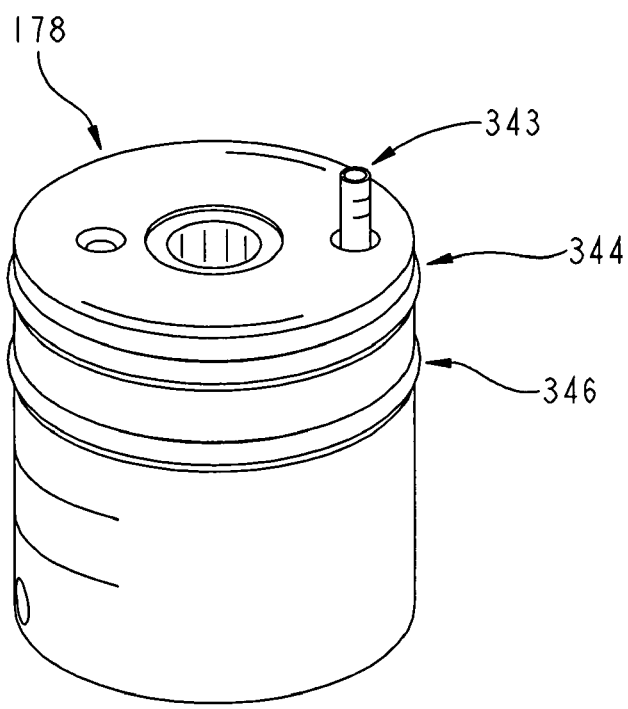
FIG. 11 is a perspective top view of the housing of the pressure reduction section.
Figure 12:
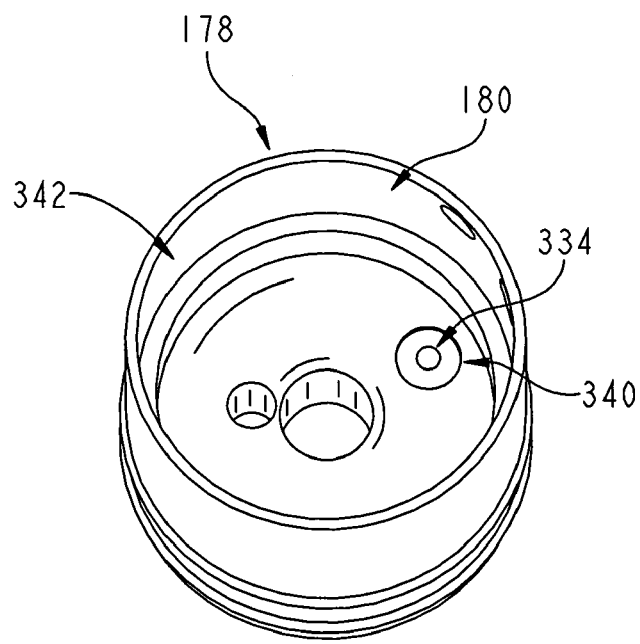
FIG. 12 is a perspective bottom view of the housing of the pressure reduction section.

As shown in FIG. 9, when assembled biasing member 174 is positioned between vent mechanism 172 and piston 176. Vent mechanism 172, biasing member 174, and piston 176 are each generally received within a cavity 180 (see FIG. 12) of housing 178. When assembled, vent mechanism 172 is positioned adjacent fluid outlet 154 of fluid inlet retainer 130. A seal 182 (see FIG. 3) is positioned between a first surface 179 of vent mechanism 172 and an axial surface 177 (see FIG. 6) of body portion 102. Referring to FIG. 8, piston 176 includes a seat surface 184 for receiving biasing member 174. Seat surface 184 is offset from axial surface 186 and is bounded by radial surface 188 thereby forming a recess 190. Recess 190 assists in the retention of biasing member 174 and reduces the overall length of the combination of vent mechanism 172, biasing member 174, and piston 176 (resulting in a reduction of the length of flow regulator 100). In one embodiment, the depth of recess 190 from axial surface 186 is about 74% of the distance from axial surface 186 to back surface 196. In one example the depth of recess 190 is about 0.125 inches and the separation between axial surface 186 and back surface 196 is about 0.169 inches. In one embodiment, piston 176 is made of brass.

In one embodiment, biasing member 174 is a compression spring. In one example, the spring is made of stainless steel with a load height of about 0.425 inches and a solid height of about 0.38 inches. The spring has a load of about 31.3 pounds.

Further, piston 176 includes a stem 191 (see FIG. 8) which includes a central fluid conduit 192 and a transverse fluid conduit 194. As explained in more detail below, fluid enters piston 176 through transverse fluid conduit 194, flows through fluid conduit 192, and exits piston 176 proximate to a back surface 196 of piston 176. Stem 191 is received in a central passageway 206 in vent mechanism 172. The height of vent mechanism 172 is chosen such that passageway 206 serves as a guide for piston 176 and to permit the proper travel of piston 176 in directions 208 and 210. To this end recess 190 receives an end 212 of vent mechanism 172 as piston 176 travels in direction 210. Therefore, the inclusion of recess 190 in piston 176 permits the length of vent mechanism 172 to be longer and provide a more stable guide for piston 176, while maintaining the overall reduced length of regulator 100 as discussed above. In one embodiment, end 212 moves completely into recess 190 to contact bottom surface 184 of recess 190.

Piston 176 includes a radial groove which receives a seal 198. Seal 198 provides a seal between piston 176 and housing 178 such that fluid is prevented from reaching back surface 196 of piston 176 except through fluid conduit 192. A recess 200 is formed in the end of stem 191 to receive a seal 202. Seal 202 is positioned such that it can contact a seat surface 197 (see FIG. 6) of fluid inlet retainer 130. In one example, seal 202 is a made of a glass filled Teflon, such as 15% glass filled Teflon.

Pressure reduction section 170 is held in place relative to body portion 102 by a retainer 210. Retainer 210 is shown as a clip that is received in a groove of cavity 180 of body 102. In an alternative embodiment, pressure reduction section 170 is threadably received in cavity 180, is press fit into cavity 180, or secured by other suitable methods.

Figure 14:
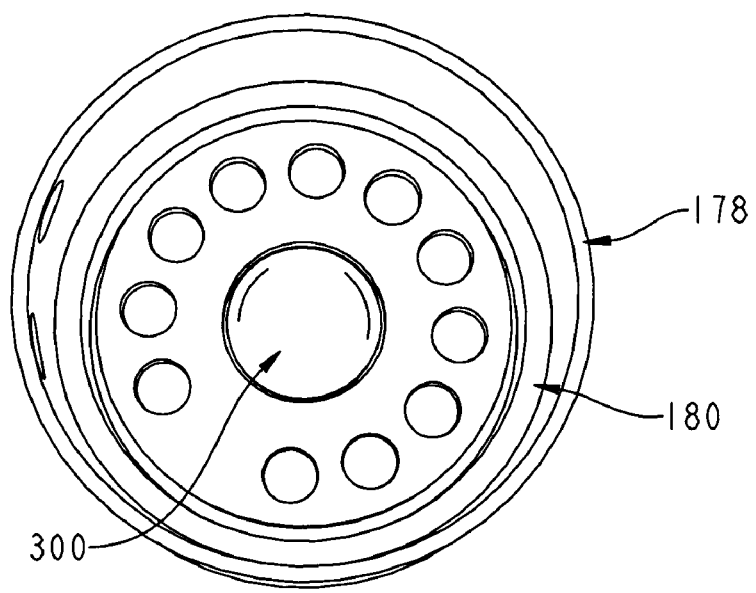
FIG. 14 is a perspective bottom view of the housing of the pressure reduction section having the flow restrictor assembled thereto.
Figure 15A:
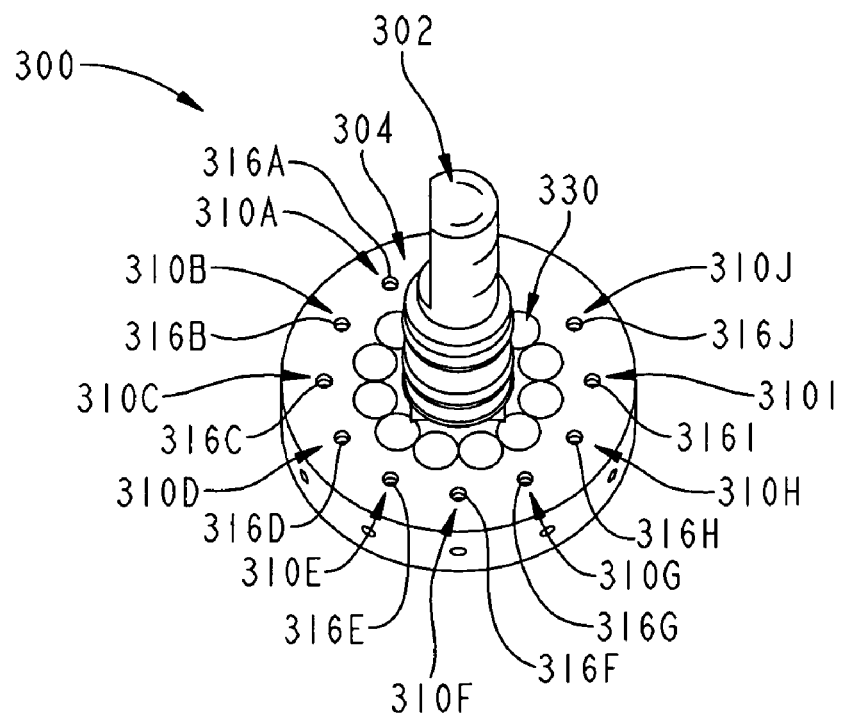
FIG. 15A is a perspective top view of the flow restrictor.
Figure 15B:
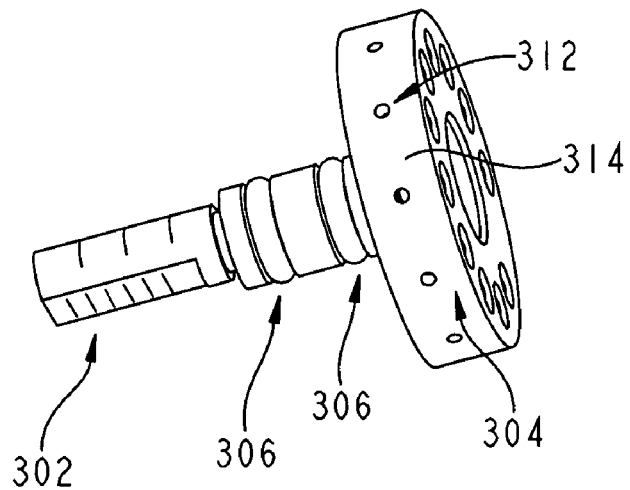
FIG. 15B is a perspective side view of the flow restrictor.
Figure 15C:
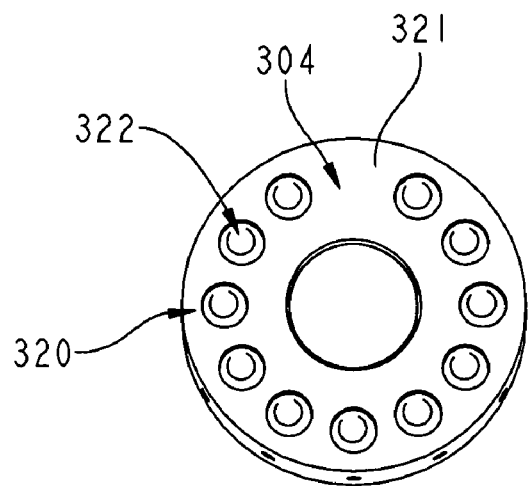
FIG. 15C is a perspective bottom view of the flow restrictor.
Figure 16:
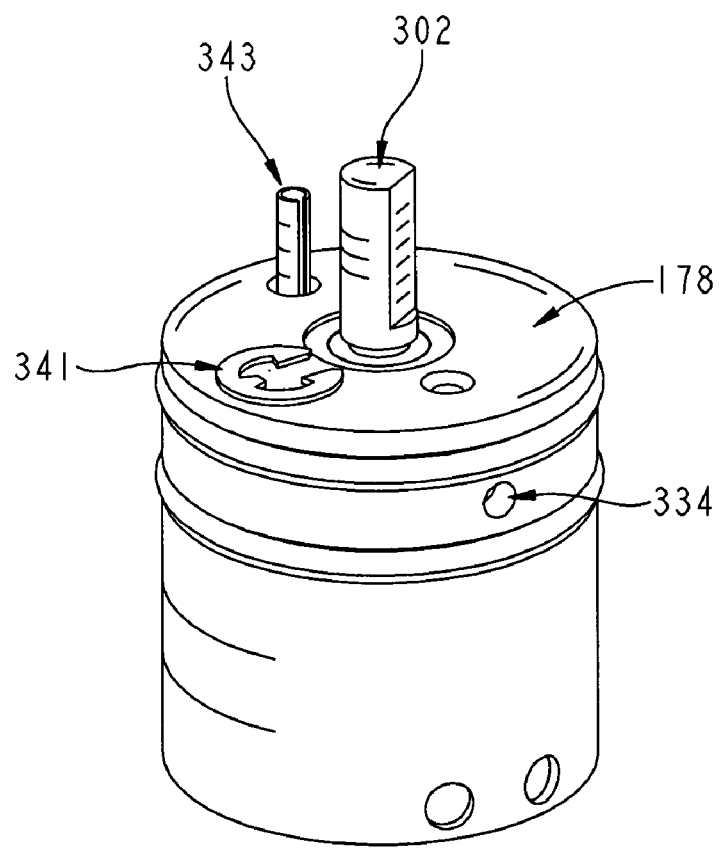
FIG. 16 is a perspective view of the flow restrictor received by the housing of the pressure reduction section and a retainer.
Figure 17:
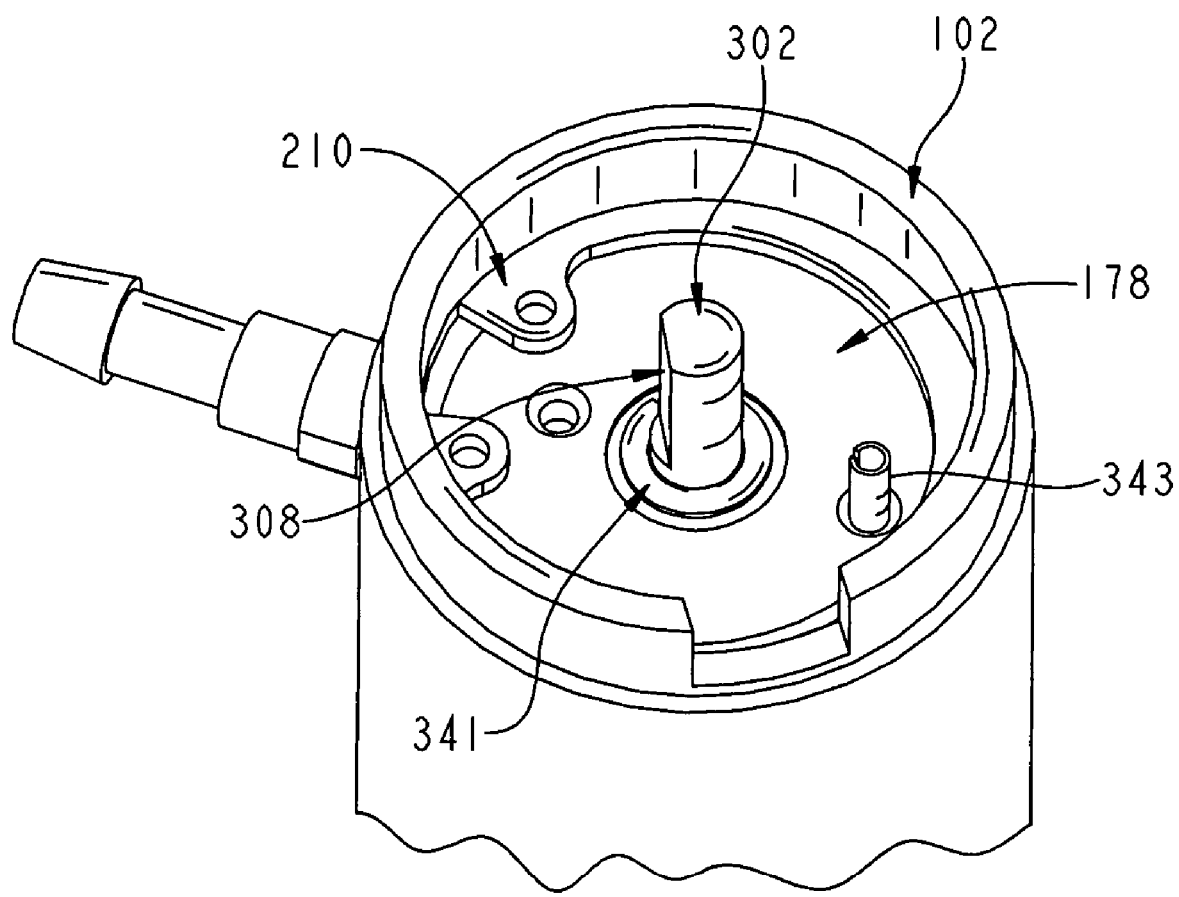
FIG. 17 shows the flow restrictor coupled to the housing of the pressure reduction section and the pressure reduction section coupled to the body of the fluid regulator.
Figure 18:
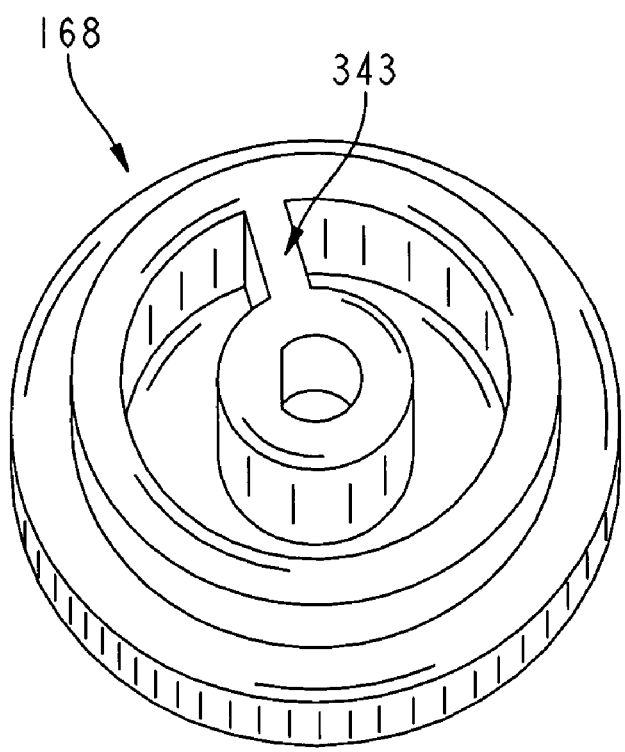
FIG. 18 is a bottom view of a flow selector.

Referring to FIGS. 14-16, a flow restrictor 300 includes a stem 302 and a disk 304. As shown in FIG. 16, stem 302 is received through an opening in housing 178 and extends above an end surface of housing 178. Stem 302 is received through an opening in housing 178 and is rotatable relative to housing 178. Stem 302 includes two recesses each of which receives a seal 306. Seals 306 seal between housing 178 and flow restrictor 300. A first end of stem 302 includes a notch 308 which is received in a mating opening in flow selector 168. Notch 308 effectively couples flow restrictor 300 and flow selector 168 together such that a rotation of flow selector 168 by a user results in a corresponding rotation of flow restrictor 300. The operation of flow restrictor 300 is discussed herein.

Disk 304 includes a plurality of fluid conduits 310A-K, each of which includes a fluid inlet 312 located in a radial surface 314 of disk 304 and a fluid outlet 316 located in an axial surface 318 of disk 304. Disk 304 further includes a plurality of openings 320 in axial surface 321, each one aligned with a respective fluid outlet 316. Openings 320 are sized to receive a respective occluder 322 which is positioned in opening 320 such that at least a portion of occluder 322 reduces the cross-sectional area of at least one of the respective fluid inlet 312 and fluid outlet 314. The amount that occluder 322 is advanced in opening 320 is controlled such that each fluid conduit 310 provides a calibrated amount of fluid flow. In one example occluder 322 is a spherical ball.

In another embodiment, occluders 322 are received through an opening in a radial surface 314 of disk 304 and fluid inlet 312 intersects with axial surface 321, such that fluid conduit 310 is generally a straight fluid conduit. An exemplary arrangement of fluid conduits and respective occluder is disclosed in U.S. Provisional Application Ser. No. 60/606,288, filed on Sep. 1, 2004, titled METHOD AND APPARATUS FOR REGULATING FLUID FLOW OR CONSERVING FLUID FLOW, and U.S. Provisional Application Ser. No. 60/548,058, filed on Feb. 26, 2004, titled FLOW REGULATOR, the disclosures of which are expressly incorporated by reference herein.

In yet another embodiment, occluders 322 are received through an opening in a axial surface 318 of disk 304, fluid inlet 312 intersects with axial surface 321, and fluid outlet 316 intersects with radial surface 314. An exemplary arrangement of fluid conduits and respective occluders is disclosed in U.S. Pat. No. 4,366,947 to Voege, issued Jan. 4, 1983, the disclosure of which is expressly incorporated by reference herein.

Disk 304 further includes a plurality of indexes or recesses 330 which cooperate with a detent, such as ball 332 in FIG. 3. Indexes 330 are positioned such that each one corresponds to the alignment of a respective fluid passage 310 in flow restrictor 300 with a fluid outlet passage 334 in housing 178. In another embodiment, indexes 330 are bumps which cooperate with one or more depressions on housing 178. Detent 332 is at least partially received in an opening 336 in housing 178 and is biased into index 330 by a biasing member 338. Flow restrictor 300 is coupled to housing 178 with a retainer 341.

Seals 340 and 342 are provided to seal between housing 178 and flow restrictor 300 such that only fluid exiting the respective fluid outlet 316 which is aligned with fluid outlet 334 in housing 178 is permitted to pass into fluid outlet 334. Fluid passes through fluid outlet 334 in housing 178 and into hose barb 118 for delivery to the patient. The exterior of housing 178 and body 102 is sealed by two seals 344 and 346 (see FIG. 16). Housing 178, in one embodiment, is made of aluminum to reduce the overall weight of flow regulator 100. The reduced weight is beneficial when shipping the regulators and an aluminum sleeve is less expensive to produce. In this embodiment, the fluid flows through the aluminum wall of housing 178. Despite being made of aluminum, the housing 178 of this embodiment complies with flammability requirements. In another embodiment, housing 178 is made of brass.

The operation of flow regulator 100 is described with reference to FIG. 3. In the absence of any fluid flow biasing member 174 of pressure reduction section 170 biases piston 176 in direction 208 relative to vent mechanism 172 such that back surface 196 of piston 176 is positioned adjacent flow restrictor 300 and such that vent mechanism 172 is in contact with seal 182. Flow regulator 100 is coupled to a source of pressurized fluid such that high pressure fluid enters fluid inlet retainer 130 from the source of pressurized fluid. The fluid then passes through filters 132, and exits fluid inlet retainer 130 through fluid outlet 154. This fluid passes through transverse conduit 194 of piston 176 and down central conduit 192 of piston 176. The fluid, assuming it is at a high enough pressure, builds up on the back side of piston 176 (adjacent back surface 196) causing piston 176 to move generally in direction 210. If flow restrictor 300 is set such that fluid is not permitted to pass through flow restrictor 300 (none of fluid passages 310 are aligned with fluid outlet 334 in housing 178) to fluid outlet 114 in hose barb 118, then piston 176 continues to move in direction 210 against the bias of biasing member 174 due to the pressure buildup on the backside of piston 176. As piston 176 moves in direction 210, seal 202 of piston 176 moves closer to seat surface 197 of fluid inlet retainer 130. Assuming pressure continues to build (flow restrictor is not moved to permit fluid to exit through fluid outlet 334) seal 202 contacts seat surface 197 and fluid flow is prevented from exiting fluid inlet retainer 130.

As flow restrictor 300 is moved to a flow setting, fluid is permitted to flow through the corresponding fluid conduit 310 of flow restrictor 300, through fluid conduit 334 in housing 178, and hose barb 118. Flow restrictor 300 is moved to a flow setting by a user imparting a rotation to flow selector 168. Flow selector 168 in turn imparts a rotation to flow restrictor 300. The rotation of flow selector 168 is limited by a stop 343 which is coupled to housing 178 and which is received in a recess 345 of flow selector 168. Detent 332 cooperates with indexes 330 to provide an indication to the user of when a fluid channel 310 is aligned with fluid outlet 334. Further, window 105 in body 102 permits a user to visually perceive an indicia 169 on flow selector 168 that corresponds to the flow rate of the fluid channel 310 aligned with fluid outlet 334.

As fluid flows through flow restrictor 300 to fluid outlet 334, the pressure on the backside of piston 176 is reduced and piston 176 moves in direction 208 due to biasing member 174 such that seal 202 of piston 176 is spaced apart from seat surface 197. This movement once again permits fluid to exit fluid retainer 130 and to flow through piston 176. As time goes on and as long as the flow restrictor 300 is moved to a flow setting, a cyclic pattern is established wherein the pressure on the backside of piston 176 builds resulting in piston moving in direction 210 and thereby reducing the amount of fluid which flows to the backside of piston 176 followed by the pressure on the backside of piston 176 decreasing resulting in piston 176 moving in direction 208 and thereby increasing the amount of fluid which flows to the backside of piston 176.

Figure 13:
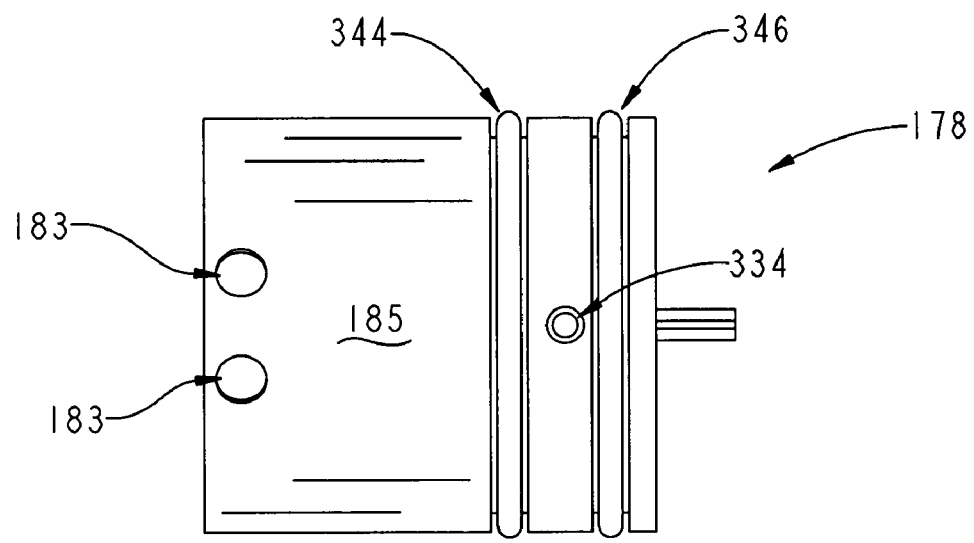
FIG. 13 is a perspective side view of the housing of the pressure reduction section.

Vent mechanism 172 also provides a safety feature to prevent a buildup of pressure in the interior of housing 178. Vent mechanism 172 includes a recess 173 which is in fluid communication with fluid outlet 154. As pressure builds up in recess 173 (potentially due to an obstruction of the fluid passage 192 in piston 176), vent mechanism 172 can move in direction 208 against the bias of biasing member 174. Such movement brings recess 173 into fluid communication with region 175 in housing 178. As shown in FIG. 13, housing 178 includes two vent openings 183 in wall 185. Vent openings 183 are aligned with corresponding vent openings 187 in body 102 and cooperate with vent openings 187 to bring region 175 in fluid communication with the air surrounding flow regulator 100. As such, an excessive pressure buildup may be vented to atmosphere.

FIGS. 20-27 illustrate exemplary features of the flow regulator of FIG. 1. The flow regulator depicted in FIGS. 20-27 is enlarged by a scale of 1.25.

FIGS. 28-34 illustrate exemplary features of a flow regulator having a housing, a flow selector partially contained within the housing and actuatable from the side of the housing, and a fluid outlet extending from the bottom of the flow regulator. An exemplary flow regulator as depicted in FIGS. 28-34 is disclosed in U.S. Provisional Application Ser. No. 60/606,288, filed on Sep. 1, 2004, titled METHOD AND APPARATUS FOR REGULATING FLUID FLOW OR CONSERVING FLUID FLOW, and U.S. Provisional Application Ser. No. 60/548,058, filed on Feb. 26, 2004, titled FLOW REGULATOR, the disclosures of which are expressly incorporated by reference herein.

FIGS. 35-41 illustrate exemplary features of a flow regulator having a housing, a flow selector partially contained within the housing and actuatable from the side of the housing, and a fluid outlet e extending from a radial surface of the flow regulator. An exemplary flow regulator as depicted in FIGS. 35-41 is disclosed in U.S. Provisional Application Ser. No. 60/606,288, filed on Sep. 1, 2004, titled METHOD AND APPARATUS FOR REGULATING FLUID FLOW OR CONSERVING FLUID FLOW, and U.S. Provisional Application Ser. No. 60/548,058, filed on Feb. 26, 2004, titled FLOW REGULATOR, the disclosures of which are expressly incorporated by reference herein.

FIGS. 42-48 illustrate exemplary features of a flow regulator having a housing, a flow selector partially contained within the housing and actuatable from the side of the housing, and a fluid outlet extending from the bottom of the flow regulator, the housing being a first diameter proximate to a yoke of the housing and a second diameter proximate to the flow selector. An exemplary flow regulator as depicted in FIGS. 28-34 is disclosed in U.S. Provisional Application Ser. No. 60/606,288, filed on Sep. 1, 2004, titled METHOD AND APPARATUS FOR REGULATING FLUID FLOW OR CONSERVING FLUID FLOW, and U.S. Provisional Application Ser. No. 60/548,058, filed on Feb. 26, 2004, titled FLOW REGULATOR, the disclosures of which are expressly incorporated by reference herein.

FIGS. 49-55 illustrate exemplary features of a flow regulator having a housing, a flow selector partially contained within the housing and actuatable from the side of the housing, and a fluid outlet e extending from a radial surface of the flow regulator, the housing being a first diameter proximate to a yoke of the housing and a second diameter proximate to the flow selector. An exemplary flow regulator as depicted in FIGS. 35-41 is disclosed in U.S. Provisional Application Ser. No. 60/606,288, filed on Sep. 1, 2004, titled METHOD AND APPARATUS FOR REGULATING FLUID FLOW OR CONSERVING FLUID FLOW, and U.S. Provisional Application Ser. No. 60/548,058, filed on Feb. 26, 2004, titled FLOW REGULATOR, the disclosures of which are expressly incorporated by reference herein.

The invention claimed is:

1. A fluid regulator, comprising:
a cylindrical body including a first portion configured to be coupled to a source of high pressure fluid and a second portion configured to be coupled to a cannula, the first portion including a fluid inlet and the second portion including a fluid outlet in fluid communication with the fluid inlet, the cylindrical body having an open end and a reduced diameter portion adjacent the open end;

a flow restrictor having at least a first fluid passage configured to provide a first restricted flow rate of fluid and a second fluid passage configured to provide a second restricted flow rate of fluid, the flow restrictor being received in the open end of the cylindrical body portion and moveable relative to the body portion so that one of the first fluid passage and the second fluid passage is selectively interposed between the fluid inlet of the body and the fluid outlet of the body to restrict the flow rate of fluid from the fluid inlet of the body to the fluid outlet of the body; and a flow selector coupled to the flow restrictor and positioned adjacent the open end of the cylindrical body portion, the flow selector including a first portion having a diameter larger than a diameter of the reduced diameter portion of the cylindrical body, wherein the cylindrical body includes a first diameter larger than the reduced diameter portion and the diameter of the first portion of the flow selector is substantially equal to the first diameter of the cylindrical body.

2. The fluid regulator of claim 1, wherein a longitudinal extent of the reduced diameter portion of the cylindrical body is about 7 percent of an overall length of the cylindrical body.

3. The fluid regulator of claim 1, wherein a longitudinal extent of the reduced diameter portion of the cylindrical body is about 0.25 inches.

4. The fluid regulator of claim 1, wherein the reduced diameter portion of the cylindrical body includes a window positioned so that a portion of a second portion of the flow selector is visible therethrough, the second portion of the flow selector being positioned within the open end of the cylindrical body, the visible portion of the second portion of the flow selector including an indicia indicating a flow rate of the one of the first fluid passage and the second fluid passage is selectively interposed between the fluid inlet of the body and the fluid outlet of the body.

5. The fluid regulator of claim 4, wherein the window is generally rectangular and is connected to a surface defining the open end of the cylindrical body.

6. A fluid regulator, comprising:

a cylindrical body including a first portion configured to be coupled to a source of high pressure fluid and a second portion configured to be coupled to a cannula, the first portion including a fluid inlet and the second portion including a fluid outlet in fluid communication with the fluid inlet, the cylindrical body having an open end and a reduced diameter portion adjacent the open end;

a flow restrictor having at least a first fluid passage configured to provide a first restricted flow rate of fluid and a second fluid passage configured to provide a second restricted flow rate of fluid, the flow restrictor being received in the open end of the cylindrical body portion and moveable relative to the body portion so that one of the first fluid passage and the second fluid passage is selectively interposed between the fluid inlet of the body and the fluid outlet of the body to restrict the flow rate of fluid from the fluid inlet of the body to the fluid outlet of the body;

a flow selector coupled to the flow restrictor and positioned adjacent the open end of the cylindrical body portion, the flow selector including a first portion having a diameter larger than a diameter of the reduced diameter portion of the cylindrical body; and a housing received within the open end of the cylindrical body, the housing including a recess in a first end and an aperture extending from a second end of the housing to the recess and a fluid conduit connecting a first axial surface of the recess and a radial surface of the housing, the flow restrictor being rotatably coupled to the housing and wherein the fluid conduit of the housing is in fluid communication with the fluid outlet of the second portion of the body and a respective fluid passage of the flow restrictor based on the position of the flow restrictor relative to the housing, wherein the reduced diameter portion of the cylindrical body includes a window positioned so that a portion of a second portion of the flow selector is visible therethrough, the second portion of the flow selector being positioned within the open end of the cylindrical body, the visible portion of the second portion of the flow selector including an indicia indicating a flow rate of the one of the first fluid passage and the second fluid passage is selectively interposed between the fluid inlet of the body and the fluid outlet of the body.

7. The fluid regulator of claim 6, wherein the housing further includes a stop coupled thereto and extending from the second end of the housing, the stop of the housing cooperating with a stop of the flow selector to limit the rotation of the flow selector relative to the housing.

8. The fluid regulator of claim 6, further comprising a pressure reduction section received within the recess of the housing and interposed between the flow restrictor and the fluid inlet of the first portion of the cylindrical body, the pressure reduction section being configured to reduce the pressure of the fluid provided to fluid inlet from the source of pressurized fluid prior to its presentation to the flow restrictor.

9. The fluid regulator of claim 8, wherein the pressure reduction section comprises:

a base member including a base portion and a guide portion extending from the base portion, the base member having a central passageway extending there through, the central passageway being positioned such that it is in fluid communication with the fluid inlet of the first portion of the cylindrical body;

a piston including a piston base portion and a stem portion, the stem portion being configured to be received by the central passageway in the guide portion of the base member, the piston having a fluid passageway there through with a fluid inlet in the stem portion and a fluid outlet in the piston base portion, the fluid outlet being in fluid communication with the flow restrictor; and a biasing member sized to receive the guide portion of the base member, a first end of the biasing member being positioned adjacent the base portion of the base member and a second end of the biasing member being positioned adjacent a seat surface of the piston base portion, the seat surface being located in a recess of the piston base portion, the recess being sized to receive a first end of the guide portion of the base member.

10. The fluid regulator of claim 9, wherein the first portion of the cylindrical body includes a yoke portion having an opening there through, the source of pressurized fluid being coupled to the yoke portion of the cylindrical body and the fluid inlet being located in the yoke portion.

11. A fluid regulator, comprising:

a cylindrical body including a first portion configured to be coupled to a source of high pressure fluid and a second portion configured to be coupled to a cannula, the first portion including a fluid inlet and the second portion including a fluid outlet in fluid communication with the fluid inlet, the cylindrical body having an open end and a reduced diameter portion adjacent the open end;

a flow restrictor having at least a first fluid passage configured to provide a first restricted flow rate of fluid and a second fluid passage configured to provide a second restricted flow rate of fluid, the flow restrictor being received in the open end of the cylindrical body portion and moveable relative to the body portion so that one of the first fluid passage and the second fluid passage is selectively interposed between the fluid inlet of the body and the fluid outlet of the body to restrict the flow rate of fluid from the fluid inlet of the body to the fluid outlet of the body;

a flow selector coupled to the flow restrictor and positioned adjacent the open end of the cylindrical body portion, the flow selector including a first portion having a diameter larger than a diameter of the reduced diameter portion of the cylindrical body;

a pressure reduction section being received in the open end of the body and positioned between the fluid inlet of the body and the flow restrictor, the pressure reduction section being configured to receive fluid at a first pressure from the fluid inlet and to provide fluid at a lower pressure to the flow restrictor; and a housing positioned within the open end of the body, the housing including a recess into which the flow selector and the pressure reduction section are positioned and a fluid conduit which is aligned with the fluid outlet of the body and selectively aligned with a respective fluid passage of the flow restrictor.

12. The fluid regulator of claim 11, further comprising a hose barb which is coupled to the fluid outlet of the body and extends into the fluid conduit of the housing.

13. The fluid regulator of claim 12, wherein the hose barb restrain the rotational movement of the housing relative to the body.

14. The fluid regulator of claim 11, wherein the longitudinal movement of the housing within the open end of the body is limited by a coupler which is received within a recess of the open end of the body, the coupler contacting a top portion of the housing.

15. The fluid regulator of claim 11, wherein the housing is coupled to the body with a coupler which extends into the housing from an exterior of the body.

16. The fluid regulator of claim 15, wherein the coupler is a hose barb in fluid communication with the fluid outlet of the housing.

17. A fluid regulator, comprising:

a body having an interior cavity accessible through an open end, a fluid inlet which is configured to receive a high pressure fluid from a source of pressurized fluid, and a fluid outlet;

a housing positioned in the interior cavity of the body, the housing including an interior cavity accessible from an open end of the housing, a fluid inlet accessible though the open end of the housing which is in fluid communication with the fluid inlet of the body and a fluid outlet in fluid communication with the fluid inlet of the housing and the fluid outlet of the body;

a pressure reduction section positioned within the interior cavity of the housing through the open end of the housing, the pressure reduction section being configured to receive the high pressure fluid from the fluid inlet of the body and to provide a lower pressure fluid to the fluid inlet of the housing, the pressure reduction section including:

a base member including a base portion and a guide portion extending from the base portion, the base member having a central passageway extending there through, the central passageway being positioned such that it is in fluid communication with the fluid inlet of the body;

a piston including a piston base portion and a stem portion, the stem portion being configured to be received by the central passageway in the guide portion of the base member, the piston having a fluid passageway there through with a fluid inlet in the stem portion and a fluid outlet in the piston base portion, the fluid outlet being in fluid communication with the fluid inlet of the housing; and a biasing member sized to receive the guide portion of the base member, a first end of the biasing member being positioned adjacent the base portion of the base member and a second end of the biasing member being positioned adjacent a seat surface of the piston base portion, the seat surface being located in a recess formed in the piston base portion, the recess being sized to receive a first end of the guide portion of the base member; and a rotatable flow restrictor including a flow control portion disposed within the interior cavity of the housing and a stem portion coupled to the disk portion and extending through an aperture connecting the cavity of the housing and a second end of the housing, the flow control portion including a plurality of fluid conduits each selectively being brought into fluid communication with the fluid conduit of the housing through the rotation of the flow restrictor relative to the housing.

18. The fluid regulator of claim 17, wherein the flow control portion of the flow restrictor includes a first axial surface containing the respective fluid outlets for each of the plurality of fluid conduits of the flow restrictor, a second axial surface including the respective fluid inlets for each of the plurality of fluid conduits of the flow restrictor, and a radial surface disposed between the first axial surface and the second axial surface, the radial surface including openings sized to receive respective occluders which are advanced into the respective fluid conduit to reduce a cross-sectional area of the respective fluid conduit of the flow restrictor.

19. The fluid regulator of claim 17, wherein the flow control portion of the flow restrictor includes a first axial surface including the respective fluid outlets for each of the plurality of fluid conduits of the flow restrictor, a second axial surface including the respective fluid inlets for each of the plurality of fluid conduits of the flow restrictor, and a radial surface disposed between the first axial surface and the second axial surface, the radial surface including openings sized to receive respective occluders which are advanced into the respective fluid conduit to reduce a cross-sectional area of the respective fluid conduit of the flow restrictor.

20. The fluid regulator of claim 17, wherein the flow control portion of the flow restrictor includes a first axial surface including the respective fluid inlets for each of the plurality of fluid conduits of the flow restrictor, a second axial surface including openings sized to receive respective occluders which are advanced into the respective fluid conduit to reduce a cross-sectional area of the respective fluid conduit of the flow restrictor, and a radial surface disposed between the first axial surface and the second axial surface including the respective fluid outlets for each of the plurality of fluid conduits of the flow restrictor.

21. The fluid regulator of claim 17, wherein the body is generally cylindrical having a first diameter and a reduced diameter portion, the reduced diameter portion being adjacent the open end.

22. The fluid regulator of claim 21, further comprising a flow selector coupled to the flow restrictor, the flow restrictor being positioned adjacent the open end of the cylindrical body such that a first portion of the flow selector is received in the open end of the cylindrical body and a second portion of the flow selector extends beyond the open end of the cylindrical body, the second portion of the flow selector having a diameter larger than the diameter of the reduced diameter portion.

23. The fluid regulator of claim 22, wherein the reduced diameter portion of the cylindrical body includes a window positioned so that a portion of the first portion of the flow selector is visible therethrough, the visible portion of the first portion of the flow selector including an indicia indicating a flow rate of the respective fluid conduit of the flow restrictor which is in fluid communication with the fluid conduit of the housing.

24. The fluid regulator of claim 17, further comprising a hose barb which is coupled to the fluid outlet of the body and extends into the housing.

25. The fluid regulator of claim 24, wherein the hose barb restrain the rotational movement of the housing relative to the body.

26. The fluid regulator of claim 17, wherein the longitudinal movement of the housing within the open end of the body is limited by a coupler which is received within a recess of the interior cavity of the body, the coupler contacting a top portion of the housing.

27. The fluid regulator of claim 17, wherein the housing is coupled to the body with a coupler which extends into the housing from an exterior of the body.

28. The fluid regulator of claim 27, wherein the coupler is a hose barb in fluid communication with the fluid outlet of the housing.

* * * * *